(12) United States Patent
Schulhauser et al.

(10) Patent No.: US 12,239,423 B2
(45) Date of Patent: Mar. 4, 2025

(54) DETECTION OF PATIENT CONDITIONS USING SIGNALS SENSED ON OR NEAR THE HEAD

(71) Applicant: Covidien LP, Mansfield, MA (US)

(72) Inventors: Randal C. Schulhauser, Phoenix, AZ (US); Jonathon E. Giftakis, Maple Grove, MN (US); Eric J. Panken, Edina, MN (US); John Wainwright, Foothill Ranch, CA (US); Nathalie Virag, Cottens (CH); Paul G. Krause, Mahtomedi, MN (US); Yong K. Cho, Excelsior, MN (US); Scott DeFoe, Andover, MN (US); Avram Scheiner, Vadnais Heights, MN (US); Ekaterina M. Ippolito, Shoreview, MN (US); David A. Anderson, Stanchfield, MN (US); Saul E. Greenhut, Aurora, CO (US); Mark R. Boone, Gilbert, AZ (US); Richard J. O'Brien, Hugo, MN (US)

(73) Assignee: Covidien LP, Mansfield, MA (US)

( * ) Notice: Subject to any disclaimer, the term of this patent is extended or adjusted under 35 U.S.C. 154(b) by 606 days.

(21) Appl. No.: 17/459,713

(22) Filed: Aug. 27, 2021

(65) Prior Publication Data
US 2022/0061678 A1    Mar. 3, 2022

Related U.S. Application Data

(60) Provisional application No. 63/071,997, filed on Aug. 28, 2020.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1117* (2013.01); *A61B 5/4035* (2013.01);
(Continued)

(58) Field of Classification Search
None
See application file for complete search history.

(56) References Cited

U.S. PATENT DOCUMENTS

| 4,201,222 A | 5/1980 | Haase |
| 4,907,597 A | 3/1990 | Chamoun |

(Continued)

FOREIGN PATENT DOCUMENTS

| AU | 2014228116 B2 | 1/2019 |
| CN | 1891144 A | 1/2007 |

(Continued)

OTHER PUBLICATIONS

Cipolla, "Chapter 5: Control of Cerebral Blood Flow", The Cerebral Circulation, Colloquium Series on Integrated Systems Physiology: From Molecule to Function, Morgan & Claypool Life Sciences, San Rafael, CA, 2009, Retrieved from the Internet on Mar. 7, 2021: URL: https://www.ncbi.nlm.nih.gov/books/NBK53082/?report=printable.

(Continued)

*Primary Examiner* — Mallika D Fairchild
*Assistant Examiner* — Thien Jason Tran
(74) *Attorney, Agent, or Firm* — Shumaker & Sieffert, P.A.

(57) ABSTRACT

A system comprises a sensor device and processing circuitry. The sensor device comprises a housing configured to be disposed above shoulders of a patient, a plurality of electrodes on the housing, a motion sensor, and sensing circuitry configured to sense a brain electrical signal and a cardiac electrical signal via the electrodes, and a motion signal via (Continued)

the motion sensor. The processing circuitry is configured to determine values over time of one or more parameters from the brain electrical signal, determine values over time of one or more parameters from the cardiac electrical signal, and generate at least one of a detection, prediction, or a classification a condition of the patient based on the values and the motion signal.

21 Claims, 26 Drawing Sheets

(51) Int. Cl.
    *A61B 5/021*     (2006.01)
    *A61B 5/024*     (2006.01)
    *A61B 5/0245*    (2006.01)
    *A61B 5/11*      (2006.01)
    *A61B 5/291*     (2021.01)

(52) U.S. Cl.
    CPC .......... *A61B 5/4094* (2013.01); *A61B 5/4561* (2013.01); *A61B 5/6814* (2013.01); *A61B 5/6822* (2013.01); *A61B 5/7264* (2013.01); *A61B 5/02125* (2013.01); *A61B 5/02405* (2013.01); *A61B 5/0245* (2013.01); *A61B 5/1102* (2013.01); *A61B 5/291* (2021.01); *A61B 2562/0219* (2013.01)

(56) References Cited

U.S. PATENT DOCUMENTS

| | | |
|---|---|---|
| 5,029,590 A | 7/1991 | Allain et al. |
| 5,305,746 A | 4/1994 | Fendrock |
| 5,458,117 A | 10/1995 | Chamoun et al. |
| 6,032,064 A | 2/2000 | Devlin et al. |
| 6,728,564 B2 | 4/2004 | Laehteenmaeki |
| 6,961,601 B2 | 11/2005 | Matthews et al. |
| 7,054,453 B2 | 5/2006 | Causevic et al. |
| 7,054,454 B2 | 5/2006 | Causevic et al. |
| 7,072,705 B2 | 7/2006 | Miga et al. |
| 7,130,673 B2 | 10/2006 | Tolvanen-Laakso et al. |
| 7,367,949 B2 | 5/2008 | Korhonen et al. |
| 7,398,115 B2 | 7/2008 | Lynn |
| 7,407,485 B2 | 8/2008 | Huiku |
| 7,447,541 B2 | 11/2008 | Huiku et al. |
| 7,471,978 B2 | 12/2008 | John et al. |
| 7,904,144 B2 | 3/2011 | Causevic et al. |
| 7,912,537 B2 | 3/2011 | Lee et al. |
| 8,068,903 B2 | 11/2011 | Virag et al. |
| 8,323,188 B2 | 12/2012 | Tran |
| 8,364,254 B2 | 1/2013 | Jacquin et al. |
| 8,370,287 B2 | 2/2013 | Snyder |
| 8,423,145 B2 | 4/2013 | Pless et al. |
| 8,603,014 B2 | 12/2013 | Alleman et al. |
| 8,738,121 B2 | 5/2014 | Virag et al. |
| 8,837,800 B1 | 9/2014 | Bammer et al. |
| 8,862,199 B2 | 10/2014 | Ko et al. |
| 8,885,285 B1 | 11/2014 | Nicholls et al. |
| 8,926,509 B2 | 1/2015 | Magar et al. |
| 9,119,656 B2 | 9/2015 | Bose et al. |
| 9,126,018 B1 | 9/2015 | Garrison |
| 9,149,229 B1 | 10/2015 | Tarler |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,370,313 B2 | 6/2016 | Mcpeck et al. |
| 9,399,118 B2 | 7/2016 | Kume et al. |
| 9,408,575 B2 | 8/2016 | Bordoley et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,532,748 B2 | 1/2017 | Denison et al. |
| 9,539,022 B2 | 1/2017 | Bowman |
| 9,561,345 B2 | 2/2017 | Garrison et al. |
| 9,579,028 B2 | 2/2017 | Bonmassar et al. |
| 9,579,119 B2 | 2/2017 | Cully et al. |
| 9,585,741 B2 | 3/2017 | Ma |
| D784,542 S | 4/2017 | Zwierstra et al. |
| 9,642,635 B2 | 5/2017 | Vale et al. |
| 9,655,633 B2 | 5/2017 | Leynov et al. |
| 9,675,264 B2 | 6/2017 | Acquista et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,814,886 B2 | 11/2017 | Zhou et al. |
| 9,861,783 B2 | 1/2018 | Garrison et al. |
| 9,878,160 B2 | 1/2018 | Pless et al. |
| 9,943,690 B2 | 4/2018 | Pless et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,182,723 B2 | 1/2019 | Evans et al. |
| 10,195,402 B2 | 2/2019 | Zhadkevich |
| 10,252,058 B1 | 4/2019 | Fuerst |
| 10,281,478 B2 | 5/2019 | Franco |
| 10,285,606 B2 | 5/2019 | Jensen |
| 10,285,617 B2 | 5/2019 | Toth et al. |
| 10,335,083 B2 | 7/2019 | Keteyian et al. |
| 10,398,319 B2 | 9/2019 | Wang et al. |
| 10,463,271 B2 | 11/2019 | Intrator |
| 10,555,861 B2 | 2/2020 | Zwierstra et al. |
| 10,575,741 B2 | 3/2020 | Kim et al. |
| 10,575,818 B2 | 3/2020 | O'brien et al. |
| 10,610,200 B2 | 4/2020 | Arant et al. |
| 10,616,473 B2 | 4/2020 | Costa et al. |
| 10,617,388 B2 | 4/2020 | Flores, II et al. |
| 10,743,809 B1 | 8/2020 | Kamousi et al. |
| 10,779,747 B2 | 9/2020 | Simon |
| 10,786,209 B2 | 9/2020 | Park et al. |
| 11,006,841 B2 | 5/2021 | Wainwright et al. |
| 11,399,761 B2 | 8/2022 | Intrator |
| 11,457,866 B2 | 10/2022 | Kesinger et al. |
| 2002/0002390 A1 | 1/2002 | Fischell et al. |
| 2002/0099412 A1 | 7/2002 | Fischell et al. |
| 2002/0169485 A1 | 11/2002 | Pless et al. |
| 2003/0093004 A1 | 5/2003 | Sosa et al. |
| 2004/0163648 A1 | 8/2004 | Burton |
| 2004/0220644 A1 | 11/2004 | Shalev et al. |
| 2004/0243017 A1 | 12/2004 | Causevic |
| 2005/0113704 A1 | 5/2005 | Lawson et al. |
| 2005/0203366 A1 | 9/2005 | Donoghue et al. |
| 2006/0217614 A1 | 9/2006 | Takala et al. |
| 2006/0224421 A1 | 10/2006 | St. Ores et al. |
| 2007/0010723 A1 | 1/2007 | Uutela et al. |
| 2007/0021687 A1 | 1/2007 | Keith et al. |
| 2007/0032736 A1 | 2/2007 | Finnigan et al. |
| 2007/0167694 A1 | 7/2007 | Causevic et al. |
| 2007/0249954 A1 | 10/2007 | Virag et al. |
| 2008/0081980 A1 | 4/2008 | Maschke et al. |
| 2008/0139908 A1 | 6/2008 | Kurth |
| 2008/0167540 A1 | 7/2008 | Korhonen et al. |
| 2008/0208073 A1 | 8/2008 | Causevic |
| 2008/0208074 A1 | 8/2008 | Snyder et al. |
| 2008/0243021 A1 | 10/2008 | Causevic et al. |
| 2008/0294019 A1 | 11/2008 | Tran |
| 2009/0247894 A1 | 10/2009 | Causevic |
| 2009/0290772 A1 | 11/2009 | Avinash et al. |
| 2010/0121214 A1 | 5/2010 | Giftakis et al. |
| 2010/0274152 A1 | 10/2010 | Mcpeck et al. |
| 2011/0053859 A1 | 3/2011 | Deadwyler et al. |
| 2011/0054934 A1 | 3/2011 | Vesto |
| 2011/0066055 A1 | 3/2011 | Bharmi et al. |
| 2011/0245629 A1* | 10/2011 | Giftakis ............... A61B 5/1116 600/301 |
| 2011/0245633 A1 | 10/2011 | Goldberg et al. |
| 2011/0245707 A1 | 10/2011 | Castle et al. |
| 2011/0270117 A1* | 11/2011 | Warwick ............ A61B 5/0006 600/544 |
| 2012/0046558 A1 | 2/2012 | Virag et al. |

(56) References Cited

U.S. PATENT DOCUMENTS

| | | | |
|---|---|---|---|
| 2012/0123232 A1* | 5/2012 | Najarian | G16Z 99/00 600/407 |
| 2013/0030461 A1 | 1/2013 | Marks et al. | |
| 2013/0281788 A1 | 10/2013 | Garrison | |
| 2013/0303900 A1 | 11/2013 | Nowinski | |
| 2014/0187973 A1 | 7/2014 | Brown et al. | |
| 2014/0257115 A1 | 9/2014 | Katra et al. | |
| 2014/0276074 A1 | 9/2014 | Warner | |
| 2014/0316230 A1 | 10/2014 | Denison et al. | |
| 2014/0343595 A1 | 11/2014 | Monstadt et al. | |
| 2015/0157235 A1 | 6/2015 | Jelen et al. | |
| 2015/0359547 A1 | 12/2015 | Vale et al. | |
| 2016/0015289 A1* | 1/2016 | Simon | A61B 5/4041 600/301 |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0256130 A1 | 9/2016 | Hamilton et al. | |
| 2016/0278736 A1 | 9/2016 | Hamilton et al. | |
| 2016/0296690 A1 | 10/2016 | Kume et al. | |
| 2016/0302808 A1 | 10/2016 | Loganathan et al. | |
| 2016/0331255 A1 | 11/2016 | Cheatham, III et al. | |
| 2016/0367217 A1 | 12/2016 | Flores, II et al. | |
| 2016/0375180 A1 | 12/2016 | Anzai | |
| 2017/0007167 A1 | 1/2017 | Kostic et al. | |
| 2017/0020454 A1 | 1/2017 | Keteyian et al. | |
| 2017/0055839 A1 | 3/2017 | Levinson et al. | |
| 2017/0071495 A1 | 3/2017 | Denison et al. | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0119347 A1 | 5/2017 | Flores, II et al. | |
| 2017/0127946 A1 | 5/2017 | Levinson et al. | |
| 2017/0164963 A1 | 6/2017 | Goyal | |
| 2017/0188993 A1 | 7/2017 | Hamilton et al. | |
| 2017/0215902 A1 | 8/2017 | Leynov et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2017/0307420 A1 | 10/2017 | Flores, II et al. | |
| 2017/0319099 A1 | 11/2017 | Levinson et al. | |
| 2018/0008206 A1 | 1/2018 | Stahmann et al. | |
| 2018/0021021 A1 | 1/2018 | Zwierstra et al. | |
| 2018/0049762 A1 | 2/2018 | Seip et al. | |
| 2018/0064364 A1 | 3/2018 | Oziel et al. | |
| 2018/0084982 A1 | 3/2018 | Yamashita et al. | |
| 2018/0103927 A1 | 4/2018 | Chung et al. | |
| 2018/0116717 A1 | 5/2018 | Taff et al. | |
| 2018/0117331 A1 | 5/2018 | Kuzniecky et al. | |
| 2018/0132876 A1 | 5/2018 | Zaidat | |
| 2018/0140203 A1 | 5/2018 | Wang et al. | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0153476 A1 | 6/2018 | Annoni et al. | |
| 2018/0153477 A1 | 6/2018 | Nagale | |
| 2018/0185614 A1 | 7/2018 | Garrison et al. | |
| 2018/0220919 A1 | 8/2018 | Wershing et al. | |
| 2018/0220991 A1 | 8/2018 | O'brien et al. | |
| 2018/0243565 A1 | 8/2018 | O'Connell et al. | |
| 2018/0249967 A1 | 9/2018 | Lederman et al. | |
| 2018/0353084 A1 | 12/2018 | Wainright et al. | |
| 2019/0021627 A1 | 1/2019 | Levinson et al. | |
| 2019/0021665 A1 | 1/2019 | Kesinger et al. | |
| 2019/0046794 A1* | 2/2019 | Goodall | A61N 1/36014 |
| 2019/0051409 A1 | 2/2019 | Petrossian et al. | |
| 2019/0059850 A1 | 2/2019 | Zwierstra et al. | |
| 2019/0099132 A1 | 4/2019 | Mulinti et al. | |
| 2019/0174238 A1 | 6/2019 | Lunner et al. | |
| 2019/0175433 A1 | 6/2019 | Zwierstra et al. | |
| 2019/0200954 A1 | 7/2019 | Flores, II et al. | |
| 2019/0209128 A1 | 7/2019 | O'brien et al. | |
| 2019/0209141 A1 | 7/2019 | O'brien et al. | |
| 2019/0216433 A1 | 7/2019 | Hamilton et al. | |
| 2019/0223830 A1 | 7/2019 | Thorpe et al. | |
| 2019/0223837 A1 | 7/2019 | Petrossian et al. | |
| 2019/0282318 A1 | 9/2019 | Arant et al. | |
| 2019/0336077 A1 | 11/2019 | Kuhn et al. | |
| 2019/0357845 A1 | 11/2019 | Willis et al. | |
| 2019/0365274 A1 | 12/2019 | Wyeth et al. | |
| 2020/0000355 A1 | 1/2020 | Khair | |
| 2020/0008697 A1 | 1/2020 | Kesinger et al. | |
| 2020/0060627 A1 | 2/2020 | Karoly et al. | |
| 2020/0085255 A1 | 3/2020 | Yoo et al. | |
| 2020/0085525 A1 | 3/2020 | Zwierstra et al. | |
| 2020/0100974 A1 | 4/2020 | Hewes et al. | |
| 2020/0397355 A1 | 12/2020 | Kuhn et al. | |
| 2021/0030299 A1 | 2/2021 | Naber et al. | |
| 2021/0241908 A1 | 8/2021 | Ciupa et al. | |
| 2021/0251497 A1 | 8/2021 | Schulhauser et al. | |
| 2021/0251578 A1 | 8/2021 | Schulhauser et al. | |
| 2021/0259621 A1 | 8/2021 | Alves et al. | |
| 2021/0267465 A1 | 9/2021 | Wainwright et al. | |
| 2021/0378582 A1 | 12/2021 | Day et al. | |
| 2022/0022800 A1 | 1/2022 | Abrams et al. | |
| 2022/0061678 A1 | 3/2022 | Schulhauser et al. | |
| 2022/0061742 A1 | 3/2022 | Panken et al. | |
| 2022/0071547 A1 | 3/2022 | Revels et al. | |
| 2022/0183633 A1 | 6/2022 | Kinzie et al. | |
| 2022/0203091 A1 | 6/2022 | Vysokov | |
| 2022/0296174 A1 | 9/2022 | Kinzie et al. | |

FOREIGN PATENT DOCUMENTS

| | | |
|---|---|---|
| CN | 1891145 A | 1/2007 |
| CN | 108834398 A | 11/2018 |
| DE | 102014100133 B4 | 8/2016 |
| EP | 2319575 A1 | 5/2011 |
| EP | 3068294 A1 | 9/2016 |
| JP | 2014004219 A | 1/2014 |
| JP | 2018118132 A | 8/2018 |
| JP | 2020511173 A | 4/2020 |
| KR | 20180102877 A | 9/2018 |
| WO | 2013110001 A1 | 7/2013 |
| WO | 2013165474 A1 | 11/2013 |
| WO | 2015073903 A1 | 5/2015 |
| WO | 2015141317 A1 | 9/2015 |
| WO | 2016036946 A1 | 3/2016 |
| WO | 2017120382 A1 | 7/2017 |
| WO | 2017189623 A1 | 11/2017 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018089035 A1 | 5/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |
| WO | 2019004710 A1 | 1/2019 |
| WO | 2019094877 A1 | 5/2019 |
| WO | 2019166557 A1 | 9/2019 |
| WO | 2019177630 A1 | 9/2019 |
| WO | 2019190583 A1 | 10/2019 |
| WO | 2019195844 A1 | 10/2019 |
| WO | 2019199334 A1 | 10/2019 |
| WO | 2020144961 A1 | 7/2020 |
| WO | 2021167988 A1 | 8/2021 |
| WO | 2021181395 A1 | 9/2021 |
| WO | 2022011077 A1 | 1/2022 |
| WO | 2022020339 A1 | 1/2022 |
| WO | 2022047066 A1 | 3/2022 |
| WO | 2022047215 A1 | 3/2022 |

(56) References Cited

FOREIGN PATENT DOCUMENTS

| WO | 2022055948 A1 | 3/2022 |
| WO | 2022132938 A1 | 6/2022 |
| WO | 2022170150 A1 | 8/2022 |

OTHER PUBLICATIONS

Gasparini et al., "Hypertension, Seizures, and Epilepsy: A Review on Pathophysiology and Management," Neurological Sciences, vol. 40, No. 9, May 2019, 9 pp.

Giri et al., "Ischemic Stroke Identification Based on EEG and EOG using ID Convolutional Neural Network and Batch Normalization," ICACSIS 2016, IEEE, Oct. 15, 2016, 8 pp.

International Search Report and Written Opinion of International Application No. PCT/US2021/048037, dated Dec. 22, 2021, 14 pp.

Routray et al., "ECG Artifact Removal of EEG signal using Adaptive Neural Network," 2018 IEEE 13th International Conference on Industrial and Information Systems (ICIIS), May 27, 2019, 4 pages.

Wajngarten et al., "Hypertension and Stroke: Update on Treatment," Ischaemic Heart Disease, Stroke and Risk Factors, European Cardiology Review, May 14, 2019, pp. 111-115.

Wang et al., "Cuff-Free Blood Pressure Estimation Using Pulse Transit Time and Heart Rate," 12th International Conference on Signal Processing (ICSP), Oct. 2014, 12 pp.

Austad et al., "An Unobtrusive Wearable Device for Ambulatory Monitoring of Pulse Transit Time to Estimate Central Blood Pressure," Proceedings of the 9th International Joint Conference on Biomedical Engineering Systems and Technologies (Biostec 2016), Biodevices, vol. 2, Feb. 2016, pp. 179-186.

Fuke et al., "Blood Pressure estimation from pulse wave velocity measured on the chest," 2013 35th Annual International Conference of the IEEE, Engineering in Medicine and Biology Society (EMBC), Jul. 2013, pp. 6107-6110.

Gribbin et al., "Pulse Wave Velocity as a Measure of Blood Pressure Change," Psychophysiology, vol. 13, No. 1, Jan. 1976, pp. 86-90.

Ibrahim et al., "Exploration and Validation of Alternate Sensing Methods for Wearable Continuous Pulse Transit Time Measurement Using Optical and Bioimpedance Modalities," 2017 39th Annual International Conference of the IEEE Engineering in Medicine and Biology Society (EMBC), Jul. 2017, pp. 2051-2055.

Proenca et al., "Continuous non-occlusive blood pressure monitoring at the sternum," Biomedical Engineering/Biomedizinische Technik, vol. 57, Supplement 1, SI-1-Track-F, Aug. 2012, pp. 2-5.

Vardoulis et al., "Validation of a novel and existing algorithms for the estimation of pulse transit time," American Journal of Physiology-Heart and Circulatory Physiology, vol. 34, No. 11, Apr. 19, 2013, pp. H1558-H1567.

International Preliminary Report on Patentability from International Application No. PCT/US2021/048037 dated Feb. 28, 2023, 10 pp.

Ponciano et al., "Experimental Study for Determining the Parameters Required for Detecting ECG and EEG Related Diseases during the Timed-Up and Go Test," Computers, Aug. 27, 2020, 21 pp.

U.S. Appl. No. 17/333,199, filed May 28, 2021, and titled "Systems and Methods for Detecting Strokes".

U.S. Appl. No. 17/006,444, filed Aug. 28, 2020, and titled "Determining Composite Signals From at Least Three Electrodes".

Gibson et al., "Implantable Monitors for Early Detection of STEMI", American College of Cardiology, Apr. 23, 2019, 3 pages.

Prutchi, David, "A Device that didn't make it to market: AJ Medical's CardioAlarm to detect cardiac arrest", Posted in AJ Medical, ECG Monitoring, Museum, Posted on Feb. 13, 2019, 23 pages.

U.S. Appl. No. 17/176,504, filed Feb. 16, 2021, and titled "Systems and Methods for Detecting Strokes".

* cited by examiner

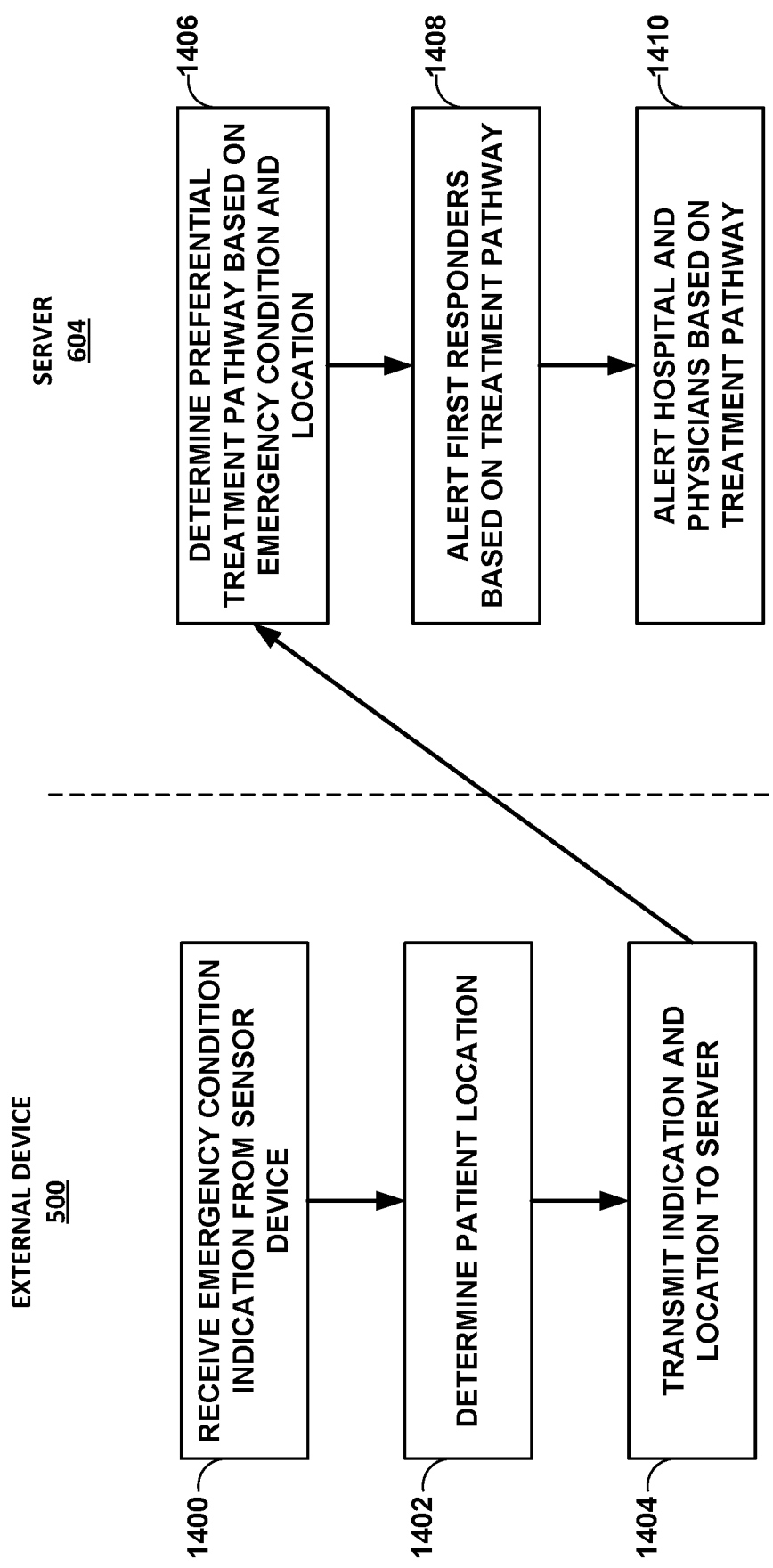

DETECTION OF PATIENT CONDITIONS USING SIGNALS SENSED ON OR NEAR THE HEAD

This application claims the benefit of U.S. Provisional Patent Application Ser. No. 63/071,997, filed Aug. 28, 2020, the entire content of which is incorporated herein by reference.

TECHNICAL FIELD

This disclosure is directed to medical devices and, more particularly, to systems and methods for detecting patient conditions.

BACKGROUND

Stroke is a serious medical condition that can cause permanent neurological damage, complications, and death. Stroke may be characterized as the rapidly developing loss of brain functions due to a disturbance in the blood vessels supplying blood to the brain. The loss of brain functions can be a result of ischemia (lack of blood supply) caused by thrombosis, embolism, or hemorrhage. The decreased blood supply can lead to dysfunction of the brain tissue in that area.

Stroke is the number two cause of death worldwide and the number one cause of disability. Speed to treatment is the critical factor in stroke treatment as 1.9 M neurons are lost per minute on average during stroke. Stroke diagnosis and time between event and therapy delivery are the primary barriers to improving therapy effectiveness. Stroke has 3 primary etiologies: i) ischemic stroke (representing approximately 65% of all strokes), ii) hemorrhagic stroke (representing approximately 10% of all strokes), and iii) cryptogenic strokes (representing approximately 25% of all strokes, and including transient ischemic attack, or TIA). Strokes can be considered as having neurogenic and/or cardiogenic origins.

A variety of approaches exist for treating patients undergoing a stroke. For example, a clinician may administer anticoagulants, such as warfarin, or may undertake intravascular interventions such as thrombectomy procedures to treat ischemic stroke. As another example, a clinician may administer antihypertensive drugs, such as beta blockers (e.g., Labetalol) and ACE-inhibitors (e.g., Enalapril) or may undertake intravascular interventions such as coil embolization to treat hemorrhagic stroke. Lastly, if stroke symptoms have resolved on their own with negative neurological work-up, a clinician may administer long-term cardiac monitoring (external or implantable) to determine potential cardiac origins of cryptogenic stroke.

Other conditions also affect humans. For example, 65 million people suffer from epilepsy worldwide, with 3.4 million people suffering from epilepsy in the United States. Epilepsy results in approximately 3,400 deaths each year in the United States alone. In some cases, patients may suffer from seizures that are misdiagnosed as epilepsy. Approximately one out of four patients who are diagnosed with epilepsy are ultimately found to have symptoms caused by a medical condition other than epilepsy, such as vasovagal syncope or a psychogenic attack. Epileptic patients may also have other conditions, as approximately one quarter of epileptic patients also suffer from cardiac arrhythmias. Treatments for epilepsy may include lifestyle changes and/or drug therapies.

SUMMARY

In general, the disclosure is directed to techniques for generating at least one of a detection, prediction, or a classification of a condition of the patient, such as stroke, seizure, vasovagal syncope, or psychogenic attacks. In some examples, the detection, prediction, or classification is generated based on sensor signals sensed by a single sensor device disposed above the shoulders of the patient, e.g., at a rear portion of a neck or skull of the patient. The techniques may include sensing both brain and cardiac signals via electrodes of the sensor device disposed above the shoulders, determining values of brain and cardiac parameters based on the respective signals, and generating the detection, prediction, or classification based on the parameters and a motion signal from a motion sensor of the sensing device.

The techniques of this disclosure may provide one or more advantages. For example, it may be beneficial for a system to be able to detect, predict, and/or classify one or more of a variety of patient conditions using brain, cardiac, and motion signals sensed via a single sensor device located above the patient's shoulders. Such a device may be relatively unobtrusive and usable for extended periods during patient daily living when compared to other devices typically employed to detect such conditions, e.g., multiple device, devices used in a clinic, or devices prescribed to provide treatment for a particular condition. The sensor device is configured to sense both brain and cardiac features from its position, and additionally sense a motion signal to further enhance its ability to detect, predict, or classify certain patient conditions. In some examples, the sensor device includes additional sensors and/or senses additional signals using the identified sensors, which may allow detection, prediction, or classification of additional conditions, and/or improve the sensitivity and specificity of algorithms used to detect, predict, or classify the conditions.

In one example, a system includes a sensor device and processing circuitry. The sensor device comprises a housing configured to be disposed above shoulders of a patient, a plurality of electrodes on the housing, a motion sensor within the housing, and sensing circuitry within the housing. The sensing circuitry is configured to sense, via the plurality of electrodes disposed above the shoulders of the patient, a brain signal and a cardiac signal of the patient. The sensing circuitry is configured to sense, via the motion sensor disposed above the shoulders of the patient, a motion signal of the patient. The processing circuitry is configured to determine values over time of one or more parameters from the brain signal, and determine values over time of one or more parameters from the cardiac signal. The processing circuitry is configured to generate at least one of a detection, prediction, or classification a condition of the patient based on the values over time of the one or more parameters from the brain signal, the values over time of the one or more one or more parameters from the cardiac signal, and the motion signal. The processing circuitry is configured to output an indication of the at least one of detection, prediction, or a classification to a computing device.

In another example a method comprises sensing, via the plurality of electrodes of a sensor device disposed above shoulders of a patient, a brain signal and a cardiac signal of the patient, and sensing, via a motion sensor of the sensor device disposed above the shoulders of the patient, a motion signal of the patient. The method further comprises determining values over time of one or more parameters from the brain signal, and determining values over time of one or more parameters from the cardiac signal. The method further comprises generating at least one of a detection, prediction, or a classification a condition of the patient based on the values over time of the one or more parameters from the brain electrical signal, the values over time of the one or more one or more parameters from the cardiac electrical signal, and the motion signal, and outputting an indication of the at least one of detection, prediction, or a classification to a computing device.

In another example, a computer readable storage medium comprises instructions that, when executed, cause processing circuitry to perform a method comprising determining values over time of one or more parameters from a brain signal sensed via a plurality of electrodes of a sensor device disposed above shoulders of a patient; determining values over time of one or more parameters from a cardiac signal sensed via a plurality of electrodes of a sensor device disposed above shoulders of a patient; generating at least one of a detection, prediction, or a classification a condition of the patient based on the values over time of the one or more parameters from the brain signal, the values over time of the one or more one or more parameters from the cardiac signal, and a motion signal sensed via a motion sensor of the sensor device disposed above the shoulders of the patient; and outputting an indication of the at least one of detection, prediction, or a classification to a computing device.

In another example, a system comprises means for performing any of the methods described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

FIG. 14 is a flow diagram illustrating an example technique for determining and implementing a preferential treatment pathway for a patient based on a generated detection, prediction, or classification of a condition of the patient.

Figure 1A:
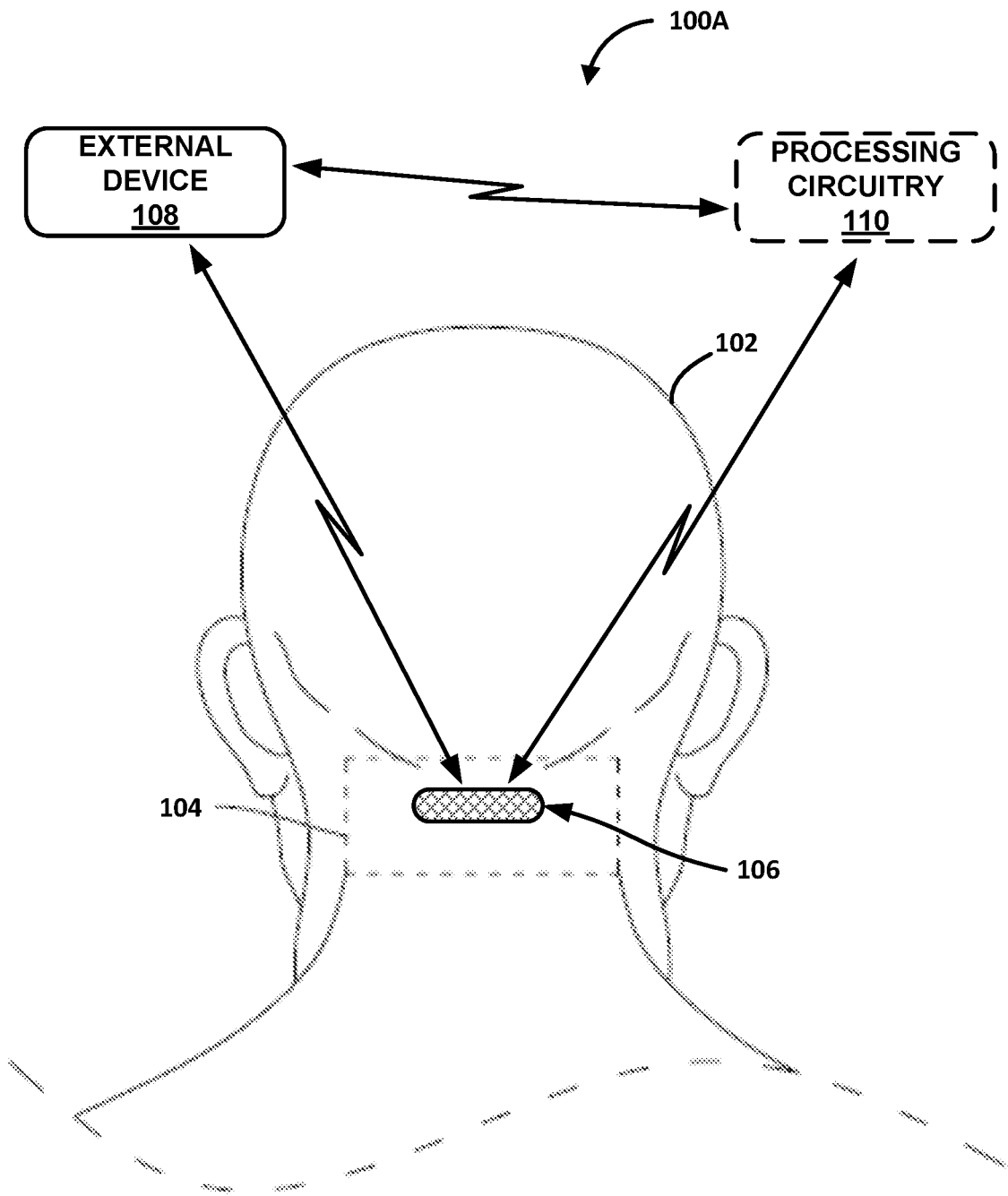
FIG. 1A is a conceptual diagram of a system configured to detect a medical condition of a patient in accordance with examples of the present disclosure.

Many aspects of the present disclosure can be better understood with reference to the following drawings. The components in the drawings are not necessarily to scale. Instead, emphasis is placed on illustrating clearly the principles of the present technology.

DETAILED DESCRIPTION

This disclosure describes various systems, devices, and techniques for detecting, predicting, and/or classifying one or more patient conditions from a device located on the head of the patient. It can be difficult to determine whether a patient is suffering or will suffer from certain conditions, such as stroke or epileptic seizure, vasovagal syncope, or psychogenic attacks. It can also be difficult to classify conditions experienced by a patient, such as between different conditions such as epileptic seizure and vasovagal syncope, between different types of a condition, such as different types or origins of strokes or seizures.

Current diagnostic techniques typically involve evaluating a patient for visible symptoms, such as paralysis or numbness of the face, arm, or leg, as well as difficultly walking, speaking, or understanding in the case of stroke. Visible stroke indicators are abbreviated as F.A.S.T.: face, arm, and speech-time to call 9-1-1. However, these techniques may result in undiagnosed strokes, particularly more minor strokes that leave patients relatively functional upon cursory evaluation. Even for relatively minor strokes, it is important to treat the patient as soon as possible because treatment outcomes for stroke patients are highly time-dependent. Accordingly, there is a need for improved methods for detecting strokes. However, such treatments may be frequently underutilized and/or relatively ineffective due to the failure to timely identify whether a patient is undergoing or has recently undergone a stroke. This is a particular risk with more minor strokes that leave patients relatively functional upon cursory evaluation.

Similarly, it can be difficult to detect or identify seizures, such as seizures that occur in patients with epilepsy. Some patients exhibit physical manifestations of the epileptic seizure, such as jerking movements of the arms and legs, other symptoms of an epileptic seizure may include temporary confusion, staring, loss of consciousness or awareness, or emotional symptoms such as fear, anxiety, or déjàvu. When patients are experiencing an epileptic seizure, the patient may not be able to understand the symptoms or accurately identify what occurred. Moreover, the patient may not be able to obtain or ask for intervention, such as medication. In some examples, a deep brain stimulation (DBS) device may detect an epileptic seizure and provide electrical stimulation via electrodes implanted within the brain to prevent or reduce symptoms of seizure. However, such DBS devices require an invasive implantation procedure and may not be appropriate for screening or diagnosis of the patient.

As described herein, a sensor device may be used to detect, predict, and/or classify patient conditions from a location on or near the head of the patient. The sensor device may be configured to be implanted subcutaneously or positioned externally (e.g., worn) on the patient without the need for any medical leads. In some examples, instead of leads, the sensor device may include a housing that carries multiple electrodes directly on the housing, and one or more other sensors on or within the housing. Using the housing electrodes, the sensor device may sense electrical signals from one or more vectors, and processing circuitry may determine values physiological parameters representative of patient condition. The signals and parameters may be indicative of brain activity and/or activity of other organs such as the heart. Based on the parameter values, the processing circuitry may detect, predict, and/or classify patient conditions. The processing circuitry may output an indication of the detection, prediction, and/or classification to a computing device, e.g., to facilitate a treatment or intervention.

Conventional electroencephalogram (EEG) electrodes are typically positioned over a large portion of a user's scalp. While electrodes in this region are well positioned to detect electrical activity from the patient's brain, there are certain drawbacks. Sensors in this location interfere with patient movement and daily activities, making them impractical for prolonged monitoring. Additionally, implanting traditional electrodes under the patient's scalp is difficult and may lead to significant patient discomfort. To address these and other shortcomings of conventional EEG sensors, sensor devices according to technology described herein sense electrical signals from a smaller region near or on the patient's head, such as adjacent a rear portion of the patient's neck or the patient's skull or near the patient's temple(s). In these positions, implantation under the patient's skin is relatively simple, and a temporary application of a wearable sensor device (e.g., coupled to a bandage, garment, band, or adhesive member) does not unduly interfere with patient movement and activity. Although primarily described in the context of leadless sensor devices, in some examples, e.g., as described with respect to FIGS. 2I-2N, 2P, and 2Q, a sensor device may include electrode extensions. The electrode extensions may increase a size of a vector for sensing signals via the electrodes, such as brain and cardiac signals, and/or may position electrodes closer to a source of the brain and cardiac signals, which may enhance the sensitivity of algorithms using such signals to detect and/or predict patient conditions.

EEG signals detected via electrodes disposed at or adjacent the back of a patient's neck may include other signals and relatively high noise amplitude. For example, the electrical signals associated with brain activity may be intermixed with electrical signals associated with cardiac activity (e.g., electrocardiogram (ECG) signals or signals including components associated with mechanical activity of the heart) and muscle activity (e.g., electromyogram (EMG) signals) and artifacts from other electrical sources such as patient movement or external interference. Accordingly, in some examples, the signals may be filtered or otherwise manipulated to separate the brain activity data (e.g., EEG signals) and cardiac electrical signals (e.g., ECG or other cardiac signals) from each other and other electrical signals (e.g., EMG signals, etc.). A sensor device of this disclosure may include multiple electrodes having non-parallel vector axes for sensing differential signals, and circuitry in the device may be configured to generate signals, such as a cardiac signal and a brain signal, based on the differential signals.

As described in more detail below, the parameter values may be analyzed to detect, predict, or classify one or more conditions based on one or more thresholds, correlation between signals, or using a classification algorithm, which can itself be derived using machine learning techniques applied to databases of patient data known to represent the conditions or classifications. The detection algorithm(s) can be passive (involving measurement of a purely resting patient) or active (involving prompting a patient to perform potentially impaired functionality, such as moving particular muscle groups (e.g., raising an arm, moving a finger, moving facial muscles, etc.,) and/or speaking while recording the electrical response), or from an electrical or other stimulus.

Aspects of the technology described herein can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, or a short-range radio network, such as via Bluetooth). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1A is a conceptual diagram of a system 100A configured to detect a medical condition of a patient in accordance with examples of the present disclosure. The example techniques described herein may be used with a sensor device 106, which in the illustrated example is an implantable medical device (IMD), and which may be in wireless communication with at least one of external device 108, processing circuitry 110, and other devices not pictured in FIG. 1A. For example, an external device (not illustrated in FIG. 1A) may include at least a portion of processing circuitry 110.

As shown in FIG. 1A, sensor device 106 is located in target region 104. Target region 104 can be a rear portion of a user's neck or a rear portion of the skull. In other examples, target region may be located at other positions of patient, such as near the user's temple(s) (e.g., above the ear(s)) and/or over the temporal portion of the skull. Although sensor device 106 may be implanted at a location generally centered with respect to the head, neck, or target region 104, sensor device 106 may be implanted in an off-center location in order to obtain desired vectors from the electrodes carried on the housing of sensor device 106. Sensor device 106 can be disposed in target region 104 either via implantation (e.g., subcutaneously) or by being placed over the patient's skin with one or more electrodes of sensor device 106 being in direct contact with the patient's skin at or adjacent the target region 104.

While conventional EEG electrodes are placed over the patient's scalp and ECG electrodes are positioned elsewhere on the patient's body, the present technology advantageously enables recording of clinically useful brain activity and cardiac activity signals via electrodes positioned at the target region 104 at the rear of the patient's neck or head, or other cranial locations, such as temporal locations, described herein. This anatomical area is well suited to suited both to implantation of sensor device 106 and to temporary placement of a sensor device over the patient's skin. In contrast, conventional EEG electrodes positioned over the scalp are cumbersome, and implantation over the patient's skull is challenging and may introduce significant patient discomfort.

As noted elsewhere here, conventional EEG electrodes are typically positioned over the scalp to more readily achieve a suitable signal-to-noise ratio for detection of brain activity. However, by using certain digital signal processing, and a special-purpose classifier algorithm, clinically useful brain activity and cardiac activity signals can be obtained using electrodes disposed at the target region 104. Specifically, the electrodes can detect electrical activity that corresponds to brain activity in the P3, Pz, and/or P4 regions (as shown in FIG. 1C).

Processing circuitry 110 may extract values of one or more parameters, e.g., features, from signals indicative of brain activity and/or cardiac activity. Processing circuitry 110 may then determine whether or not the patient has experienced (or has a supra-threshold risk of experiencing) a stroke, epileptic seizure, or other condition based on these parameter value. In some examples, sensor device 106 takes the form of a LINQ™ Insertable Cardiac Monitor (ICM), available from Medtronic plc, of Dublin, Ireland, or a device has a similar implant volume and similar sensing capabilities. The example techniques may additionally, or alternatively, be used with a medical device not illustrated in FIG. 1A such as another type of IMD, a patch monitor device, a wearable device (e.g., smart watch), or another type of external medical device.

Clinicians sometimes diagnose a patient (e.g., patient 102) with medical conditions and/or determine whether a condition of patient 102 is improving or worsening based on one or more observed physiological signals collected by physiological sensors, such as electrodes, optical sensors, chemical sensors, temperature sensors, acoustic sensors, and motion sensors. In some cases, clinicians apply non-invasive sensors to patients in order to sense one or more physiological signals while a patent is in a clinic for a medical appointment. However, in some examples, events that may change a condition of a patient, such as administration of a therapy, may occur outside of the clinic. As such, in these examples, a clinician may be unable to observe the physiological markers needed to determine whether an event, such as a seizure or stroke, has changed a medical condition of the patient and/or determine whether a medical condition of the patient is improving or worsening while monitoring one or more physiological signals of the patient during a medical appointment. In the example illustrated in FIG. 1A, sensor device 106 is implanted within or attached to patient 102 to continuously record one or more physiological signals of patient 102 over an extended period of time.

In some examples, sensor device 106 includes a plurality of electrodes. Sensor device 106 may sense brain activity and heart activity signals, as well as other signals such as impedance signals for respiration, skin impedance, and perfusion, in some examples. Moreover, sensor device 106 may additionally or alternatively include one or more optical sensors, accelerometers or other motion sensors, temperature sensors, chemical sensors, light sensors, pressure sensors, and acoustic sensors, in some examples. Such sensors may sense various signals that may improve the ability of processing circuitry 110 to detect, predict, or classify patient conditions.

External device 108 may be a hand-held computing device with a display viewable by the user and an interface for providing input to external device 108 (e.g., a user input mechanism). For example, external device 108 may include a small display screen (e.g., a liquid crystal display (LCD) or a light emitting diode (LED) display) that presents information to the user. In addition, external device 108 may include a touch screen display, keypad, buttons, a peripheral pointing device, voice activation, or another input mechanism that allows the user to navigate through the user interface of external device 108 and provide input. If external device 108 includes buttons and a keypad, the buttons may be dedicated to performing a certain function, e.g., a power button, the buttons and the keypad may be soft keys that change in function depending upon the section of the user interface currently viewed by the user, or any combination thereof.

In other examples, external device 108 may be a larger workstation or a separate application within another multi-function device, rather than a dedicated computing device. For example, the multi-function device may be a notebook computer, tablet computer, workstation, one or more servers, cellular phone, personal digital assistant, or another computing device that may run an application that enables the computing device to operate as a secure device. In some examples, external device 108 is a smartphone of patient 102 and/or a watch or other wearable computing device, which may communicate with sensor device 106, e.g., via Bluetooth™. In some examples, external device 108 is configured to communicate with a computer network, such as the Medtronic CareLink® Network developed by Medtronic, plc, of Dublin, Ireland.

Processing circuitry 110, in some examples, may include one or more processors that are configured to implement functionality and/or process instructions for execution within IMD 106. For example, processing circuitry 110 may be capable of processing instructions stored in a storage device. Processing circuitry 110 may include, for example, microprocessors, graphical processing units (GPUs), tensor processing units (TPUs), digital signal processors (DSPs), application specific integrated circuits (ASICs), field-programmable gate arrays (FPGAs), or equivalent discrete or integrated logic circuitry, or a combination of any of the foregoing devices or circuitry. Accordingly, processing circuitry 110 may include any suitable structure, whether in hardware, software, firmware, or any combination thereof, to perform the functions ascribed herein to processing circuitry 110.

Processing circuitry 110 may represent processing circuitry located within any one or both of sensor device 106 and external device 108. In some examples, processing circuitry 110 may be entirely located within a housing of sensor device 106. In other examples, processing circuitry 110 may be entirely located within a housing of external device 108. In other examples, processing circuitry 110 may be located within any one or combination of sensor device 106, external device 108, and another device or group of devices that are not illustrated in FIG. 1A. As such, techniques and capabilities attributed herein to processing circuitry 110 may be attributed to any combination of sensor device 106, external device 108, and other devices that are not illustrated in FIG. 1A.

Medical device system 100A of FIG. 1A is an example of a system configured to sense signals and generate detections, predictions, or classifications of patient conditions according to one or more techniques of this disclosure. In some examples, the sensed signals may include features representative of heart function such as depolarizations and repolarizations of the heart, or contractions of the heart. Information relating to the aforementioned events, such as time separating one or more of the events, may be applied by processing circuitry 110 for a number of purposes. Processing circuitry 110 may perform signal processing techniques to extract information indicating the one or more parameters of the cardiac signal. In some examples, the sensed electrical signals may include features representative of brain function, such as amplitudes of frequencies in one or more frequency bands, such as alpha bands, beta bands, or gamma bands. Processing circuitry 110 may perform various signal processing to extract these brain features from the sensed electrical signals. In some examples, the sensed signals may be surrogates for brain and cardiac electrical signals (e.g., EEG or ECG signals). Pulsatile signals sensed from the scalp vasculature correspond to ventricular contractions and ECG R-waves, albeit with a slight timing delay.

In some examples, sensor device 106 includes one or more accelerometers or other motion sensors. An accelerometer of sensor device 106 may collect an accelerometer signal which reflects a measurement of any one or more of a motion of patient 102, a posture of patient 102 and a body angle of patient 102. In some cases, the accelerometer may collect a three-axis accelerometer signal indicative of patient 102's movements within a three-dimensional Cartesian space. For example, the accelerometer signal may include a vertical axis accelerometer signal vector, a lateral axis accelerometer signal vector, and a frontal axis accelerometer signal vector. The vertical axis accelerometer signal vector may represent an acceleration of patient 102 along a vertical axis, the lateral axis accelerometer signal vector may represent an acceleration of patient 102 along a lateral axis, and the frontal axis accelerometer signal vector may represent an acceleration of patient 102 along a frontal axis. In some cases, the vertical axis substantially extends along a torso of patient 102 when patient 102 from a neck of patient 102 to a waist of patient 102, the lateral axis extends across a chest of patient 102 perpendicular to the vertical axis, and the frontal axis extends outward from and through the chest of patient 102, the frontal axis being perpendicular to the vertical axis and the lateral axis.

Sensor device 106 may measure other signals such as an impedance (e.g., subcutaneous impedance measured via electrodes depicted in FIGS. 2A-2N, 2P, and 2Q) which may indicate respiration, skin impedance, or prefusion, heart sound signals, ballistocardiogram signals, pressure signals, or the like. Processing circuitry 110 may analyze any one or more of the set of parameters in order to determine whether or not patient 102 is experiencing or has a supra-threshold risk of experiencing a conditions, such as stroke or seizure. In some examples, pulsatile signals sensed optically or mechanically, e.g., via the electrodes, an optical sensor, accelerometer, pressure sensor, impedance sensor, or heart sound sensor, from the scalp vasculature may provide a surrogate for an ECG or other cardiac electrical activity signal.

In some examples, one or more sensors (e.g., electrodes, motion sensors, optical sensors, temperature sensors, pressure sensors, or any combination thereof) of sensor device 106 may generate a signal that indicates a parameter of a patient. In some examples, the signal that indicates the parameter includes a plurality of parameter values, where each parameter value of the plurality of parameter values represents a measurement of the parameter at a respective interval of time. The plurality of parameter values may represent a sequence of parameter values over time, where each parameter value of the sequence of parameter values are collected by sensor device 106 for each time interval of a sequence of time intervals. For example, sensor device 106 may perform a parameter measurement in order to determine a parameter value of the sequence of parameter values according to a recurring time interval (e.g., every day, every night, every other day, every twelve hours, every hour, every second, or any other recurring time interval). In this way, sensor device 106 may be configured to track a respective patient parameter more effectively as compared with a technique in which a patient parameter is tracked during patient visits to a clinic, since sensor device 106 is implanted within patient 102 and is configured to perform parameter measurements according to recurring time intervals without missing a time interval or performing a parameter measurement off schedule.

Sensor device 106 may be referred to as a system or device. In one example, sensor device 106 may include a plurality of electrodes carried by the housing of sensor device 106, sensing circuitry configured to sense, via at least two electrodes of the plurality of electrodes, electrical signals from patient 10, and a motion sensor, e.g., accelerometer, configured to sense a motion signals of the patient. Sensor device 106 may also include processing circuitry 110. The housing of sensor device 106 carries the plurality of electrodes and contains, or houses, the sensing circuitry, the processing circuitry, the motion sensor, and any other sensors. In this manner, sensor device 106 may be referred to as a leadless sensing device because the electrodes are carried directly by the housing instead of by any leads that extend from the housing. In some examples, however, sensor device 106 may include one or more sensing leads extending therefrom and into the tissue of the patient; such lead(s) may be employed instead of or in addition to the electrodes of sensor device 106 (e.g., such as electrode extensions depicted in FIG. 2I-2N, 2P, 2Q), and may perform any of the functions attributed herein to the electrodes.

The signals sensed by sensing device 106 can include brain signals and/or heart signals. In some examples, the plurality of electrodes are configured to detect brain signals corresponding to activity in at least one of a P3, Pz, or P4 brain region, which is at the back of the head or upper neck region as shown in FIG. 1C. In this manner, the housing of sensor device 106 may be configured to be disposed at or adjacent a rear portion of a neck or skull of patient 102. The housing of sensor device 106 may be configured to be implanted within patient 102, such as implanted subcutaneously. In other examples, the housing of sensor device 106 may be configured to be disposed on an external surface of skin of patient 102.

In some examples, sensor device 106 may include a single sensing circuitry configured to generate, from the sensed electrical signals, information that includes both the brain activity data (e.g., electroencephalogram (EEG) data) and the heart activity data (e.g., ECG data or cardiac contraction data). In other examples, the processing circuitry of sensor device 106 may include separate hardware that generates different information from the sensed electrical signals. For example, IMD 106 may include first circuitry configured to generate the brain activity from the electrical signals and second circuitry different from the first circuitry and configured to generate the heart activity data from the electrical signals. Even with the first and second circuitry configured to generate different information, or data, in some examples, sensed electrical signals may be conditioned or processed by one or more electrical components (e.g., filters or amplifiers) prior to being processed by the first and second circuitry. In some examples, parameters determined from brain activity signals data may include features, such as spectral features, indicative of the strength of signals in various frequency bands or at various frequencies.

In some examples, sensor device 106 may include one or more accelerometers or other motion sensors within the housing. The accelerometer may be configured to generate motion data representative of motion of patient 102. Processing circuitry 110 may then be configured to generate the detection, prediction, or classification of one or more conditions based on the motion signal, e.g., in condition with the parameter values determined from the brain and cardiac signals. For example, body motion, or lack thereof, may be indicative of a type of seizure experienced by patient 102. As another example, certain body motions or behaviors (e.g., patterns of motion) may be indicative of stroke. In one example, the processing circuitry 110 may be configured to determine, based on the motion data, that patient 102 has fallen, or has nearly fallen. In response to determining that patient 102 has fallen, the processing circuitry 110 may be configured to inform or modify an algorithm for detecting or predicting stroke or another patent condition. In some examples, stroke may cause a patient to fall. Therefore, in combination with other features extracted from sensed brain and cardiac signals, processing circuitry 110 may determine from the fall indication that the stroke metric indicates detection of a stroke. In other examples, sensor device 106 or processing circuitry 110 may determine that a characteristic of the motion data exceeds a threshold. The threshold may be an acceleration value indicative of a fall, for example. For seizure, as another example, a frequency of the motion exceeding a frequency threshold may be indicative of body movement from a seizure.

Processing circuitry 110 may extract various features from the cardiac signal sensed by sensor device 106, e.g., an ECG signal or signal representative of cardiac mechanical activity, such as heart rate, heart rate variability, etc. Such cardiac parameters may indicate an autonomic activity state of patient, and may inform the detection, prediction, and/or classification of a variety of patient conditions. For example, processing circuitry 110 may classify a seizure as one of a plurality of seizure types based on such parameters. For example, seizure types may include single seizure, stroke induced seizure, epileptic seizure, non-epileptic episodes (such as VVS or psychogenic attacks), absence seizures, tonic-clonic or convulsive seizures, atonic seizures, clonic seizures, tonic seizures, and myoclonic seizures. In some examples, processing circuitry 110 may also determine the seizure type based on accelerometer data, temperature data, or any other parameter extracted from one or more sensors.

Figure 1B:
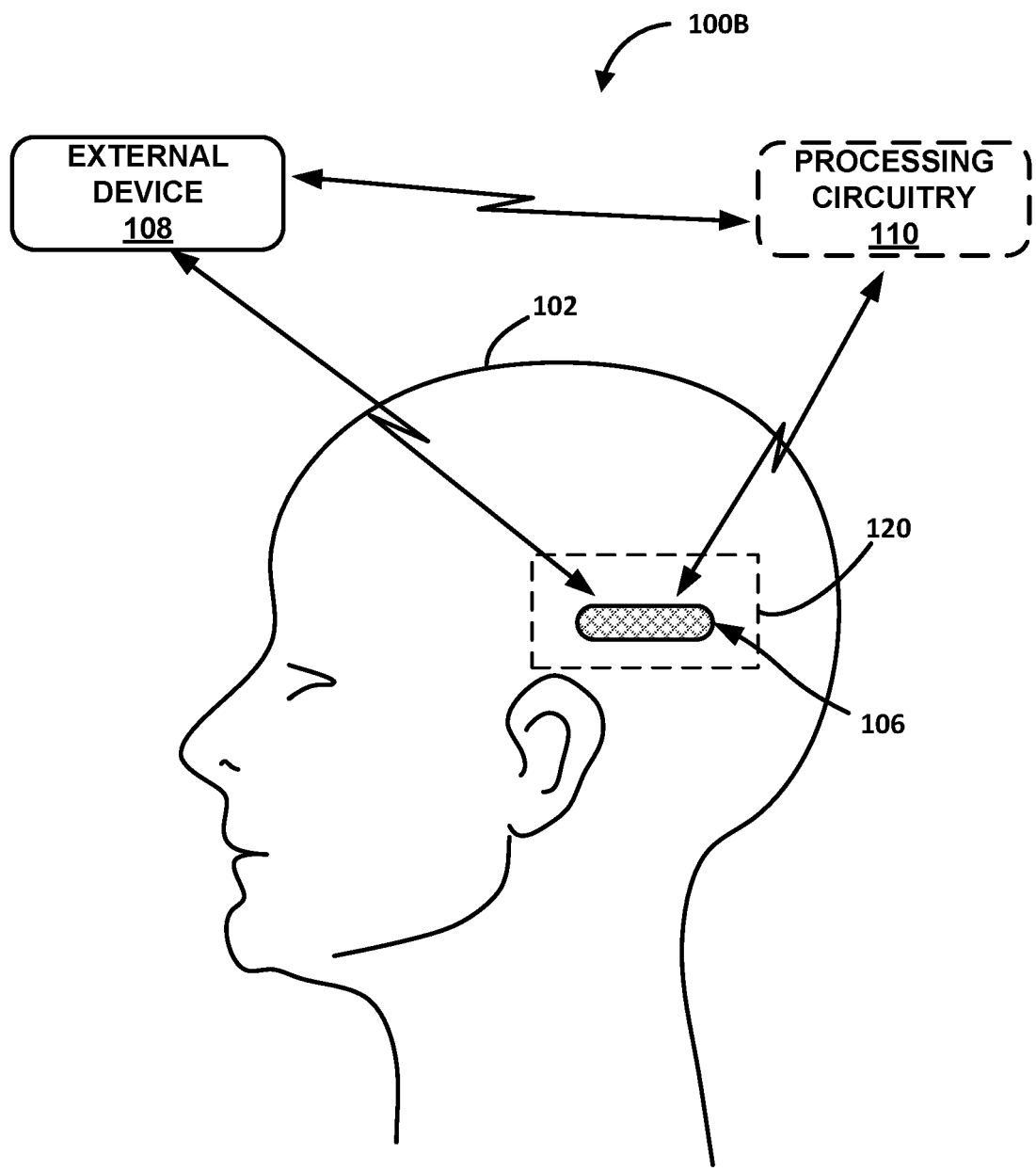
FIG. 1B is a conceptual diagram of another system configured to detect a medical condition of a patient in accordance with examples of the present disclosure.
Figure 1C:
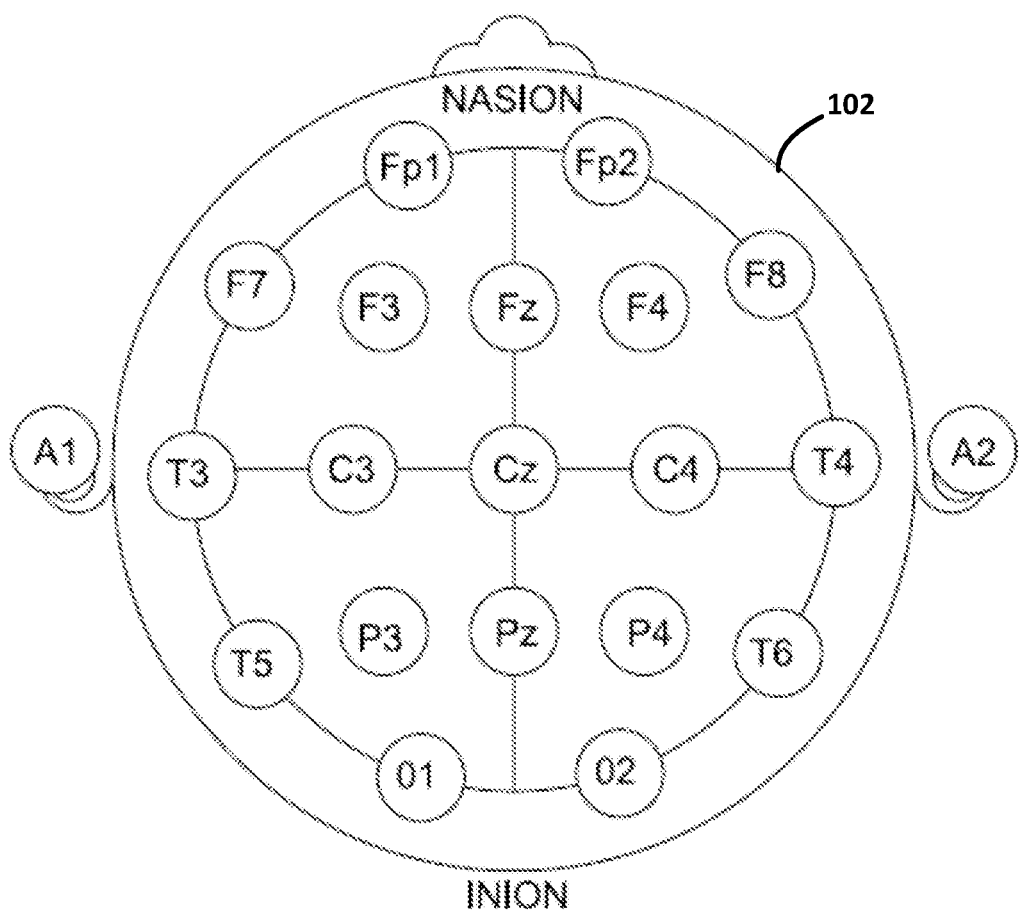
FIG. 1C is a diagram of the 10-20 map for electroencephalography (EEG) sensor measurements.

FIG. 1B is a conceptual diagram of a system 100B configured to detect a medical condition of patient 102 in accordance with examples of the present disclosure. System 100B may be substantially similar to system 100A of FIG. 1A. However, sensor device 106 of system 100B may be configured to be implanted in target region 120 which is located on the side of the head posterior of the temple of patient 102, e.g., above the ear and/or over the temporal portion of the cranium. Sensor device 106 implanted at target region 120 may be configured to sense cardiac and brain signals, as well as other sensor signals described herein, in this area. In such examples, the electrodes of sensor device 106 may detect electrical activity that corresponds to brain activity in the T3 region (as shown in FIG. 1C), or T4 region if implanted on the other side of the patient's head, or both of two or more sensor devices are implanted bilaterally at temporal regions. In some examples, sensor device 106 may need to employ different filters or other processing or signal conditioning techniques than those at target region 104 due to different types of noise at target region 120, such as muscle activity due to mandible movement or other types of electrical activity. In other examples, sensor device 106 may be configured to sense signals as described herein from other areas of the head of patient 102 that may be outside of target regions 104 and 120.

FIG. 1C is a diagram of the 10-20 map for EEG sensor measurements. As shown in FIG. 1C, various locations on the head of patient 102 may be targeted using the electrodes carried by sensor device 106. At the back of the head, such as in target region 104 of FIG. 1A, sensor device 106 may sense electrical signals at least one of P3, Pz or P4 At the side of the head, such as in target region 120 of FIG. 1B, sensor device 106 may sense electrical signals at least one of F7, T3, or T5 and/or at one or more of F8, T4, or T6.

Figure 2A:
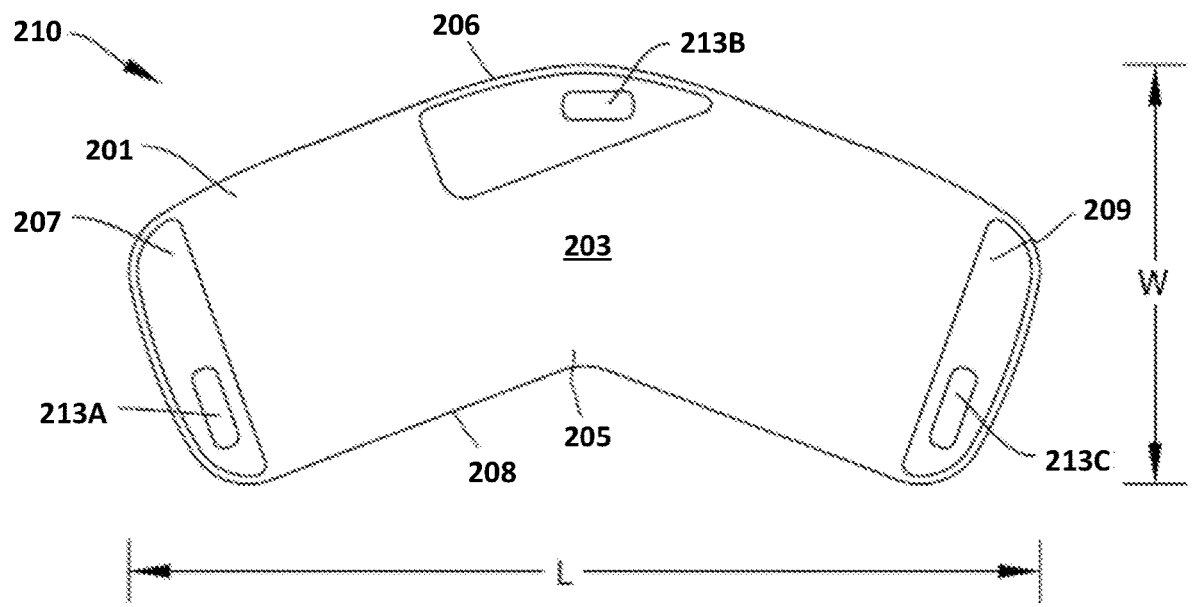
FIG. 2A depicts a top view of a sensor device in accordance with examples of the present disclosure.
Figure 2B:
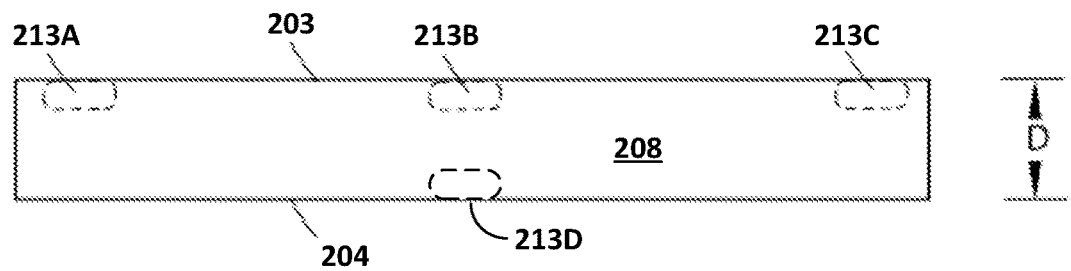
FIG. 2B depicts a side view of the sensor device shown in FIG. 2A in accordance with examples of the present disclosure.

FIG. 2A depicts a top view of a sensor device 210 (e.g., an IMD) in accordance with examples of this disclosure. FIG. 2B depicts a side view of sensor device 210 shown in FIG. 2A. In some examples, sensor device 210 can include some or all of the features of, and be similar to, sensor device 106 described above with respect to FIGS. 1A and 1B and/or the sensor devices 310, 360B, 360B, 361, or 400 described below with respect to FIGS. 3A-3D and 4, and can include additional features as described in connection with FIG. 2A. In the illustrated example, sensor device 210 includes a housing 201 that carries a plurality of electrodes 213A, 213B, 213C, and 213D (collectively "electrodes 213") therein. Although four electrodes are shown for sensor device 210, in other examples, only two or three electrodes, or more than four electrodes may be carried by housing 201. As shown in FIG. 2H, any of the electrodes may be segmented; that is, each electrode may include two conductive portions separated by an insulative material. In some examples, a first portion of each electrode may be configured to sense ECG signals or other cardiac signals, and a second portion may be configured to sense EEG signals.

In operation, electrodes 213 can be placed in direct contact with tissue at the target site (e.g., with the user's skin if placed over the user's skin, or with subcutaneous tissue if the sensor device 210 is implanted). Housing 201 additionally encloses electronic circuitry located inside the sensor device 210 and protects the circuitry (e.g., processing circuitry, sensing circuitry, communication circuitry, sensors, and a power source) contained therein from body fluids. In various examples, electrodes 213 can be disposed along any surface of the sensor device 210 (e.g., anterior surface, posterior surface, left lateral surface, right lateral surface, superior side surface, inferior side surface, or otherwise), and the surface in turn may take any suitable form.

In the example of FIGS. 2A and 2B, housing 201 can be a biocompatible material having a relatively planar shape including a first major surface 203 configured to face towards the tissue of interest (e.g., to face anteriorly when positioned at the back of the patient's neck) a second major surface 204 opposite the first, and a depth D or thickness of housing 201 extending between the first and second major surfaces. Housing 201 can define a superior side surface 206 (e.g., configured to face superiorly when sensing device 210 is implanted in or at the patient's head or neck) and an opposing inferior side surface 208. Housing 201 can further include a central portion 205, a first lateral portion (or left portion) 207, and a second lateral portion (or right portion) 209. Electrodes 213 are distributed about housing 201 such that a central electrode 213B is disposed within the central portion 205 (e.g., substantially centrally along a horizontal axis of the device), a back electrode 213D is disposed on inferior side surface, a left electrode 213A electrode is disposed within the left portion 207, and a right electrode 213C is disposed within the right portion 209. As illustrated, housing 201 can define a boomerang or chevron-like shape in which the central portion 205 includes a vertex, with the first and second lateral portions 207 and 209 extending both laterally outward and from the central portion 205 and also at a downward angle with respect to a horizontal axis of the device. In other examples, housing 201 may be formed in other shapes which may be determined by desired distances or angles between different electrodes 213 carried by housing 201.

The configuration of housing 201 can facilitate placement either over the user's skin in a wearable or bandage-like form or for subcutaneous implantation. As such, a relatively thin housing 201 can be advantageous. Additionally, housing 201 can be flexible in some embodiments, so that housing 201 can at least partially bend to correspond to the anatomy of the patient's neck (e.g., with left and right lateral portions 207 and 209 of housing 201 bending anteriorly relative to the central portion 205 of housing 201).

In some embodiments, housing 201 can have a length L of from about 15 to about 50 mm, from about 20 to about 30 mm, or about 25 mm. Housing 201 can have a width W from about 2.5 to about 15 mm, from about 5 to about 10 mm, or about 7.5 mm. In some embodiments, housing 201 can have a thickness of the thickness is less than about 10 mm, about 9 mm, about 8 mm, about 7 mm, about 6 mm, about 5 mm, about 4 mm, or about 3 mm. In some embodiments, the thickness of housing 201 can be from about 2 to about 8 mm, from about 3 to about 5 mm, or about 4 mm. Housing 201 can have a volume of less than about 1.5 cc, about 1.4 cc, about 1.3 cc, about 1.2 cc, about 1.1 cc, about 1.0 cc, about 0.9 cc, about 0.8 cc, about 0.7 cc, about 0.6 cc, about 0.5 cc, or about 0.4 cc. In some embodiments, housing 201 can have dimensions suitable for implantation through a trocar introducer or any other suitable implantation technique.

As illustrated, electrodes 213 carried by housing 201 are arranged so that all three electrodes 213 do not lie on a common axis. In such a configuration, electrodes 213 can achieve a variety of signal vectors, which may provide one or more improved signals, as compared to electrodes that are all aligned along a single axis. This can be particularly useful in a sensor device 210 configured to be implanted at the neck or head while detecting electrical activity in the brain and the heart. In some examples, processing circuitry may create virtual signal vectors through a weighted sum or two or more physical signal vectors, such as the physical signal vectors available from electrodes 213 of sensor device 210 or the electrodes of any other sensor device described herein.

In some examples, all electrodes 213 are located on the first major surface 203 and are substantially flat and outwardly facing. However, in other examples one or more electrodes 213 may utilize a three-dimensional configuration (e.g., curved around an edge of the device 210). Similarly, in other examples, such as that illustrated in FIG. 2B, one or more electrodes 213 may be disposed on the second major surface opposite the first. The various electrode configurations allow for configurations in which electrodes 213 are located on both the first major surface and the second major surface. In other configurations, such as that shown in FIG. 2B, electrodes 213 are only disposed on one of the major surfaces of housing 201. Electrodes 213 may be formed of a plurality of different types of biocompatible conductive material (e.g., titanium nitride or platinum iridium), and may utilize one or more coatings such as titanium nitride or fractal titanium nitride. In some examples, the material choice for electrodes can also include materials having a high surface area (e.g., to provide better electrode capacitance for better sensitivity) and roughness (e.g., to aid implant stability). Although the example shown in FIGS. 2A and 2B includes four electrodes 213, in some embodiments the sensor device 210 can include 1, 2, 3, 4, 5, 6, or more electrodes carried by housing 201.

Figure 2C:
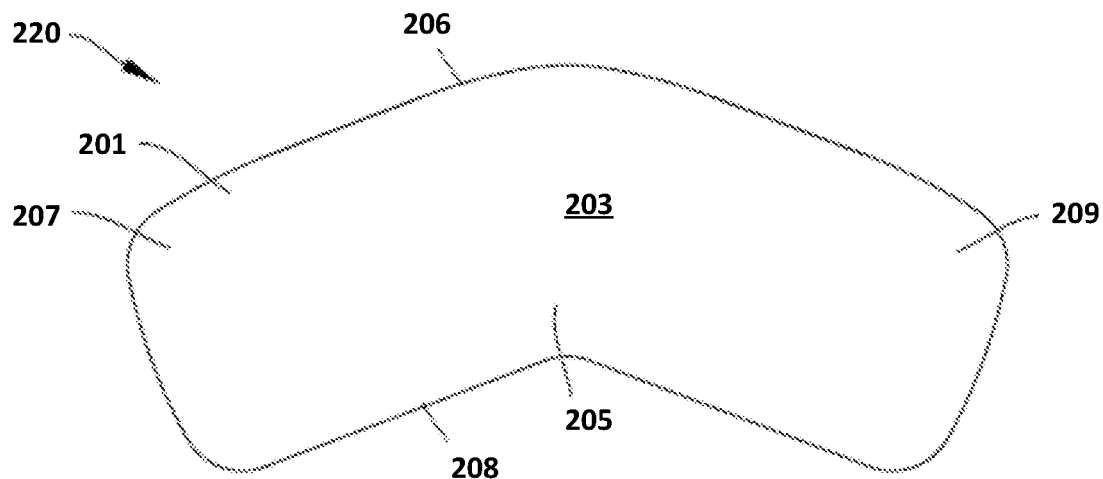
FIG. 2C depicts a top view of another example sensor device in accordance with examples of the present disclosure.

FIG. 2C depicts a top view of another example sensor device 220 in accordance with the present technology. FIG.

Figure 2D:
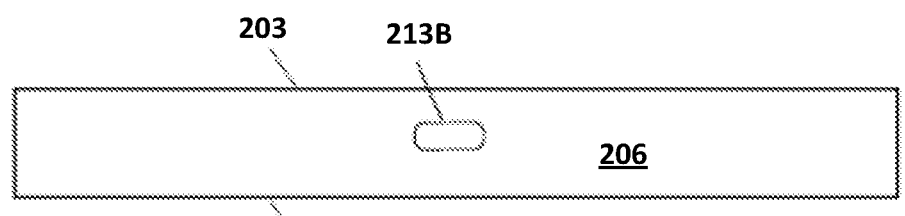
FIG. 2D depicts a side view of another example sensor device in accordance with examples of the present disclosure.
Figure 2E:
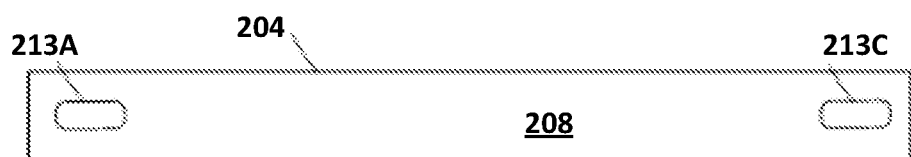
FIG. 2E depicts a side view of another example sensor device in accordance with examples of the present disclosure.
Figure 2F:
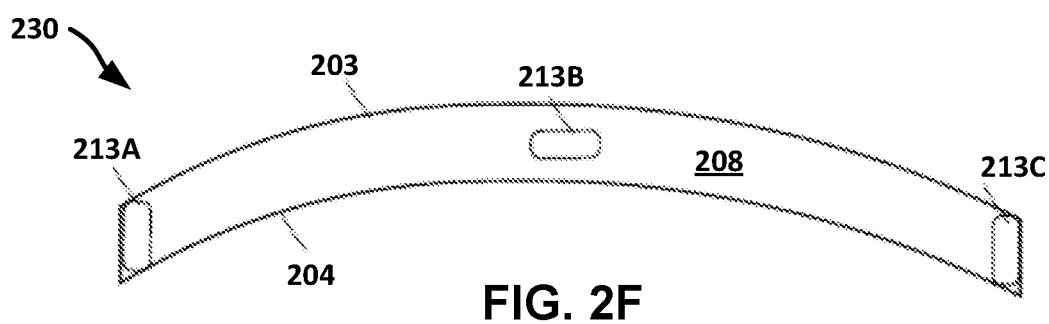
FIG. 2F depicts a side view of another example sensor device in accordance with examples of the present disclosure.

2C illustrates sensor device 220 which is substantially similar to sensor device 210, but sensor device 220 includes electrodes 213 which are not exposed along the first major surface 203 of housing 201. Instead, electrodes 213 can be exposed along superior and inferior side surfaces (e.g., facing superiorly and inferiorly when implanted at or on a patient's neck), as shown in FIGS. 2D and 2E. FIG. 2F illustrates sensor device 230 which is substantially similar to sensor devices 210 and 220, but housing 201 is constructed to have a curved configuration, and in which the electrodes can be place along the superior and/or inferior side surfaces of housing 201. In some embodiments, a curved configuration can improve patient comfort and more readily conform to the anatomy of the patient's neck region. In some examples, any of sensor devices 210, 220, or 230 may be flexible in order to conform to the anatomy of the patient at the desired implant or external surface location. Additionally, examples that include electrode extensions, e.g., as depicted in FIGS. 2I-2N, 2P, and 2Q, are inherently flexible, allowing conformance to neck and/or cranial anatomy. In some examples, sensor device 220 and/or sensor device 230 may be implanted at a location generally centered with respect to the thorax, the head, e.g., back or temporal regions, neck, or another target region. In some examples, sensor device 220 and/or sensor device 230 may be placed on an external surface of skin of a patient.

In operation, electrodes 213 are used to sense signals (e.g., EEG or other brain signals and/or ECG or other heart signals) which may be submuscular or subcutaneous. The sensed signals may be stored in a memory of the sensor device, and signal data may be transmitted via a communications link to another device (e.g., external device 108 of FIG. 1A). The sensed signals may be time-coded or otherwise correlated with time data, and stored in this form, so that the recency, frequency, time of day, time span, or date(s) of a particular signal data point or data series (or computed measures or statistics based thereon) may be determined and/or reported. In some examples, electrodes 213 may additionally or alternatively be used for sensing any biopotential signal of interest, such as an EMG or a nerve signal, as well as impedance signals, from any implanted or external location. These signals may be time-coded or time-correlated, and stored in that form, in the manner described above with respect to brain and cardiac signal data.

Figure 2G:
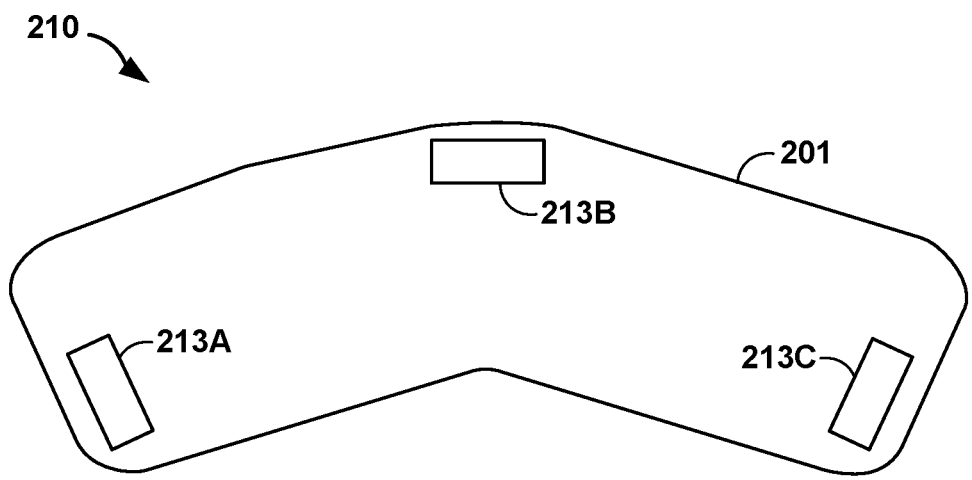
FIG. 2G depicts a top view of another example sensor device in accordance with examples of the present disclosure.
Figure 2H:
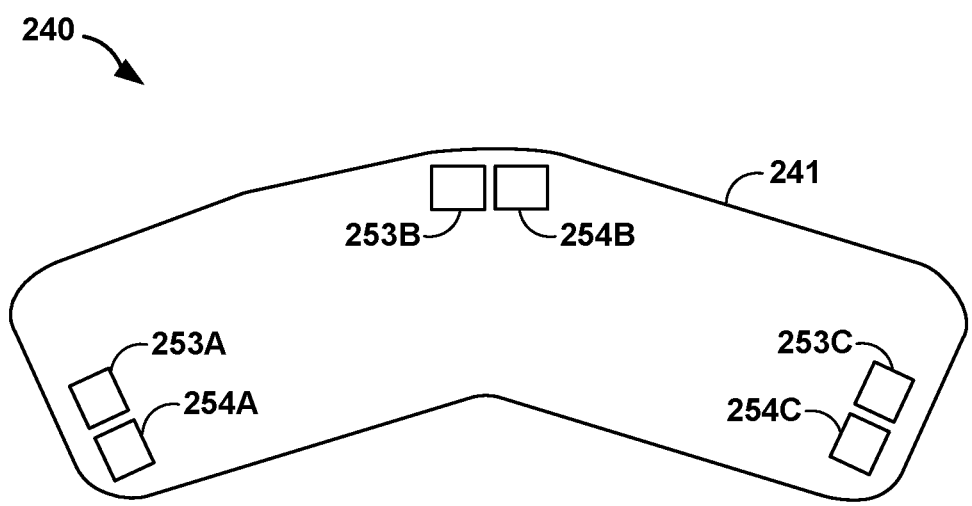
FIG. 2H depicts a top view of another example sensor device in accordance with examples of the present disclosure.

FIGS. 2G and 2H depict top views of devices in accordance with examples of the present disclosure. FIG. 2G depicts housing 201 of sensor device 210, which includes electrodes 213A-213C arranged at the perimeter of housing 201. Each of electrodes 213A-213C may be configured to receive raw signals including cardiac and brain components. Sensor device 210 may include circuitry configured to filter the raw signals received by electrodes 213A-213C to generate cardiac signals and brain signals, e.g., ECG and EEG signals. In some examples, this circuitry may be located outside of sensor device 210.

FIG. 2H depicts housing 241 of sensor device 240, which includes electrodes 253A-253C and 254A-254C. Electrodes 253A and 254A together may be referred to as a segmented electrode. Similarly, electrodes 253B and 254B may be referred to as a segmented electrode, and electrodes 253C and 254C may be referred to as a segmented electrode. Insulative material may separate the conductive portions (e.g., electrodes 253A and 254A) of a segmented electrode.

Circuitry may be configured to generate a first cardiac, e.g., ECG, signal based on a differential signal received at electrodes 253A and 253B, generate a second cardiac signal based on a differential signal received at electrodes 253B and 253C, and/or generate a third cardiac signal based on a differential signal received at electrodes 253C and 253A. Likewise, the circuitry may be configured to generate a first brain, e.g., EEG, signal based on a differential signal received at electrodes 254A and 254B, generate a second brain signal based on a differential signal received at electrodes 254B and 254C, and/or generate a third brain signal based on a differential signal received at electrodes 254C and 254A.

Figure 2I:
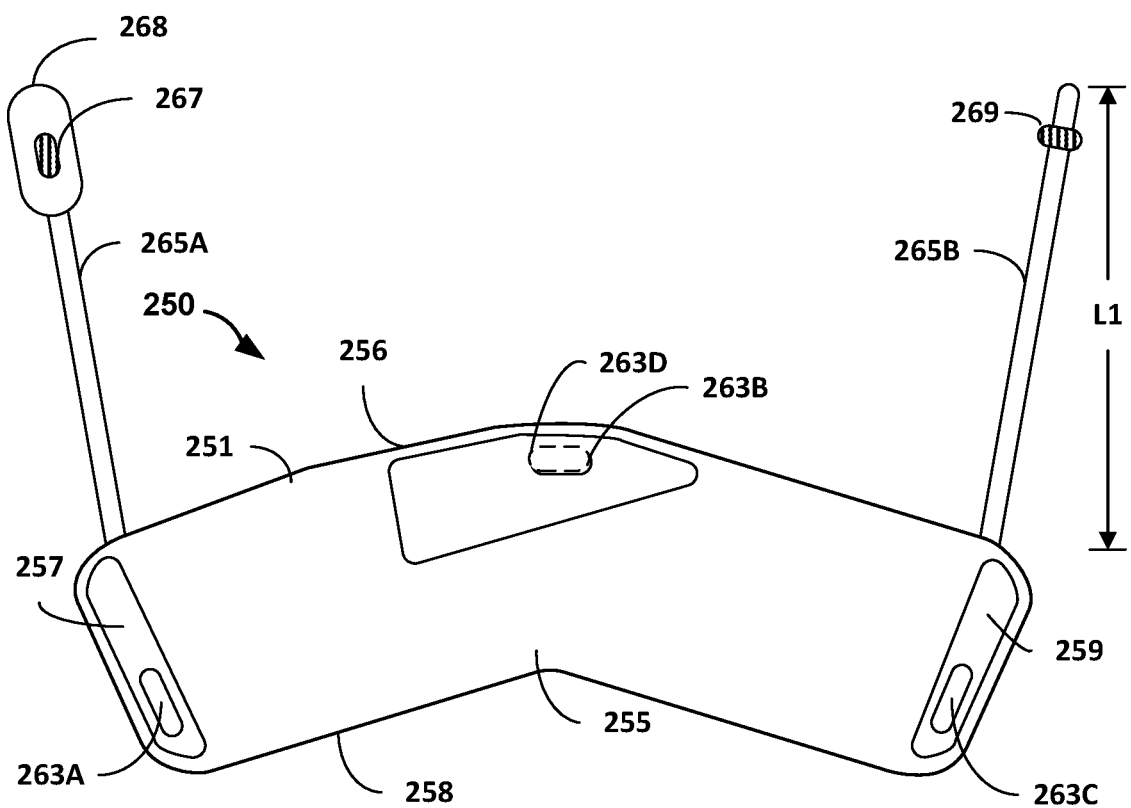
FIG. 2I depicts a top view of another example sensor device that includes electrode extensions in accordance with examples of the present disclosure.

FIG. 2I depicts a top view of another example sensor device 250, which includes electrodes 263A-236D, 267, and 269. Each of electrodes 263A-236D, 267, and 269 may be configured to receive raw signals including cardiac and brain, e.g., ECG and EEG, components. Sensor device 250 may include circuitry configured to filter the raw signals received by electrodes 263A-236D, 267, and 269 to generate cardiac signals and brain signals, e.g., ECG and EEG signals. Sensor device 250 may also include circuitry configured to measure impedance of tissue via electrodes 263A-236D, 267, and 269.

In the example of FIG. 2I, sensor device 250 include a housing 251, which includes a superior side surface 256, an opposing inferior side surface 258, a central portion 255, a first lateral portion (or left portion) 257, and a second lateral portion (or right portion) 259. Electrodes 263 are distributed about housing 251 such that a central electrode 263B is disposed within the central portion 255 (e.g., substantially centrally along a horizontal axis of the device), a left electrode 263A is disposed within the left portion 257, and a right electrode 263C is disposed within the right portion 259.

Sensor device 250 further include electrode extensions 265A and 265B (collectively "electrode extensions 265"). As illustrated in FIG. 2I, electrode extension 265A includes a paddle 268 such that one or more electrodes 267 are distributed on paddle 268. Electrode extension 265B includes one or more ring electrodes 269. In some examples, electrode extensions 265 may be connected to a housing 256 of sensor device 250 via header pins. In some examples, electrode extensions 265 may be permanently attached to housing 256 of sensor device 250. The number and types of electrode extensions 265, electrodes on such extensions, and electrodes on housing 251 may differ from that illustrated by FIG. 2I in some examples.

In some examples, electrode extensions 265 can have a length LI of from about 15 to about 50 mm, from about 20 to about 30 mm, or about 25 mm. One or more electrode extensions 265 may provide sensor device 250 larger sensing vectors for sensing signals via electrodes. The larger (longer) sensing vectors that include one or more electrodes on one or more extensions may facilitate improved signal quality relative to smaller (shorter) sensing vectors.

Electrode extensions 265 are inherently flexible, allowing conformance to neck and/or cranial anatomy. Additionally, the length and flexibility of one or more electrode extensions 265 may allow electrodes on the extension to advantageously be positioned proximate to certain brain structures or locations, vascular structures, or other anatomical structures or locations, which may also facilitate improved signal quality, e.g., when the signal originates from or is affected by the structure. For example, electrode extensions 265A and 265B can extend superiorly from sensor device 250 for enhanced brain signal sensing and detection. Improved signal quality may result in improved performance of algorithms for predicting or detecting patient conditions using such signals. In examples in which one or more electrode extensions 265 are implanted, the extension may be tunneled under the scalp to a position one or more electrodes on the extension at a desired location of the cranium.

FIGS. 2J-2N and 2P depict example sensor devices 270J-270P that includes electrode extensions 272J-272P, 276K, 276N, 284M-284P, 285M-285P, and 286M-286P, in accordance with examples of the present disclosure. Sensor devices 270J-270P may be similar in other aspects to the sensor devices illustrated and described with respect to FIGS. 1A-2I, e.g., may include electronics within a housing, and electrodes on the housing. The electrode extensions shown in FIGS. 2J-2P may also be referred to as leads. The electrodes on electrode extensions 272J-272P, 276K, 276N, 284M-284P, 285M-285P, and 286M-286P may be ring electrodes or paddle electrodes, as examples.

Figure 2J:
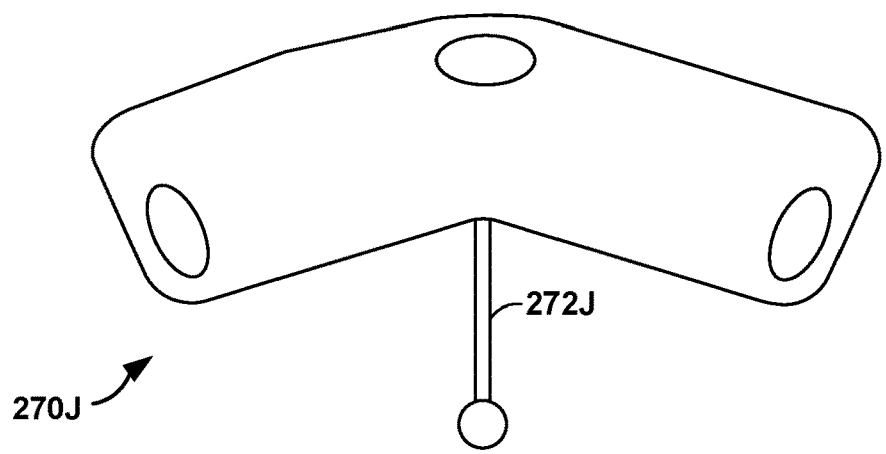
FIGS. 2J-2N and 2P depict example sensor devices that includes electrode extensions, in accordance with examples of the present disclosure.
Figure 2K:
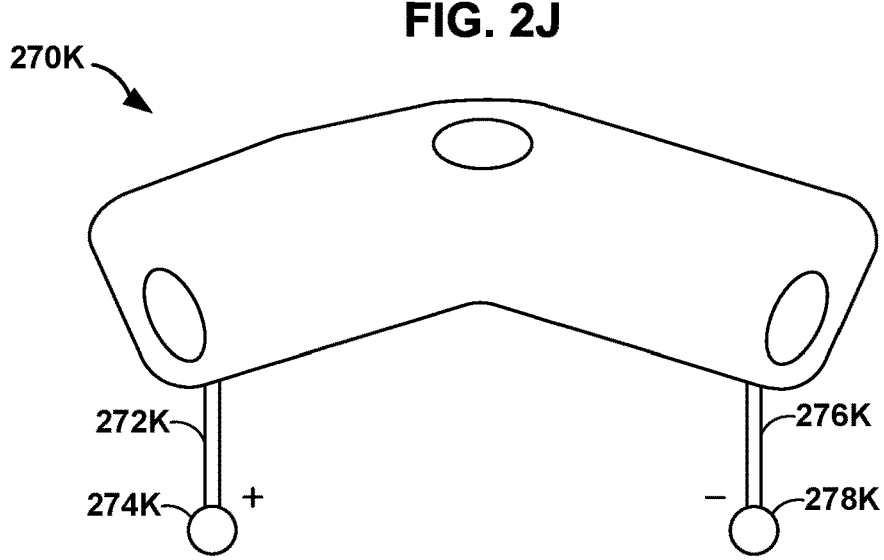
Figure 2L:
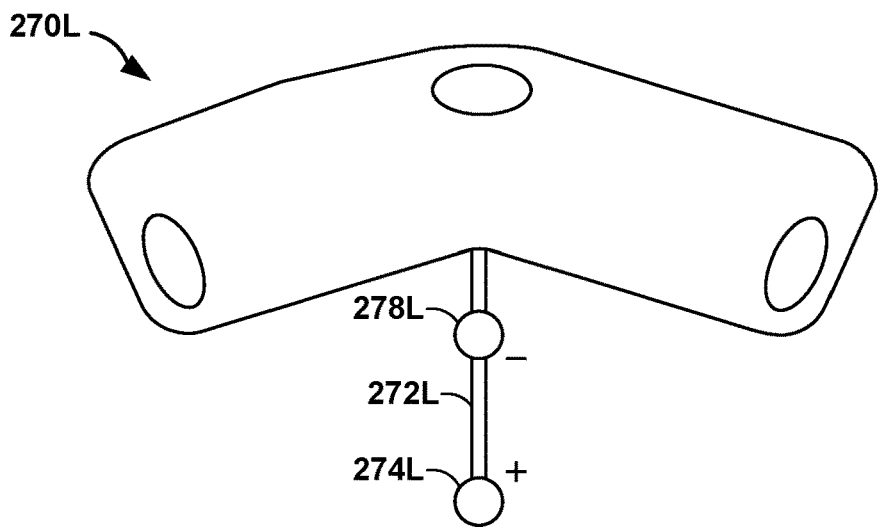

FIGS. 2J-2L show examples of electrode extensions 272J-272L and 276K that can be positioned to extend from sensor devices 270J-270L in a first direction, and FIGS. 2M-2P show examples of electrode extensions 272M-272P and 276N that can be positioned to extend from sensor devices 270M-270P in the first direction and electrode extensions 284M-284P, 285M-285P, and 286M-286P that can be positioned to extend from sensor devices 270M-270P in a second direction that is opposite from the first direction. In some examples, the first direction may be an inferior direction, e.g., towards the neck and shoulders of the patient, and the second direction may be a superior direction, e.g., towards the upper cranium and scalp of the patient. For example, a first electrode extension may be positioned to extend towards a first temporal region, and a second electrode extension may be positioned to extend towards a second temporal region. Electrode extensions 272J-272P and 276K shown in FIGS. 2J-2P can extend towards the neck and shoulders for enhanced cardiac signal sensing and detection. Electrode extensions 284M-284P, 285M-285P, and 286M-286P shown in FIGS. 2M-2P can be positioned to extend superiorly toward the upper cranium and scalp for enhanced brain signal sensing.

FIG. 2J shows an example of single electrode extension 272J that extends from the center of sensor device 270J. FIG. 2K shows an example of two electrode extensions 272K and 276K that extend from opposing ends of sensor device 270K. Electrode 274K on electrode extension 272K may have a positive polarity, and electrode 278K on electrode extension 276K may have a negative polarity, or the polarities of the electrodes may be reversed, such that the electrodes have opposite polarities. FIG. 2L shows an example of single electrode extension 272L that extends from the center of sensor device 270L. There are two electrodes 274L and 278L with opposing polarities on single electrode extension 272L. Thus, sensor devices 270K and 270L shown in FIGS. 2K and 2L may be configured to receive a differential signal via electrodes 274K, 278K, 274L, and 278L on one or more electrode extensions 272K, 276K, and 272L. In the example of FIG. 2J, a generally vertical or non-horizontal sensing vector may be formed between the electrode on extension 272J and an electrode on a housing of sensor device 270 J, and in the example of FIG. 2L, a generally vertical sensing vector may be formed between electrodes 274L and 278L on extension 272L. In the example of FIG. 2K, a generally horizontal sensing vector may be formed between electrode 274K on extension 272K and electrode 278K on extension 276K.

Figure 2M:
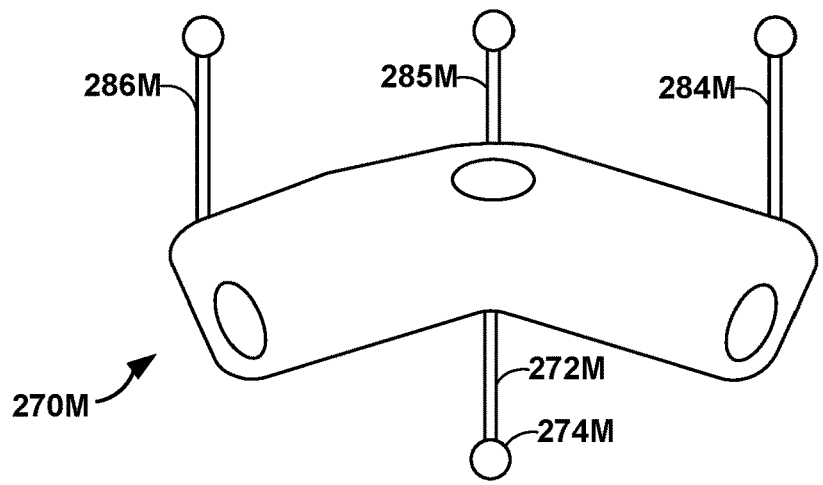
Figure 2N:
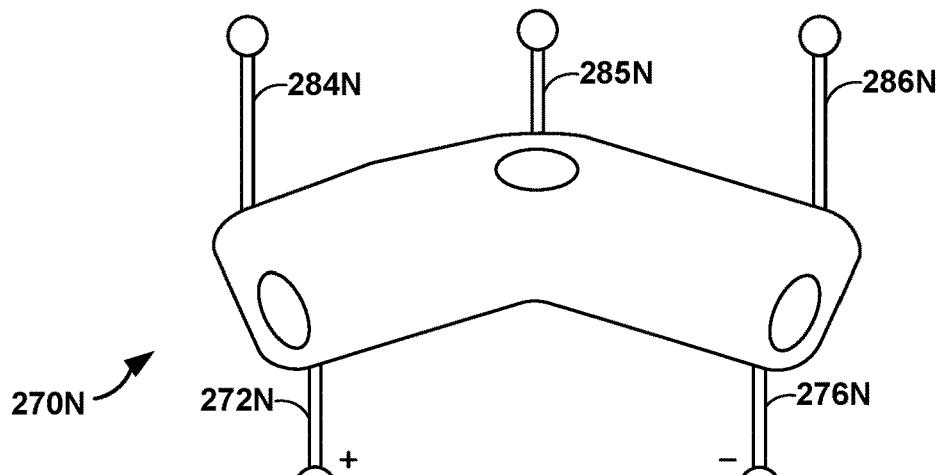
Figure 2P:
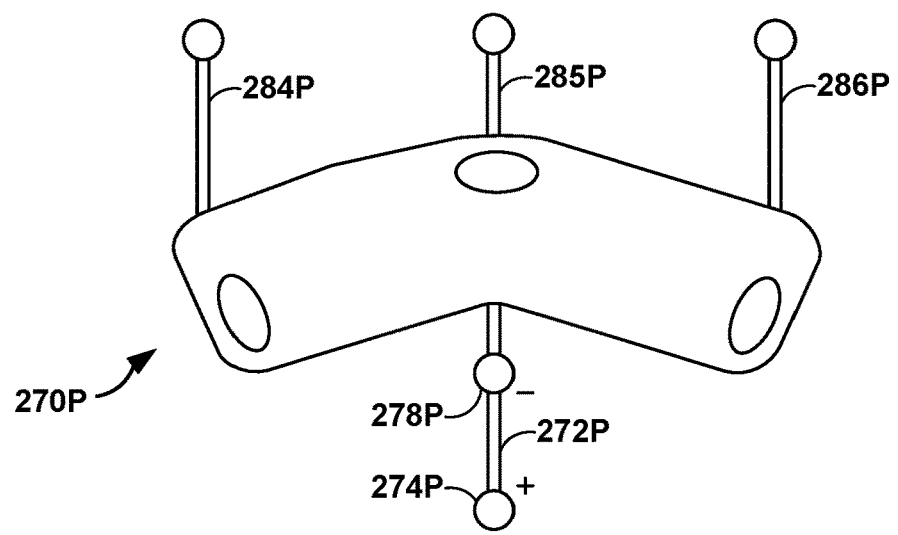

Each of sensor devices 270M-270P shown in FIGS. 2M-2P includes one or more electrode extensions 272M-272P and 276N that extend in a first direction and three electrode extensions 284M-284P, 285M-285P, and 286M-286P that extend in a second direction that is opposite from the first direction. FIG. 2M shows single electrode extension 272M that extends in the first direction from the center of sensor device 270M. FIG. 2N shows two electrode extensions 272N and 276N that extend in the first direction from opposing ends of sensor device 270N. FIG. 2P shows single electrode extension 272P that extends from the center of sensor device 270P, where single electrode extension 272P includes two electrodes 274P and 278P of opposing polarities.

Figure 2Q:
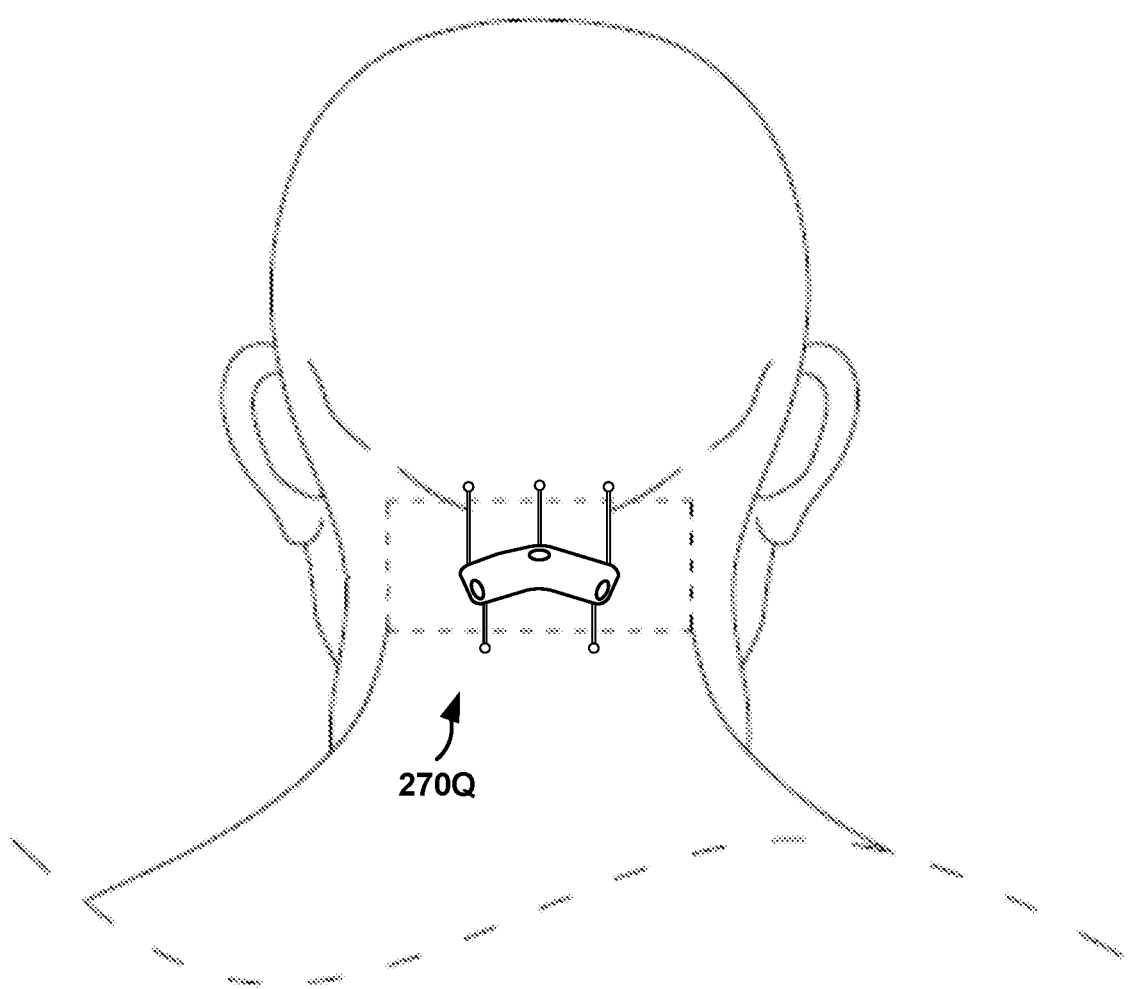
FIG. 2Q depicts an example sensor device that includes electrode extensions in conjunction with a patient, in accordance with examples of the present disclosure.

FIG. 2Q shows sensor device 270Q on the back of a patient's neck. In the illustrated example, sensor device 270Q is configured similarly to sensor device 270N of FIG. 2N. However, any of the sensor devices including extensions described with respect to FIGS. 21-2N, and 2P may be positioned in the manner illustrated by sensor device 270Q in FIG. 2Q. Additionally, any of the sensor devices including extensions described with respect to FIGS. 21-2N and 2P may be positioned at other locations described herein, such as temporally as illustrated with respect to FIG. 1B.

Such sensor devices may include one or more extensions extending in a first, inferior direction, toward the neck or shoulders of the patient. Extensions extending in this first direction may position electrodes to facilitate cardiac signal, e.g., ECG, sensing. Such sensor devices may include one or more extensions extending in a second, superior direction, opposite the first direction, toward the upper cranium and scalp of the patient. Extensions extending in this second direction may facilitate brain signal, e.g., EEG, sensing. Each extension may include one or more electrodes to provide one or more sensing vectors of one or more orientations with another electrode on the same extension, a different extension, or a housing of the sensor device.

Figure 2R:
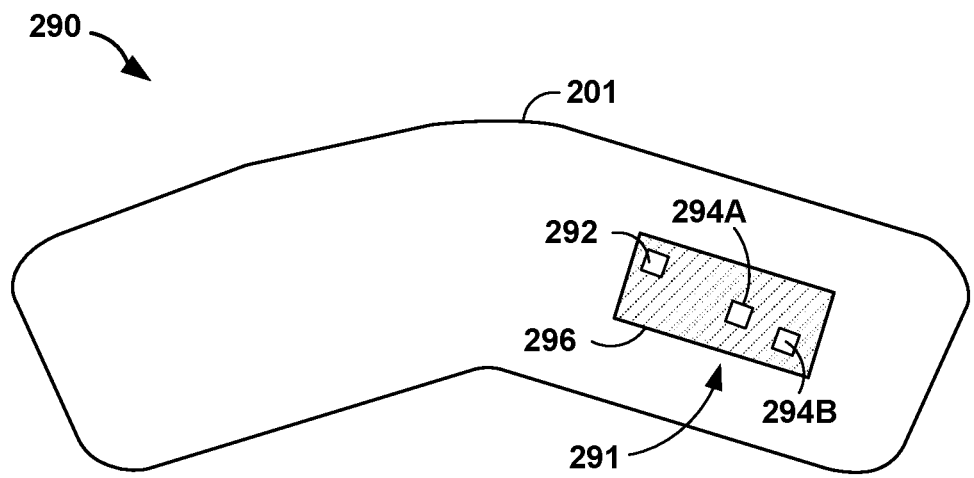
FIG. 2R depicts an example sensor device that includes an optical sensor, in accordance with examples of the present disclosure.

FIG. 2R depicts an example sensor device 290 that includes an optical sensor 291. Optical sensor 291 may be used for any of a variety of purposes described herein. For example, optical sensor 291 may be used to sense oxygen saturation, e.g., $SpO_2$ or $StO_2$. As another example, the signal sensed by optical sensor may vary with the pulsatile flow of blood. Peak detection and/or other signal processing techniques may be used to identify heart beats within the optical signal. Processing circuitry may determine heart rate, heart rate variability, and other parameters derivable from a time series of heart beat detections based on optical signal. The processing circuitry may use optical signal as a surrogate for an ECG signal according to any of the techniques described herein.

In some examples, the processing circuitry may determine pulse transit time (PTT) based on depolarizations detected in an ECG signal and features detected in the optical signal. PTT may be inversely correlated with, and thus indicative of, blood pressure. PTT may act as a surrogate for blood pressure in the techniques described herein.

In the example of FIG. 2R optical sensor 291 includes a light emitter 292, and light detectors 294A and 294B (hereinafter, "light detectors 294"). The numbers of light emitters and detectors illustrated in FIG. 2R is an example, and in other examples an optical sensor may include different numbers of light emitters and/or light detectors. Other than the inclusion of optical sensor 291, sensor device 290 may be configured substantially similarly to any other sensor devices described herein, such as those described with respect to FIGS. 1A-1C, FIGS. 2A-2N, 2P, and 2Q, and FIG. 4. For example, sensor device 290 may include a housing 201 configured as described with respect to FIGS. 2A-2N, 2P, and 2Q. Although not illustrated in FIG. 2R, sensor device 290 may include electrodes as described with respect to any of FIGS. 2A-2N, 2P, and 2Q. Furthermore, although not illustrated in FIG. 2R, sensor device 290 may, in some examples, include extensions or leads, as described with respect to FIGS. 2I-2N, 2P, and 2Q. In some examples, optical sensor 291 may be located on an extension or lead that extends from housing 201, instead of being located on housing 201 as illustrated in FIG. 2R. Locating optical sensor 291 on a lead or extension may allow optical sensor 291 to sense an optical signal at one location, while sensor device 290 senses an ECG or EEG signal via electrodes at another location, which may be advantageous where preferred locations for sensing the signals are different. Example locations for optical sensor 291 include a temporal location, temple location, occipital location, forehead location, or a location on the crown of the head.

In some examples, optical sensor 291 may be positioned to emit light to and receive light from a vascular bed on the skull. In some examples, optical sensor 291 may be located on a major surface of housing 201 that faces the skull, which may help minimize interference from background light coming from outside the body of the patient. In some examples, optical sensor 291 may be located on a surface of skull opposite another surface that include one or more electrodes.

Light emitter(s) 292 include a light source, such as one or more light emitting diodes (LEDs), that may emit light at one or more wavelengths within the visible (VIS) and/or near-infrared (NIR) spectra. For example, light emitter(s) 292 may emit light at one or more of about 660 nanometer (nm), 720 nm, 760 nm, 800 nm, or at any other suitable wavelengths.

In some examples, techniques for determining blood oxygenation, e.g., $SpO_2$ or $StO_2$, may include using light emitter(s) 292 to emit light at one or more VIS wavelengths (e.g., approximately 660 nm) and at one or more NIR wavelengths (e.g., approximately 850-890 nm). The combination of VIS and NIR wavelengths may help enable processing circuitry to distinguish oxygenated hemoglobin from deoxygenated hemoglobin, since as hemoglobin becomes less oxygenated, an attenuation of VIS light increases and an attenuation of NIR decreases. By comparing the amount of VIS light detected by light detectors 294 to the amount of NIR light detected by light detectors 294, processing circuitry may determine the relative amounts of oxygenated and deoxygenated hemoglobin in the tissue of a patient.

Techniques for determining a blood oxygenation value or sensing the pulsatile flow of blood using an optical signal may be based on the optical properties of blood-perfused tissue that change depending upon the relative amounts of oxygenated and deoxygenated hemoglobin in the microcirculation of tissue. These optical properties are due, at least in part, to the different optical absorption spectra of oxygenated and deoxygenated hemoglobin. Thus, the oxygen saturation level of the patient's tissue may affect the amount of light that is absorbed by blood within the tissue, and the amount of light that is reflected by the tissue. Light detectors 294 each may receive light from light emitter 292 that is reflected by the tissue, and generate electrical signals indicating the intensities of the light detected by light detectors 294. Processing circuitry then may evaluate the electrical signals from light detectors 294 in order to determine an oxygen saturation value, to detect heart beats, and/or to determine PTT values. In some examples, light emitter 292 may additionally or alternatively emit other wavelengths of light, such as green or amber light, because the variation of signals detected by detectors 294 with pulsatile blood flow may be greater at such wavelengths, which may increase the ability to detect pulses to identify heart beats and/or determine PTT.

In some examples, a difference between the electrical signals generated by light detectors 294A and 294B may enhance an accuracy of the determinations. For example, because tissue absorbs some of the light emitted by light emitter 292, the intensity of the light reflected by tissue becomes attenuated as the distance (and amount of tissue) between light emitter 292 and light detectors 294 increases. Thus, because light detector 294B is positioned further from light emitter 292 than light detector 294A, the intensity of light detected by light detector 294B should be less than the intensity of light detected by light detector 294A. Due to the close proximity of detectors 294A, 294B to one another, the difference between the intensity of light detected by light detector 294A and the intensity of light detected by light detector 294B should be attributable only to the difference in distance from light emitter 292.

In some examples, optical sensor 291 comprises a window 296, e.g., glass or sapphire, formed as a portion of housing 201. Light emitter 292 and light detectors 294 may be located beneath window 296. Window 296 may be transparent or substantially transparent to the light, e.g., wavelengths of light, emitted and detected by optical sensor 291. In some examples, all or a substantial portion of one of the major surfaces of housing 201 may formed as window 296.

In some examples, one or more portions of window 296 may be optically masked. In some examples, portions of window with the exception of those above emitter 292 and detectors 294 may be optically masked. Optical masking may reduce or prevent transmission of light, e.g., to prevent internal reflection within window 296 that may confound measurements. An optical mask may include a material configured to substantially absorb emitted light, such as titanium nitride, columnar titanium nitride, titanium, or another material suitable to absorb selected wavelengths of light that may be emitted by light emitter 292.

Figure 3A:
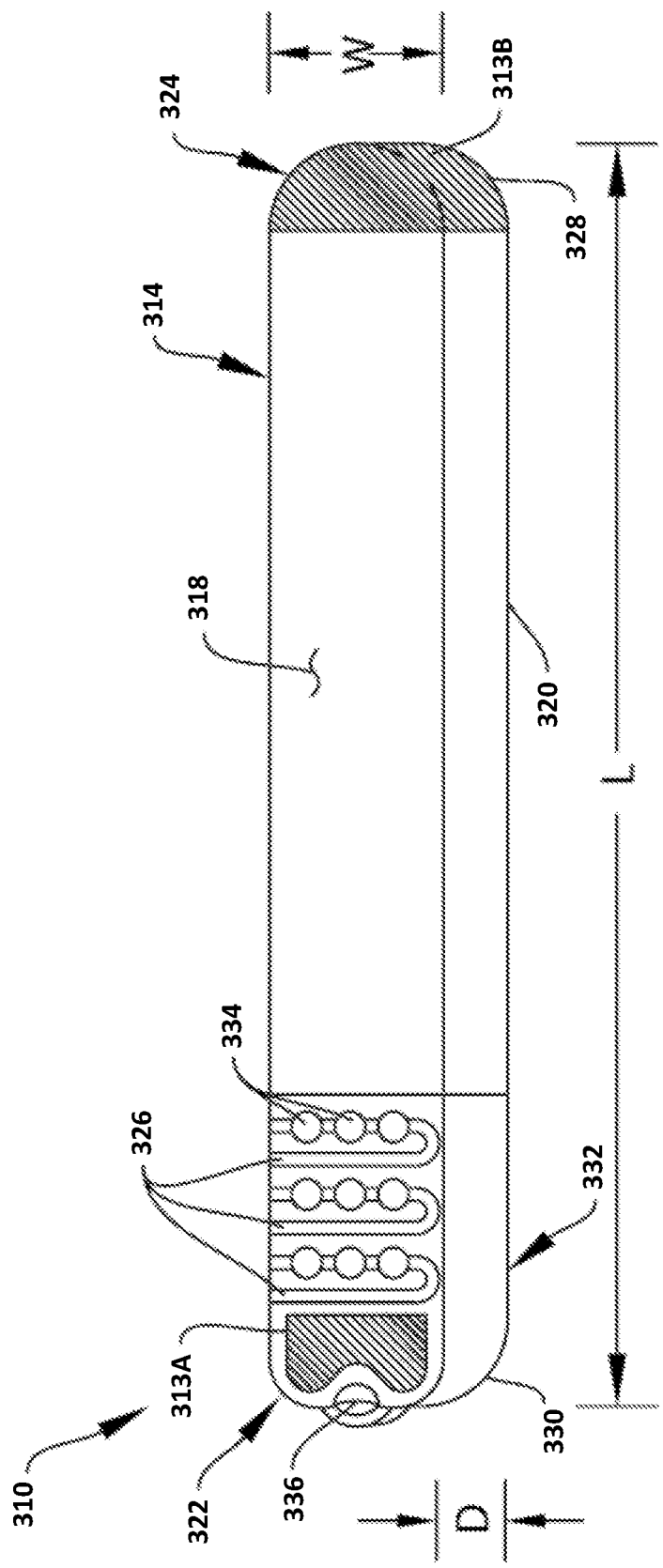
FIGS. 3A-3C depict other sensor devices in accordance with examples of the present disclosure.
Figure 3B:
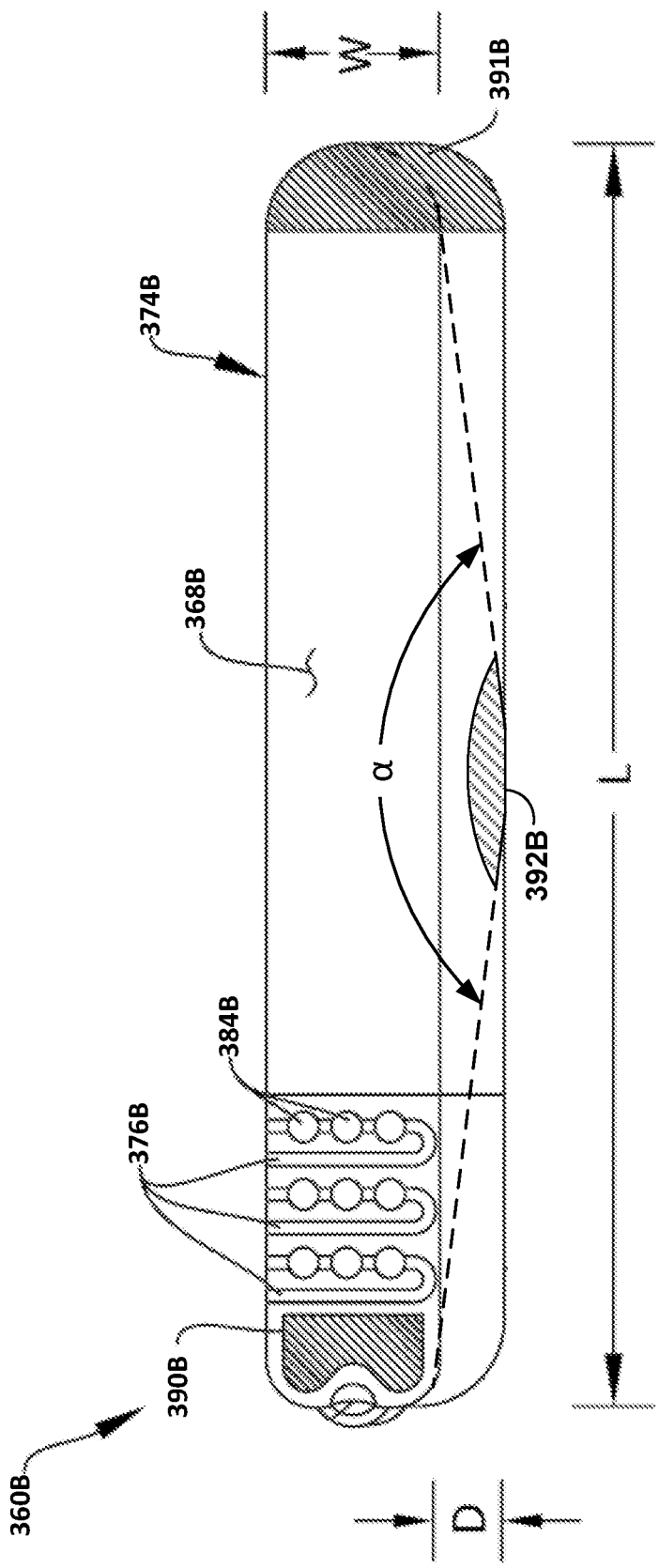
Figure 3C:
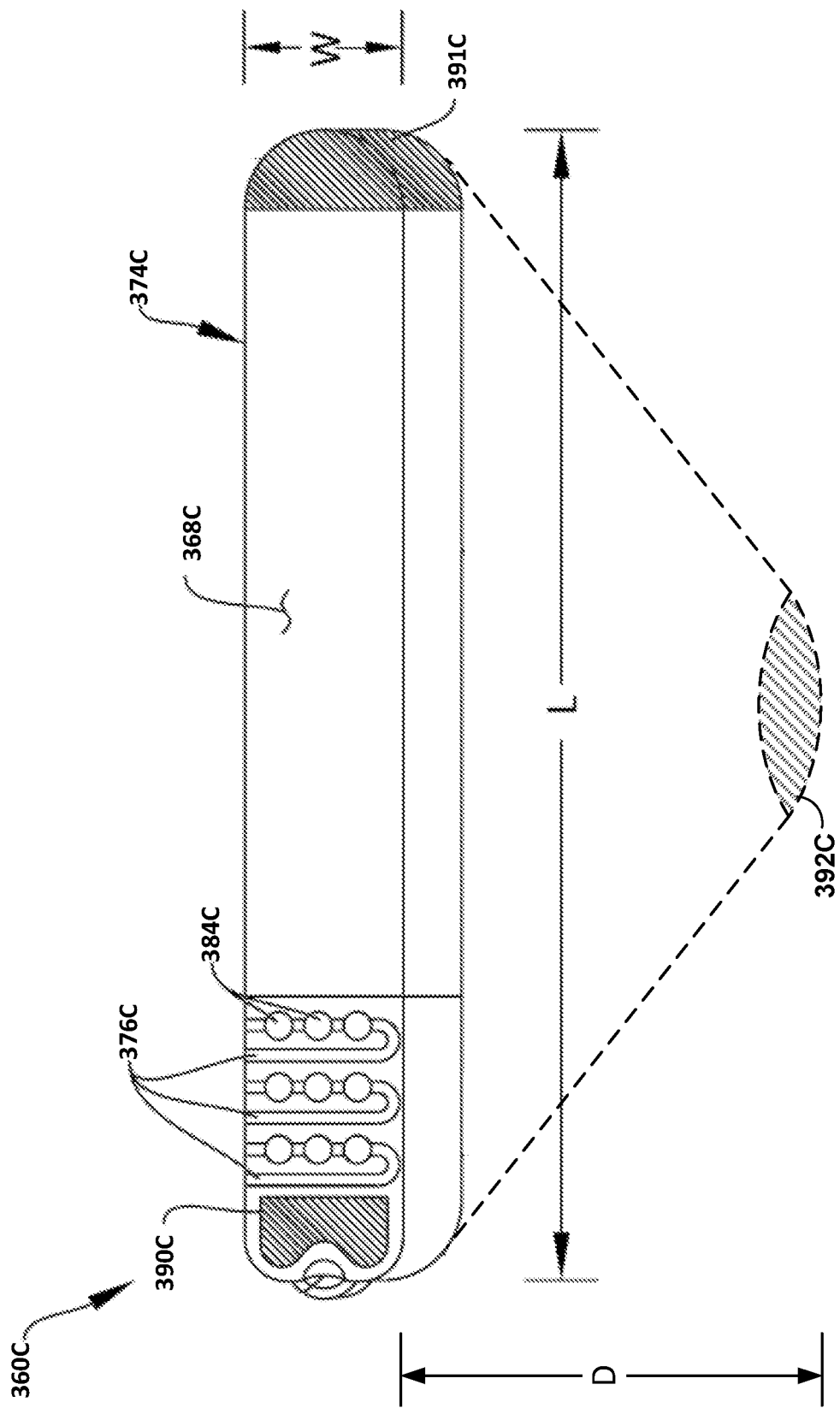

FIGS. 3A-3C depict other example sensor devices 310, 360B, and 360C in in accordance with embodiments of the present technology. In some examples, sensor device 310 can include some or all of the features of sensor devices 106, 210, 220, 230, and 400 described herein in accordance with embodiments of the present technology, and can include additional features as described in connection with FIG. 3A. In the example shown in FIG. 3A, sensor device 310 may be embodied as a monitoring device having housing 314, proximal electrode 313A and distal electrode 313B (individually or collectively "electrode 313" or "electrodes 313"). Housing 314 may further comprise first major surface 318, second major surface 320, proximal end 322, and distal end 324. Housing 314 encloses electronic circuitry located inside sensor device 310 and protects the circuitry contained therein from body fluids. Electrical feedthroughs provide electrical connection of electrodes 313. In an example, sensor device 310 may be embodied as an external monitor, such as patch that may be positioned on an external surface of the patient, or another type of medical device (e.g., instead of as an ICM), such as described further herein.

In the example shown in FIG. 3A, sensor device 310 is defined by a length "L," a width "W," and thickness or depth "D." sensor device 310 may be in the form of an elongated rectangular prism wherein the length L is significantly larger than the width W, which in turn is larger than the depth D. In one example, the geometry of sensor device 310—in particular, a width W being greater than the depth D—is selected to allow sensor device 310 to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 313a and distal electrode 313B may range from 30 millimeters (mm) to 55 mm, 35 mm to 55 mm, and from 40 mm to 55 mm and may be any range or individual spacing from 25 mm to 60 mm. In some examples, the length L may be from 30 mm to about 70 mm. In other examples, the length L may range from 40 mm to 60 mm, 45 mm to 60 mm and may be any length or range of lengths between about 30 mm and about 70 mm. In addition, the width W of first major surface 18 may range from 3 mm to 10 mm and may be any single or range of widths between 3 mm and 10 mm. The thickness of depth D of sensor device 310 may range from 2 mm to 9 mm. In other examples, the depth D of sensor device 310 may range from 2 mm to 5 mm and may be any single or range of depths from 2 mm to 9 mm. In addition, sensor device 310 according to an example of the present disclosure is has a geometry and size designed for ease of implant and patient comfort. Examples of sensor device 310 described in this disclosure may have a volume of 3 cc or less, 2 cc or less, 1 cc or less, 0.9 cc or less, 0.8 cc or less, 0.7 cc or less, 0.6 cc or less, 0.5 cc or less, 0.4 cc or less, any volume between 3 and 0.4 cc, or any volume less than 0.4 cc. In addition, in the example shown in FIG. 3A, proximal end 322 and distal end 324 are rounded to reduce discomfort and irritation to surrounding tissue once inserted under the skin of the patient.

In the example shown in FIG. 3A, once inserted within the patient, the first major surface 318 faces outward, toward the skin of the patient while the second major surface 320 is located opposite the first major surface 318. Consequently, the first and second major surfaces may face in directions along a sagittal axis of patient, and this orientation may be consistently achieved upon implantation due to the dimensions of sensor device 310. Additionally, an accelerometer, or axis of an accelerometer, may be oriented along the sagittal axis.

Proximal electrode 313A and distal electrode 313B are used to sense signals (e.g., EEG signals, ECG signals, other brain and/or cardiac signals, or impedance) which may be submuscular or subcutaneous. Signals may be stored in a memory of sensor device 310, and signal data may be transmitted via integrated antenna 326 to another medical device, which may be another implantable device or an external device, such as external device 108 (FIG. 1A). In some examples, electrodes 313A and 313B may additionally or alternatively be used for sensing any bio-potential signal of interest, such as an EMG, or a nerve signal, from any implanted location.

In the example shown in FIG. 3A, proximal electrode 313A is in close proximity to the proximal end 322, and distal electrode 313B is in close proximity to distal end 324. In this example, distal electrode 313B is not limited to a flattened, outward facing surface, but may extend from first major surface 318 around rounded edges 328 or end surface 330 and onto the second major surface 320 so that the electrode 313B has a three-dimensional curved configuration. In the example shown in FIG. 3, proximal electrode 313A is located on first major surface 318 and is substantially flat, outward facing. However, in other examples proximal electrode 313A may utilize the three-dimensional curved configuration of distal electrode 313B, providing a three-dimensional proximal electrode (not shown in this example). Similarly, in other examples distal electrode 313B may utilize a substantially flat, outward facing electrode located on first major surface 318 similar to that shown with respect to proximal electrode 313A. The various electrode configurations allow for configurations in which proximal electrode 313A and distal electrode 313B are located on both first major surface 318 and second major surface 320. In other configurations, such as that shown in FIG. 3, only one of proximal electrode 313A and distal electrode 313B is located on both major surfaces 318 and 320, and in still other configurations both proximal electrode 313A and distal electrode 313B are located on one of the first major surface 318 or the second major surface 320 (e.g., proximal electrode 313A located on first major surface 318 while distal electrode 313B is located on second major surface 320). In another example, sensor device 310 may include electrodes 313 on both first major surface 318 and second major surface 320 at or near the proximal and distal ends of the device, such that a total of four electrodes 313 are included on sensor device 310. Electrodes 313 may be formed of a plurality of different types of biocompatible conductive material (e.g., titanium nitride or platinum iridium), and may utilize one or more coatings such as titanium nitride or fractal titanium nitride. Although the example shown in FIG. 3A includes two electrodes 313, in some embodiments sensor device 310 can include 3, 4, 5, or more electrodes carried by the housing 314.

In the example shown in FIG. 3A, proximal end 322 includes a header assembly 332 that includes one or more of proximal electrode 313A, integrated antenna 326, anti-migration projections 334, or suture hole 336. Integrated antenna 326 is located on the same major surface (i.e., first major surface 318) as proximal electrode 313a and is also included as part of header assembly 332. Integrated antenna 326 allows sensor device 310 to transmit or receive data. In other examples, integrated antenna 326 may be formed on the opposite major surface as proximal electrode 313A, or may be incorporated within the housing 314 of sensor device 310. In the example shown in FIG. 3A, anti-migration projections 334 are located adjacent to integrated antenna 326 and protrude away from first major surface 318 to prevent longitudinal movement of the device. In the example shown in FIG. 3 anti-migration projections 334 includes a plurality (e.g., six or nine) small bumps or protrusions extending away from first major surface 318. As discussed above, in other examples anti-migration projections 334 may be located on the opposite major surface as proximal electrode 313A or integrated antenna 326. In addition, in the example shown in FIG. 3A header assembly 332 includes suture hole 336, which provides another means of securing sensor device 310 to the patient to prevent movement following insert. In the example shown, suture hole 336 is located adjacent to proximal electrode 313A. In one example, header assembly 332 is a molded header assembly made from a polymeric or plastic material, which may be integrated or separable from the main portion of sensor device 310.

FIG. 3B shows a third electrode 392B at a midpoint between electrodes 390B and 391B. The dimension D of housing 374B of sensor device 360B can be increased to adjust the angle α to obtain a more orthogonal orientation for the triangular configuration of electrodes 390B-392B. In some examples, sensor device 360B may have the same shape and dimensions as sensor device 310, except that electrode 392B is added to the side surface or back surface of housing 374B to create a triangle-shaped electrode configuration. In addition, FIG. 3C shows sensor device 360 with an extended third dimension D. Third electrode 392C is positioned at a corner to create a triangular-shaped electrode configuration with electrodes 390C and 391C. Dimension D can be designed to achieve specific angles for the triangular configuration of electrodes 390C-392C.

Figure 3D:
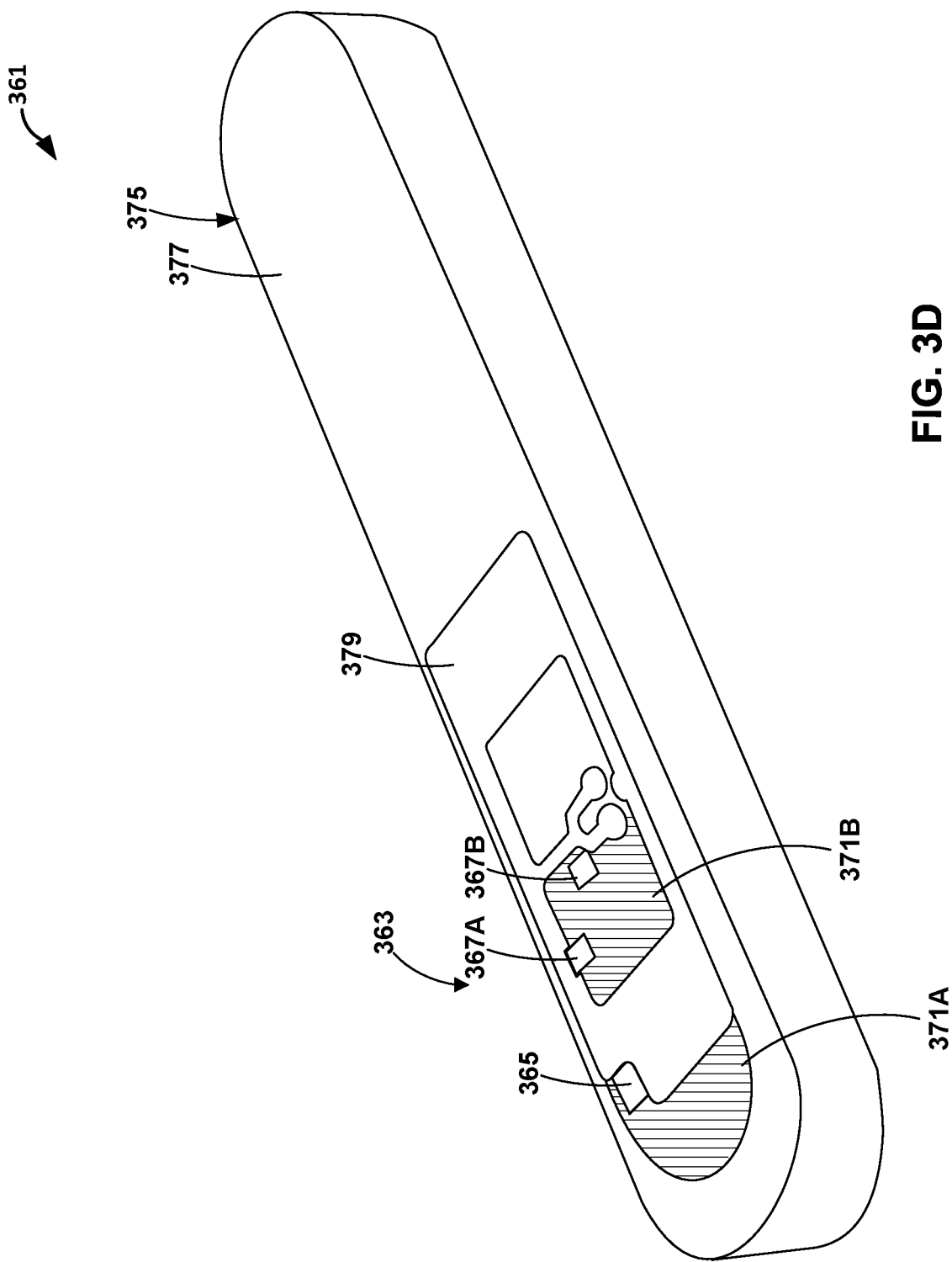
FIG. 3D depicts another example sensing device that includes an optical sensor, in accordance with examples of the present disclosure.

FIG. 3D depicts another example sensing device 361 that includes an optical sensor 363, in accordance with examples of the present disclosure. Optical sensor 363 may be configured and provide functionality as described above with respect to optical sensor 291 and FIG. 2R. Optical sensor 363 includes one or more light emitters 365 and light detectors 367A and 367B (hereinafter, "light detectors 367"), which may be configured and function substantially similarly to light emitter 292 and light detectors 294 described with respect to FIG. 2R. Other than the inclusion of optical sensor 363, sensor device 361 may be configured substantially similarly to any other sensor devices described herein, such as those described with respect to FIGS. 1A-1C, 3A-3C, and FIG. 4. For example, sensor device 363 may include a housing 375 configured as described with respect to FIGS. 3A-3C. Although not illustrated in FIG. 3D, sensor device 363 may include electrodes as described with respect to any of FIGS. 3A-3C. In some examples, a surface 377, e.g., a major surface or portion thereof, of a housing 375 may configured as a window that is transparent or substantially transparent to the light, e.g., wavelengths of light, emitted and detected by optical sensor 363.

As illustrated in FIG. 3D, sensor device 361 includes an antenna 379 disposed on surface 377 of housing 375. In some examples, antenna 379 may include a substrate layer and a metalized layer formed on the substrate layer. The substrate layer may include, for example, biocompatible polymer, such as polyamide or polyimide, silica glass, silicon, sapphire, or the like. The metalized layer may include, for example, aluminum, copper, silver, or other conductive metals. Antenna 379 may include other materials, such as, for example, ceramics or other dielectrics (e.g., as in dielectric resonator antennas). In some examples, antenna 379, e.g., a metalized layer or the like, may be formed directly on exterior surface 377 of housing 375.

Regardless of the material, antenna 379 may include an opaque or substantially opaque material. For example, an opaque (e.g., or substantially opaque) material may block transmission of at least a portion of radiation of a selected wavelength, such as, between about 75% and about 100% of visible light.

In examples in which antenna 379 includes an opaque material, components of optical sensor 363 may be arranged relative to portions of antenna 379 to reduce or prevent optical interference between components. For example, as illustrated in FIG. 3D, light emitter 365 is positioned on an outer perimeter of antenna 379, whereas light detectors 367 are positioned within an aperture defined by antenna 379. In this way, antenna 379 may define an optical boundary of opaque material that reduces or prevents transmission of light from emitter 365 directly to detectors 367. Rather, light emitted from light emitter 365 must travel through tissue. In some, one or more optical masks 371A and 371B may be applied to further prevent optical interference.

Figure 4:
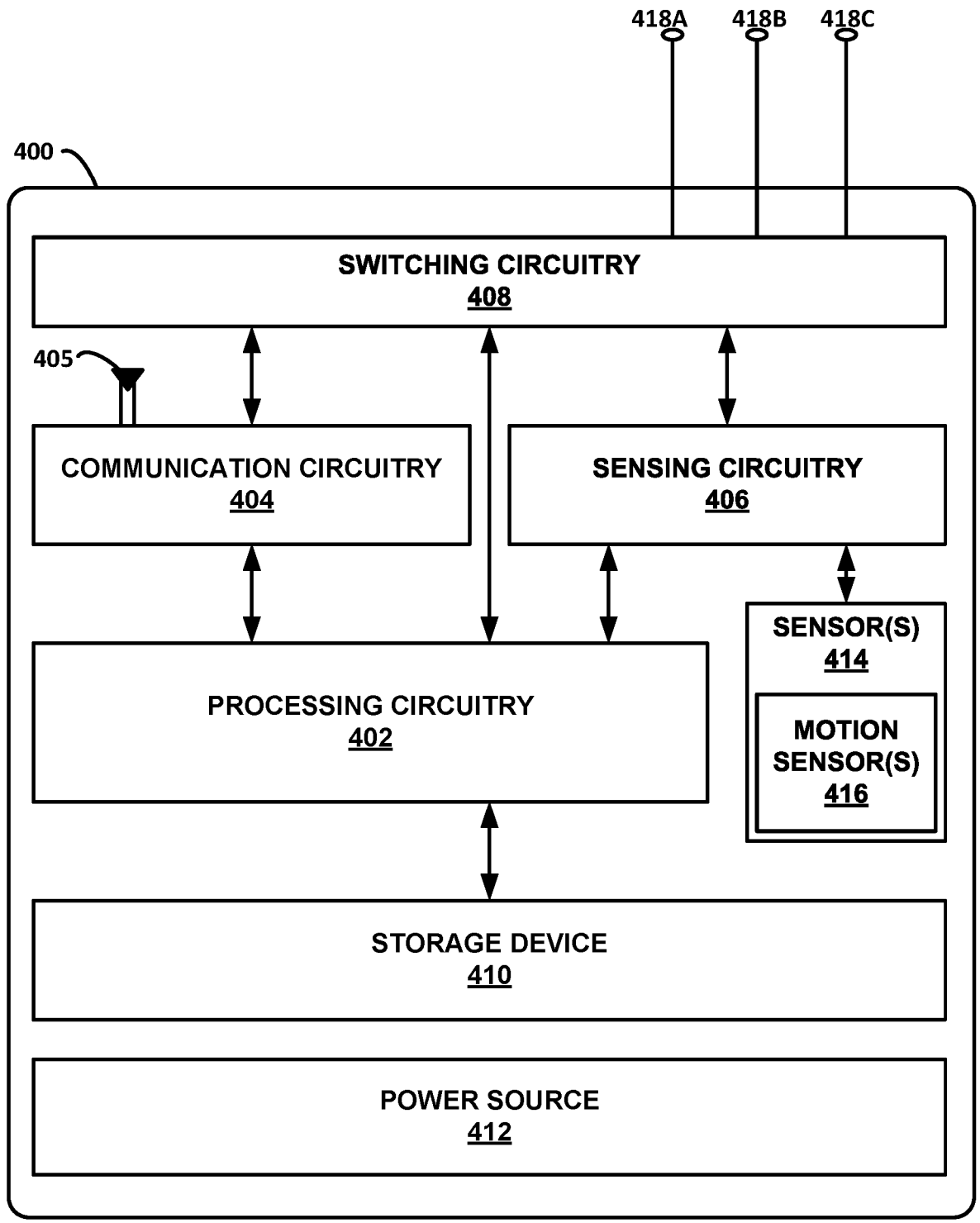
FIG. 4 is a block diagram illustrating an example configuration of a sensor device.

FIG. 4 is a block diagram of an example configuration of a sensor device 400 configured to sense signals used to generate at least one of a detection, prediction, or classification of a condition of a patient. Sensor device 400 may be an example of any of sensor devices 106, 210, 220, 230, 240, 250, 270, 310, 360A, and 360B. In the illustrated example, sensor device 400 includes electrodes 418A-418C (collectively, "electrodes 418"), antenna 405, processing circuitry 402, sensing circuitry 406, communication circuitry 404, storage device 410, switching circuitry 408, sensors 414 including motion sensor(s) 416, and power source 412.

Processing circuitry 402 may include fixed function circuitry and/or programmable processing circuitry. Processing circuitry 402 may include any one or more of a microprocessor, a GPU, a TPU, a controller, a DSP, an ASIC, an FPGA, or equivalent discrete or analog logic circuitry. In some examples, processing circuitry 402 may include multiple components, such as any combination of one or more microprocessors, one or more GPUs, one or more TPUs, one or more controllers, one or more DSPs, one or more ASICs, or one or more FPGAs, as well as other discrete or integrated logic circuitry. The functions attributed to processing circuitry 402 herein may be embodied as software, firmware, hardware or any combination thereof. Processing circuitry 402 may be an example of or component of processing circuitry 110 (FIGS. 1A and 1B), and may be processing circuitry of any of sensor devices 106, 210, 220, 230, 240, 250, 270, 310, 360A, and 360B.

Sensing circuitry 406 and communication circuitry 404 may be selectively coupled to electrodes 418 via switching circuitry 408, as controlled by processing circuitry 402. Sensing circuitry 406 may monitor signals from electrodes 418A-418C in order to monitor activity of the brain and heart (e.g., to produce an EEG, and an ECG or other cardiac signal) from which processing circuitry 402 (or processing circuitry of another device) may determine values over time of parameters used to generate the detection, prediction, or classification. Sensing circuitry 406 may also sense physiological characteristics such as subcutaneous tissue impedance, the impedance being indicative of at least some aspects of patient 102's respiratory patterns or perfusion. Sensing circuitry 406 also may monitor signals from sensors 414, which may include motion sensor(s) 416, and any additional sensors, such as optical sensors 291, 363, pressure sensors, or acoustic sensors, that may be positioned on or in sensor device 400.

In some examples, a subcutaneous impedance signal collected by sensor device 400 may indicate a respiratory rate and/or a respiratory intensity of patient 102. In some examples, a respiration component may additionally (using a blended sensor technique) or alternatively be sensed in other signals, such as a motion sensor signal, optical signal, or as a component (e.g., baseline shift) of the cardiac signal sensed via electrodes 418. In some examples, sensing circuitry 406 may include one or more filters and amplifiers for filtering and amplifying signals received from one or more of electrodes 418 and/or sensor(s) 414.

Communication circuitry 404 may include any suitable hardware, firmware, software or any combination thereof for communicating with another device, such as external device 108. Under the control of processing circuitry 402, communication circuitry 404 may receive downlink telemetry from, as well as send uplink telemetry to, external device 108 or another device with the aid of an internal or external antenna, e.g., antenna 405. In some examples, communication circuitry 404 may receive downlink telemetry from, as well as send uplink telemetry to, external device 108 or another device via tissue conductance communication (TCC) using two or more of electrodes 418, e.g., as selected by processing circuitry 402 via switching circuitry 408. In addition, processing circuitry 402 may communicate with a networked computing device via an external device (e.g., external device 108) and a computer network, such as the Medtronic CareLink® Network developed by Medtronic, plc, of Dublin, Ireland.

A clinician or other user may retrieve data from sensor device 400 using external device 108, or by using another local or networked computing device configured to communicate with processing circuitry 402 via communication circuitry 404. The clinician may also program parameters of sensor device 400 using external device 108 or another local or networked computing device.

In some examples, storage device 410 may be referred to as a memory and include computer-readable instructions that, when executed by processing circuitry 402, cause sensor device 400 and processing circuitry 402 to perform various functions attributed to sensor device 400 and processing circuitry 402 herein. Storage device 410 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 410 may also store data generated by sensing circuitry 406, such as signals, or data generated by processing circuitry 402, such as parameter values or indications of detections, predictions, or classifications of conditions.

Power source 412 is configured to deliver operating power to the components of sensor device 400. Power source 412 may include a battery and a power generation circuit to produce the operating power. In some examples, the battery is rechargeable to allow extended operation. In some examples, recharging is accomplished through proximal inductive interaction between an external charger and an inductive charging coil within external device 108. Power source 412 may include any one or more of a plurality of different battery types, such as nickel cadmium batteries and lithium ion batteries. A non-rechargeable battery may be selected to last for several years, while a rechargeable battery may be inductively charged from an external device, e.g., on a daily or weekly basis.

As described herein, sensor device 400 may be configured to sense signals, e.g., via electrodes 418 and sensors 414, for detecting, predicting, and/or classifying one or more patient conditions, such as stroke or seizure. In some examples, processing circuitry 402 may be configured to calculate parameter values relating to one or more signals received from the electrodes 418, and/or signals from sensors 414. In some examples, processing circuitry 402 may be configured to algorithmically determine the presence or absence of a patient condition, whether the patient has a supra-threshold risk of a condition, or whether a condition is most likely a certain type or has a certain cause, based on the parameter values.

In some examples, sensing circuitry 406 senses a brain signal via electrodes 418. The brain signal may represent the electrical activity of the brain, and may be an EEG. As described herein, processing circuitry 402 may determine parameter values from the brain signal, such values determined based on magnitudes of the signal in one or more frequency bands. Sensing circuitry 406 may include filters and other circuitry to isolate the brain signal of interest.

In some examples, sensing circuitry 406 senses a cardiac signal, and processing circuitry 402 may determine parameter values from the cardiac signal. Example parameter values as described herein, such as heart rate or heart rate variability, may be determined based on detection of occurrence of cardiac beats in the cardiac signal. Sensing circuitry 406 may be configured to sense a variety of different signals within which cardiac beats may be identified and values of cardiac parameters may be determined.

For example, sensing circuitry 406 may be configured to sense a cardiac signal representing the electrical activity (e.g., depolarizations and repolarizations) of the heart, such as a subcutaneous ECG signal, via electrodes 418. As another example, sensing circuitry 406 may be configured to sense a cardiac signal representing mechanical activity of the heart via electrodes 418. A component of a signal sensed via electrodes 418, e.g., on or under the scalp of the patient, may vary based on vibration, blood flow, or impedance changes associated with cardiac contractions. Filtering to isolate this component may include 0.5 to 3 Hz bandpass filtering, although other filtering types, ranges, and cutoffs are possible. In some examples, sensing circuitry 406 may be configured to sense a cardiac signal representing mechanical activity of the heart via other sensors 414, such as optical sensors 291, 363, pressure sensors, or motion sensors 416.

For example, sensing circuitry 406 and/or processing circuitry 402 may detect cardiac pulses via an optical sensor 291, 363. Processing circuitry 402 may determine heart rate or heart rate variability based on the detection of cardiac pulses via optical sensor 291, 363, e.g., in combination with an ECG signal or in the absence of an ECG signal, such as if ECG signal quality is poor. A signal from optical sensor 291, 363 may additionally or alternatively be used for other purposes, such as to determine blood oxygenation, local tissue perfusion, or a surrogate for blood pressure, e.g., PTT, any of which may be useful for detection or prediction of stroke and/or discrimination of ischemic and hemorrhagic stroke.

One or more electrodes 418 may be positioned, e.g., during implantation of sensor device 400, to facilitate sensing of a cardiac signal via the electrodes. In some examples, sensor device 400 may include one or more electrode extensions 265, 272, 276, 284, 285, 286 to facilitate positioning of one or more electrodes 418, e.g., via tunneling under the scalp, at desired locations for sensing the brain and/or cardiac signals. Desired locations for sensing brain and cardiac signals using electrodes 418 may be determined prior to implantation of sensor device 406 for a particular patient using external sensing equipment, such as standard multi-electrode ECG and EEG equipment, either on the particular patient, or experimentally on a number of subjects. In some examples, the one or more housing-based electrodes 418 of sensor device 400 are positioned at a desired location for sensing a brain signal and the one or more extension-based electrodes 418 are positioned at a desired location for sensing a cardiac signal, or vis-a-versa. With reference to FIG. 1C, example locations for positioning an electrode for sensing cardiac signals include P3, PQ3, PQ7, F3, F2, AF3, or C2. In some examples, one or more sensors 414, such as optical sensor 291, 363 may be positioned on an extension.

In some examples, processing circuitry 402 may utilize both electrical, e.g., ECG, and pulsatile cardiac signals in an integrated fashion for the detection, prediction, and/or classification of conditions. In some examples, such integration may result in an "enhanced" ECG signal. For example, processing circuitry 402 may identify features within an ECG signal based on the timing of pulses in a pulsatile signal. In some examples, processing circuitry 402 may account for a delay in pulsatile timing relative to the ECG in such integration.

For example, a signal from optical sensor 291, 363 (e.g., a photoplethysmographic signal) can be used as a timing base for ensemble averaging or other means to improve the signal-to-noise ratio for a cardiac signal. The optical sensor signal can therefore be considered a surrogate cardiac signal and/or be used to derive an enhanced cardiac signal, which may be particularly useful when the ECG has poor quality. A first or second derivative of an optical sensor signal can be used as a trigger for ensemble averaging, e.g., the ECG signal, by, for example, determining the time associated with a maximum/minimum value of the first or second derivative and/or a zero-crossing of the first or second derivative. Sharp, high-frequency points can be used as trigger points to increase the resolution of the ensemble signal, whereas lower-frequency trigger points may smear or distort the ensemble average. The cardiac waveforms that are aligned with the trigger points can be stored and averaged to generate the ensemble signal.

In some examples, processing circuitry 402 may employ patient movement information as a part of the detection, prediction, and/or classification of conditions. For example, motion sensor 416 may include one or more accelerometers configured to detect patient movement. Processing circuitry 402 or sensing circuitry 406 may determine whether or not a patient has fallen based on the patient movement data collected via the accelerometer. Fall detection can be particularly valuable when assessing potential stroke patients, as a large percentage of patients admitted for ischemic or hemorrhagic stroke have been found to have had a significant fall within 15 days of the stroke event. Accordingly, in some embodiments, the processing circuitry 402 can be configured to initiate or modify a stroke detection or prediction algorithm upon fall (or near fall) detection using the accelerometer. In addition to fall detection, motion sensor 416 can be used to determine potential body trauma due to sudden acceleration and/or deceleration (e.g., a vehicular accident, sports collision, concussion, etc.). These events could be thrombolytic, a precursor to stroke. Similar to stroke determination, these fall determinations or other movements can be employed by processing circuitry 402 when detecting, predicting, or classifying a seizure. For example, sensors 414 may detect head movement frequency indicative of a seizure, or detect other patient motion (or absence thereof) indicative of whether a seizure is or is not epileptic in origin.

Figure 5:
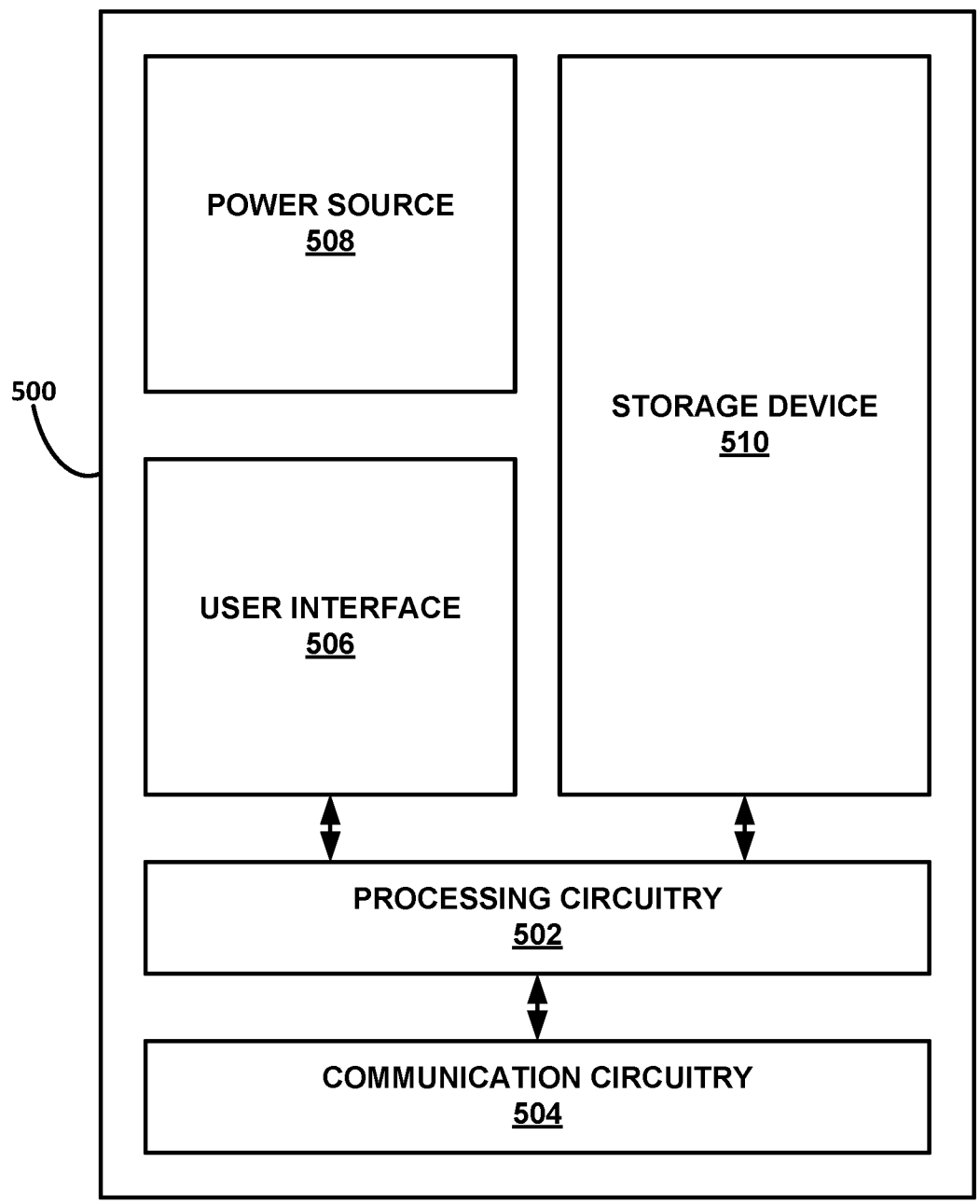
FIG. 5 is a block diagram of an example configuration of an external device configured to communicate with the sensor device of FIG. 4.

FIG. 5 is a block diagram of an example configuration of an external device 500 configured to communicate with any sensor device (e.g., sensor device 106 or sensor device 400) described herein. External device 500 is an example of external device 108 of FIG. 1A. In the example of FIG. 5, external device 500 includes processing circuitry 502, communication circuitry 504, storage device 510, user interface 506, and power source 508.

Processing circuitry 502, in one example, may include one or more processors that are configured to implement functionality and/or process instructions for execution within external device 500. For example, processing circuitry 502 may be capable of processing instructions stored in storage device 510. Processing circuitry 502 may include, for example, microprocessors, GPUs, TPUs, DSPs, ASICs, FPGAs, or equivalent discrete or integrated logic circuitry, or a combination of any of the foregoing devices or circuitry. Accordingly, processing circuitry 502 may include any suitable structure, whether in hardware, software, firmware, or any combination thereof, to perform the functions ascribed herein to processing circuitry 502. Processing circuitry 502 may be an example of or component of processing circuitry 110 (FIGS. 1A and 1B).

Communication circuitry 504 may include any suitable hardware, firmware, software or any combination thereof for communicating with another device, such as IMD 400. Under the control of processing circuitry 502, communication circuitry 504 may receive downlink telemetry from, as well as send uplink telemetry to, sensor device 400, or another device.

Storage device 510 may be configured to store information within external device 500 during operation. Storage device 510 may include a computer-readable storage medium or computer-readable storage device. In some examples, storage device 510 includes one or more of a short-term memory or a long-term memory. Storage device 510 may include, for example, RAM, dynamic random access memories (DRAM), static random access memories (SRAM), magnetic discs, optical discs, flash memories, or forms of electrically programmable memories (EPROM) or EEPROM. In some examples, storage device 510 is used to store data indicative of instructions for execution by processing circuitry 502. Storage device 510 may be used by software or applications running on external device 500 to temporarily store information during program execution.

Data exchanged between external device 500 and sensor device 400 may include operational parameters. External device 500 may transmit data including computer readable instructions which, when implemented by sensor device 400, may control sensor device 400 to change one or more operational parameters and/or export collected data. For example, processing circuitry 502 may transmit an instruction to sensor device 400 which requests sensor device 400 to export collected data (e.g., data corresponding to one or more of the sensed signals, parameter values determined based on the signals, or indications that a condition has been detected, predicted, or classified) to external device 500. In turn, external device 500 may receive the collected data from sensor device 400 and store the collected data in storage device 510.

A user, such as a clinician or patient 102, may interact with external device 500 through user interface 506. User interface 506 includes a display (not shown), such as an LCD or LED display or other type of screen, with which processing circuitry 502 may present information related to IMD 400 (e.g., stroke and/or seizure metrics). In addition, user interface 506 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 502 of external device 500 and provide input. In other examples, user interface 506 also includes audio circuitry for providing audible notifications, instructions or other sounds to patient 102, receiving voice commands from patient 102, or both. Storage device 510 may include instructions for operating user interface 506 and for managing power source 508.

Power source 508 is configured to deliver operating power to the components of external device 500. Power source 508 may include a battery and a power generation circuit to produce the operating power. In some examples, the battery is rechargeable to allow extended operation. Recharging may be accomplished by electrically coupling power source 508 to a cradle or plug that is connected to an alternating current (AC) outlet. In addition, recharging may be accomplished through proximal inductive interaction between an external charger and an inductive charging coil within external device 500. In other examples, traditional batteries (e.g., nickel cadmium or lithium ion batteries) may be used. In addition, external device 500 may be directly coupled to an alternating current outlet to operate.

In some examples, external device 500 may provide an alert to the patient or another entity (e.g., a call center) based on a condition detection, prediction, or classification provided by sensor device 400. In some examples, user interface 506 may provide an interface for presenting an alert of the detection, prediction, or classification of the condition, e.g., stroke, and for a user, e.g., the patient, a caregiver, or a clinician, to provide input overriding the detection, prediction, or classification. In this manner, systems as described herein may avoid unnecessary emergency activity resulting from a false detection by the system. Additionally or alternatively, external device 500 may output user prompts which can be synchronized with data collection via sensor device 400. For example, external device 500 may instruct the user to lift an arm, make a facial expression, etc., and sensor device 400 may record physiological data while the user performs the requested actions. Moreover, external device 500 may itself analyze the patient (e.g., the patient's activity or condition in response to such prompts), for example using a camera to detect facial drooping, using a microphone to detect slurred speech, or to detect any other indicia of stroke. In some embodiments, such indicia can be compared against pre-stroke inputs (e.g., a stored baseline facial image or voice-print with baseline speech recording). Similarly, external device 500 may user one or more sensors to detect patient movement or facial activity to provide data indicative of a seizure or upcoming seizure.

Figure 6:
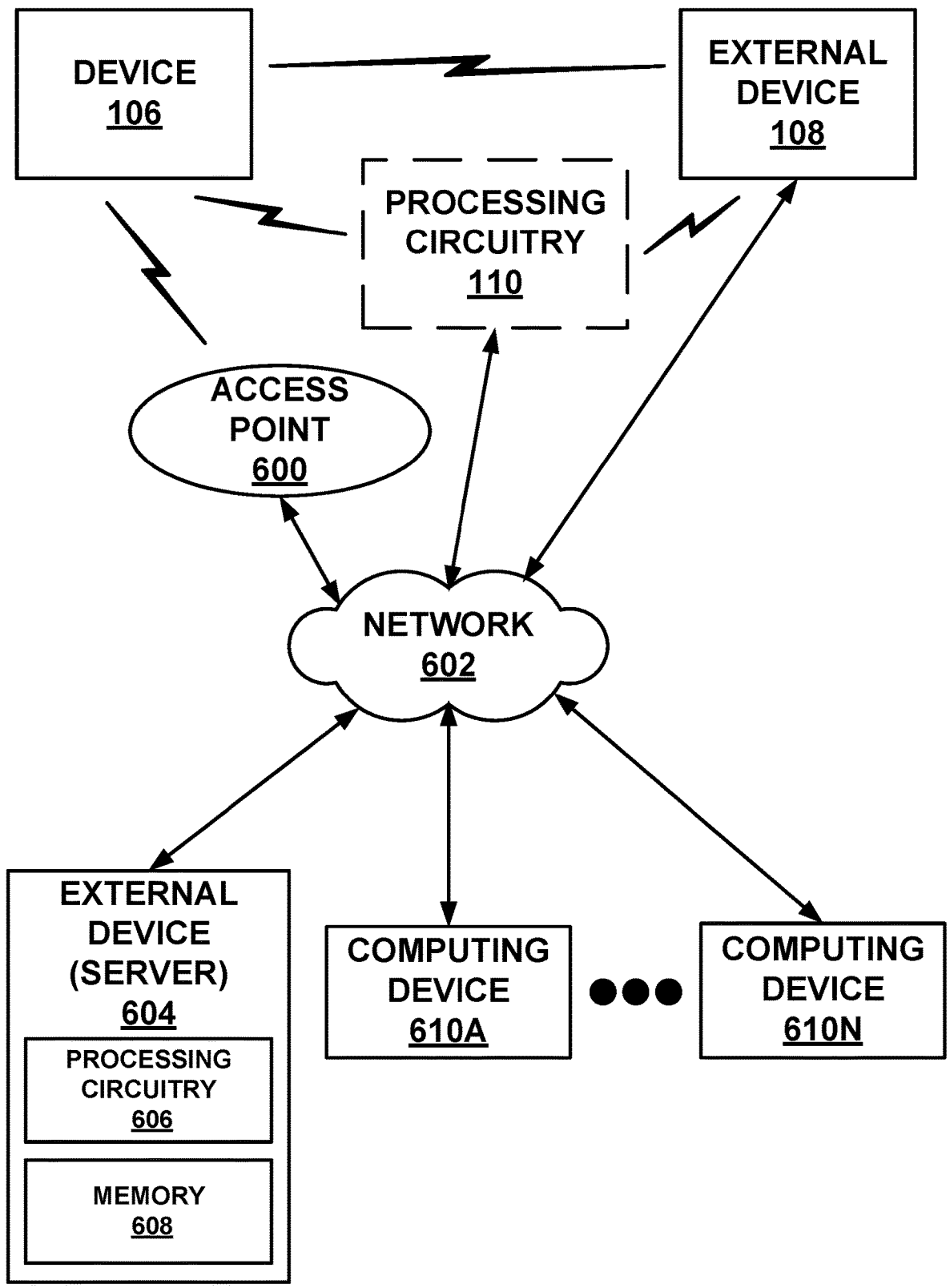
FIG. 6 is a block diagram illustrating an example system that includes an access point, a network, external computing devices, such as a server, and one or more other computing devices, which may be coupled to sensor, the external device, and the processing circuitry of FIG. 1 via a network, in accordance with one or more techniques described herein.

FIG. 6 is a block diagram illustrating an example system that includes an access point 600, a network 602, external computing devices, such as a server 604, and one or more other computing devices 610A-610N, which may be coupled to sensor device 106, external device 108, and processing circuitry 110 via network 602, in accordance with one or more techniques described herein. In this example, sensor device 106 may use communication circuitry to communicate with external device 108 via a first wireless connection, and to communication with an access point 600 via a second wireless connection. In the example of FIG. 6, access point 600, external device 108, server 604, and computing devices 610A-610N are interconnected and may communicate with each other through network 602.

Access point 600 may include a device that connects to network 602 via any of a variety of wired or wireless network connections. In some examples, access point 600 may be a user device, such as a tablet or smartphone, that may be co-located with the patient. As discussed above, sensor device 106 may be configured to transmit data, such as signals, parameter values determined from signals, or condition/classification indications, to external device 108. In addition, access point 600 may interrogate sensor device 106, such as periodically or in response to a command from the patient or network 602, in order to retrieve such data from sensor device 106, or other operational or patient data from sensor device 106. Access point 600 may then communicate the retrieved data to server 604 via network 602.

In some cases, server 604 may be configured to provide a secure storage site for data that has been collected from sensor device 106, and/or external device 108. In some cases, server 604 may assemble data in web pages or other documents for viewing by trained professionals, such as clinicians, via computing devices 610A-610N. One or more aspects of the illustrated system of FIG. 6 may be implemented with general network technology and functionality, which may be similar to that provided by the Medtronic CareLink® Network developed by Medtronic plc, of Dublin, Ireland.

Server 604 may include processing circuitry 606. Processing circuitry 606 may include fixed function circuitry and/or programmable processing circuitry. Processing circuitry 606 may include any one or more of a microprocessor, a GPU, a TPU, a controller, a DSP, an ASIC, an FPGA, or equivalent discrete or analog logic circuitry. In some examples, processing circuitry 606 may include multiple components, such as any combination of one or more microprocessors, one or more controllers, one or more DSPs, one or more ASICs, or one or more FPGAs, as well as other discrete or integrated logic circuitry. The functions attributed to processing circuitry 606 herein may be embodied as software, firmware, hardware or any combination thereof. In some examples, processing circuitry 606 may perform one or more techniques described herein based on sensed signals and/or parameter values received from sensor device 106. For example, processing circuitry 606 may perform one or more of the techniques described herein to detect, predict, and/or classify one or more patient conditions.

Server 604 may include memory 608. Memory 608 includes computer-readable instructions that, when executed by processing circuitry 606, cause server 604 and processing circuitry 606 to perform various functions attributed to server 604 and processing circuitry 606 herein. Memory 608 may include any volatile, non-volatile, magnetic, optical, or electrical media, such as RAM, ROM, NVRAM, EEPROM, flash memory, or any other digital media.

In some examples, one or more of computing devices 610A-610N (e.g., device 610A) may be a tablet or other smart device located with a clinician, by which the clinician may program, receive alerts from, and/or interrogate sensor device 106. For example, the clinician may access data corresponding to any one or combination of sensed physiological signals, parameters, or indications of detected, predicted, or classified conditions collected by sensor device 106. In some examples, the clinician may enter instructions for a medical intervention for patient 102 into an app in device 610A, such as based on a status of a patient condition determined by sensor device 106, external device 108, processing circuitry 110, or any combination thereof, or based on other patient data known to the clinician. Device 610A then may transmit the instructions for medical intervention to another of computing devices 610A-610N (e.g., device 610B or external device 108) located with patient 102 or a caregiver of patient 102. For example, such instructions for medical intervention may include an instruction to change a drug dosage, timing, or selection, to schedule a visit with the clinician, or to seek medical attention. In further examples, device 610B may generate an alert to patient 102 based on a status of a medical condition of patient 102 determined by sensor device 106, which may enable patient 102 proactively to seek medical attention prior to receiving instructions for a medical intervention. In this manner, patient 102 may be empowered to take action, as needed, to address his or her medical status, which may help improve clinical outcomes for patient 102.

Figure 7:
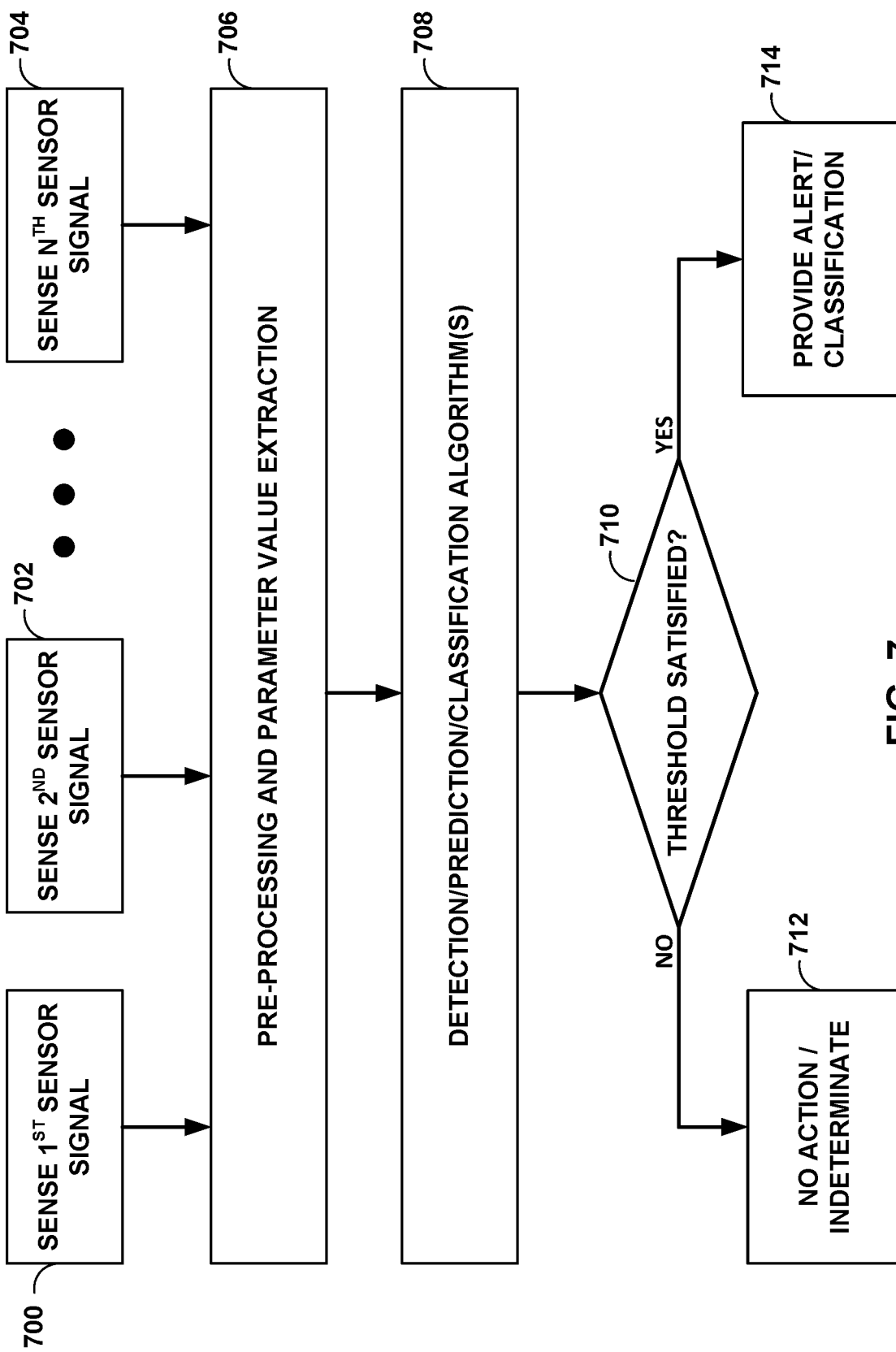
FIG. 7 is a flow diagram illustrating an example technique for generating at least one of a detection, prediction, or classification of a patient condition based on information from multiple sensors.

FIG. 7 is a flow diagram illustrating an example technique for generating at least one of a detection, prediction, or classification of a patient condition based on information from multiple sensors of a sensor device, such as sensor devices 106, 210, 220, 310, 400, which are disposed at the neck, lower back of the head, or otherwise above the shoulders of a patient. The example technique of FIG. 7 is described as being performed by sensor device 400 and processing circuitry 110, but may be performed by any sensor device described herein, e.g., which may be configured as illustrated with respect to sensor device 400 in FIG. 4. As described herein, processing circuitry 110 may include processing circuitry of any one or more devices described herein, such as processing circuitry 402 of sensor device 400, processing circuitry 502 of external device 500, or processing circuitry 606 or server 604.

Sensor device 400 includes one or more sensors, such as electrodes 418 and sensors 414. According to the example illustrated by FIG. 7, sensing circuitry 406 of sensor device 400 senses one or more signals using the one or more sensors (700, 702, 704). For examples, sensing circuitry 406 may sense one or more signals via electrodes 418. The signals may include a brain signal (e.g., an EEG signal) and a cardiac or heart signal (e.g., an ECG signal or cardiac mechanical signal). In some examples, sensing circuitry 406 separates the brain and heart signals sensed via each of multiple sensing vectors using the techniques described in commonly-assigned U.S. Provisional Patent Application No. 63/071,908, filed on Aug. 28, 2020, and titled "DETERMINING COMPOSITE SIGNALS FROM AT LEAST THREE ELECTRODES", the entire content of which is incorporated herein by reference. The sensed signals may also include a motion signal sensed by motion sensor 416, e.g., one or more accelerometers. The sensed signals may also include respiration signals, skin impedance signals, and/or perfusion signals (e.g., sensed via impedance using electrodes 418), blood pressure signals (e.g., PTT or other surrogate blood pressure signals sensed via photoplethysmography using optical sensors 291, 363), heart sound signals (e.g., sensed using motion sensor 416 or an acoustic sensor), or ballistocardiogram signals (e.g., sensed using the ECG and motion sensor signals).

The signals, or parameters derived therefrom, may be useful for detecting, predicting, or classifying any of a number of patient conditions. For example, brain and cardiac signals may be useful for detecting or predicting stroke and/or seizures. Motion and posture of the patient may further improve the ability of processing circuitry 110 to detect, predict, and classify patient conditions. For example, posture has an important impact on cardiovascular stress and the autonomic nervous system, which may precipitate certain conditions. Motion, respiration and other sensor signals may capture clinical symptoms that may be present during stroke, epileptic seizure, and other neurological and/or cardiac events, and differentiate between different conditions, or types or origins of a particular condition. Additional parameters and signals may improve the sensitivity and specificity of the detection, prediction, and/or classification by processing circuitry 110.

The example technique of FIG. 7 further includes pre-processing and parameter value extraction, which may be performed by sensing circuitry 406 and/or processing circuitry 110 (706). Pre-processing may include any of a variety of analog and/or digital filtering or other signal processing techniques to allow ready extraction of values of the desired features or parameters from a signal.

According to the example of FIG. 7, processing circuitry 110 applies one or more detection, prediction, and/or classification algorithms to the parameter values and/or signals to detect, predict, and/or classify one or more patient conditions (708). In some examples, a result of the algorithm is a probability, e.g., risk of the condition, and processing circuitry 110 may determine if the probability satisfies, e.g., is greater than or equal to, a threshold (710). If the threshold is not satisfied (NO of 710), processing circuitry 110 may not provide an alert and/or may indicate an indeterminate classification of a patient condition (712). If the threshold is satisfied (YES of 710), processing circuitry 110 may provide an alert and/or classification of a patient condition (714), e.g., to or via external device 108 or another computing device described herein.

The algorithms applied by processing circuitry 110 may be derived by applying machine learning and/or neural network techniques to databases of patient data (e.g., parameter and signal values) having the condition or classification. The determination by such algorithms may be binary or probabilistic. Classification algorithms may include an etiology classifier that can make a determination (probabilistic or definitive) of the origin or type of the condition (e.g., ischemic or hemorrhagic, or which hemisphere, for stroke).

Figure 8:
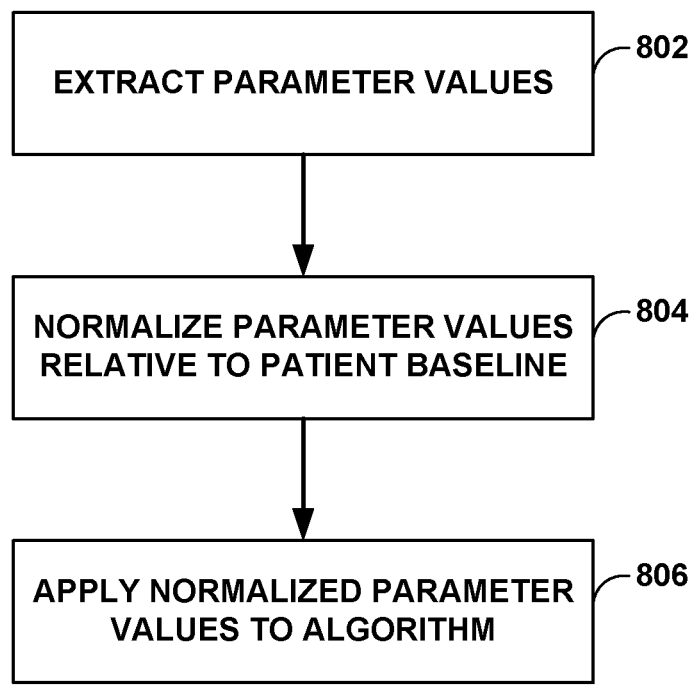
FIG. 8 is a flow diagram illustrating example operations in a technique for generating at least one of a detection, prediction, or classification of a patient condition based on information from multiple sensors.

FIG. 8 is a flow diagram illustrating example operations in a technique for generating at least one of a detection, prediction, or classification of a patient condition based on information from multiple sensors. The example technique of FIG. 8 is described as being performed by sensor device 400 and processing circuitry 110, but may be performed by any sensor device described herein, e.g., which may be configured as illustrated with respect to sensor device 400 in FIG. 4. As described herein, processing circuitry 110 may include processing circuitry of any one or more devices described herein, such as processing circuitry 402 of sensor device 400, processing circuitry 502 of external device 500, or processing circuitry 606 or server 604.

The example techniques of FIG. 8 may generally correspond to the pre-processing and parameter value extraction (706) described with respect to the example technique of FIG. 7. According to the example method of FIG. 8, processing circuitry 110 extracts parameter values from one or more of the signals sensed by sensor device 400 (802). Example parameter values that may be extracted from brain and cardiac signals are discussed in further detail herein. The extraction may result in a time series of values for each of one or more parameters. The detection, prediction, and classification algorithms used by processing circuitry 110 may consider a single (e.g., current) value of a given parameter, or multiple values of the parameter over time.

Processing circuitry 804 may further normalize one or more parameter values relative to a baseline value for the patient (804). The baseline value may be derived from values of the parameter determined for the patient in the past, such as an average of values preceding the current value by a certain amount of time, or from a certain baseline or learning period in the past. Normalizing may include any comparative or mathematical operation using the determined and baseline values, such as a difference operation. Processing circuitry 110 may apply the normalized parameter values to an algorithm for detecting, predicting, or classifying a patient condition (806). Normalization of the parameter values may allow processing circuitry 110 to account for patient-to-patient variation in the parameter values that are not probative of the probability or risk of a particular condition or classification. This may, in turn, enhance the sensitivity and specificity at which processing circuitry is able to detect, predict, and/or classify conditions.

Figure 9:
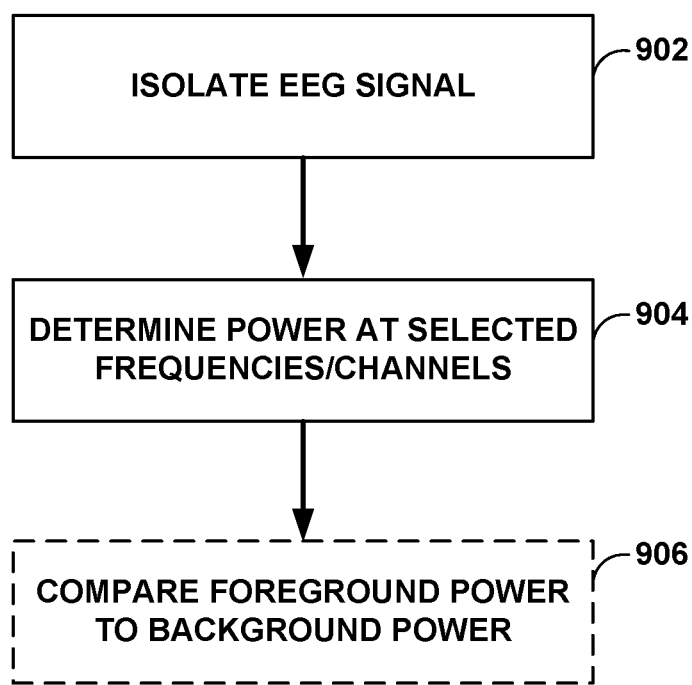
FIG. 9 is a flow diagram illustrating example technique for determining values of one or more parameters based on a brain signal.

FIG. 9 is a flow diagram illustrating example technique for determining values of one or more parameters based on a brain electrical signal. The example technique of FIG. 9 is described as being performed by sensor device 400 and processing circuitry 110, but may be performed by any sensor device described herein, e.g., which may be configured as illustrated with respect to sensor device 400 in FIG.

4. As described herein, processing circuitry 110 may include processing circuitry of any one or more devices described herein, such as processing circuitry 402 of sensor device 400, processing circuitry 502 of external device 500, or processing circuitry 606 or server 604.

According to the example of FIG. 9, sensing circuitry 406 of sensor device 400 isolates an EEG or other brain electrical signal from one or more electrical signal sensed via electrodes 418 (902). Example techniques for isolating an EEG signal are described in previously-incorporated U.S. Provisional Patent Application No. 63/071,908, filed on Aug. 28, 2020, and titled "DETERMINING COMPOSITE SIGNALS FROM AT LEAST THREE ELECTRODES", , and U.S. Provisional Patent Application No. 62/997,503, filed Feb. 17, 2020, the entire content of which is incorporated herein by reference.

According to the example of FIG. 9, processing circuitry 110 further determines a power of the brain electrical signal within certain selected frequency bands (904). In some examples, processing circuitry 110 optionally compares a foreground power to a background power for one or more of the frequency bands (e.g., a current power to a previous power), and/or compares the power of two or more bands to each other. The power within the frequency bands, or results of such comparisons, may be parameter values for one or more algorithms to detect, predict, and/or classify a patient condition.

Techniques for determining power within certain frequency bands as parameter values for determining a patient condition, such as stroke, are described in previously-incorporated U.S. Provisional Patent Application No. 63/071,908, filed on Aug. 28, 2020, and titled "DETERMINING COMPOSITE SIGNALS FROM AT LEAST THREE ELECTRODES". Techniques for determining power within certain frequency bands and comparing foreground and background power to detect seizures or other nervous system conditions are described in U.S. Pat. No. 8,068,903, issued to Virag et al. on Nov. 29, 2011, which is incorporated herein by reference in its entirety.

Figure 10:
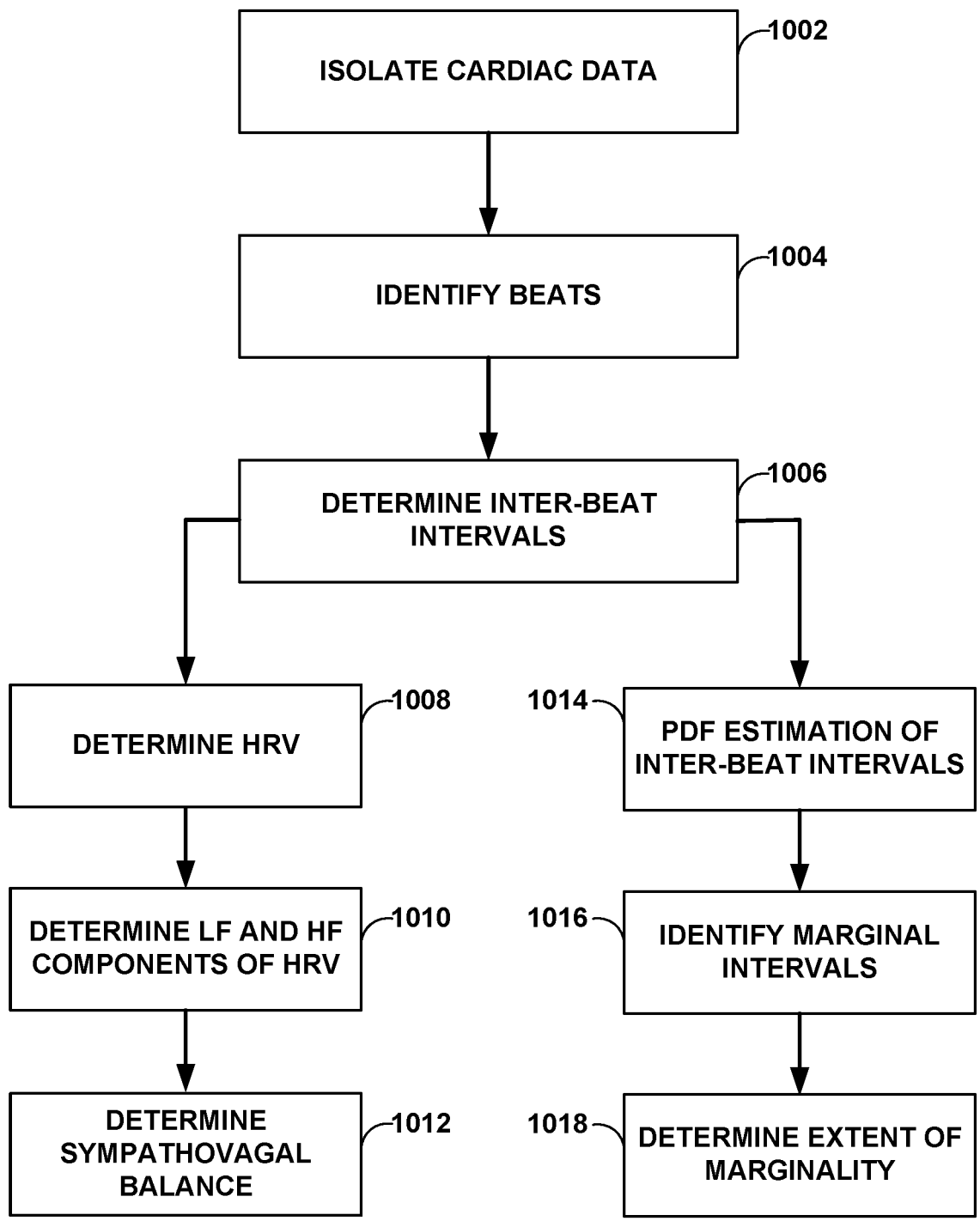
FIG. 10 is a flow diagram illustrating an example technique for determining values of values of one or more parameters based on a cardiac signal.

FIG. 10 is a flow diagram illustrating an example technique for determining values of one or more parameters based on a cardiac electrical signal. The example technique of FIG. 10 is described as being performed by sensor device 400 and processing circuitry 110, but may be performed by any sensor device described herein, e.g., which may be configured as illustrated with respect to sensor device 400 in FIG. 4. As described herein, processing circuitry 110 may include processing circuitry of any one or more devices described herein, such as processing circuitry 402 of sensor device 400, processing circuitry 502 of external device 500, or processing circuitry 606 or server 604.

According to the example of FIG. 10, sensing circuitry 406 of sensor device 400 isolates an ECG or other cardiac signal, or generates an integrated signal or enhanced ECG signal, from one or more electrical signals sensed via electrodes 418 and/or other sensors (1002). Example techniques for isolating an ECG signal are described in previously-incorporated U.S. Provisional Patent Application No. 63/071,908, filed on Aug. 28, 2020, and titled "DETERMINING COMPOSITE SIGNALS FROM AT LEAST THREE ELECTRODES".

Sensing circuitry 406 and/or processing circuitry 110 may further identify beats within the cardiac signal (1004). Beats may be identified using known techniques, such as identification of the occurrence and timing of R-waves or other features of the QRS complex, or detection of peaks is a signal indicative of mechanical activity of the heart. Processing circuitry 110 may then determine inter-beat intervals (1006), e.g., the duration of time between consecutive beats. Processing circuitry 110 may then determine values of a number of parameters based on the determined inter-beat intervals.

For example, processing circuitry 110 may determine heart rate variability (HRV) values based on the inter-beat intervals (1008). Processing circuitry 110 may determine HRV based on a Lorenz plot of inter-beat intervals, in some examples. HRV may change (increase or decrease) during or preceding certain patient conditions. These changes may be due to changes in the autonomic function or state of the patient. HRV values may be examples of parameter values.

In some examples, processing circuitry 110 may transform HRV values to the frequency domain and determine relatively lower frequency (LF) and higher frequency (HF) components of the HRV values (1010). The LF and HF values of HRV may be examples of parameter values. In some examples, processing circuitry 110 may determine a ratio between or otherwise compare the LF and HF components of HRV, which may indicate a sympatho-vagal balance of patient (1012). Values resulting from such a comparison may be another example of values of a parameter over time. In some examples, processing circuitry 110 may assess HRV with a parametric spectral estimation using a sliding analysis window, e.g., of 60-240 seconds, shifted, e.g., with 5-20 second increments. Processing circuitry 110 may compute the sympatho-vagal balance as the ratio of the LF components (e.g., 0.04 Hz-0.15 Hz, mainly sympathetic activity) versus the HF components (e.g., 0.15-0.4 Hz, mainly parasympathetic activity).

As another example, processing circuitry 110 may determine a power density function (PDF) estimation of the inter-beat intervals (1014). Processing circuitry 110 may then identify marginal intervals amongst the inter-beat intervals used in the PDF estimation (1016), and determine an extent of marginality (1018). A numeric representation of the extent of marginality is an example of a parameter value. Marginal intervals, e.g., RR intervals, reflect cardiac hyperexcitability, and may be analyzed using a statistical assessment of the percentage or other portion of inter-beat intervals outside a confidence interval (e.g., window size of 40 beats). Processing circuitry 110 may determine or estimate the statistical distribution of these inter-beat intervals over a period of time, such as the last six minutes, and determine the number of ectopic and marginal events. The statistical distribution may be estimated de-trending, e.g., after third-order polynomial trend removal.

Marginality may increase prior to syncope and epileptic seizure events, e.g., in a time frame between 30 minutes to 2 hours prior to the syncope/seizure. Marginality reflects several non-coordinated chronotropic responses. Under normal baseline conditions, the marginality is very low. A higher marginality is observed in syncopal events, which consists mainly of ectopic beats. On the other hand, seizures are often preceded or accompanied by a considerable higher marginality, notably abrupt tachycardia, only rarely bradycardia. Some clinical studies have reported a lock-step phenomenon defined as the occurrence of cardiac sympathetic and parasympathetic neural discharges intermittently synchronized with epileptogenic discharges (fluctuations in cardiac autonomic activity). Thus, processing circuitry 110 may use parameter values indicative of marginality for a variety of purposes, including detecting or predicting seizure and/or syncope, and classifying events as one of seizure or syncope. Techniques for using marginality to distinguish epileptic seizure and neurogenic or cardiogenic syncope are described in U.S. Pat. No. 8,738,121, which issued to Virag et al. on May 27, 2014, and is incorporated herein by reference in its entirety.

In some examples, processing circuitry 110 may additionally or alternatively identify significant decreases in inter-beat intervals, such as a largest decrease during a predetermined period of time, e.g., 60 seconds. The increased magnitude of such reductions may precede certain patient conditions, such as syncope or epileptic seizure. Magnitudes of such reductions over time may be values over time of a parameter used by processing circuitry 110 to detect, predict, or classify such conditions. In some examples, processing circuitry 110 may additionally or alternatively identify tachyarrhythmias based on the inter-beat intervals. The number, duration, etc. of tachyarrhythmias may be values over time of a parameter used by processing circuitry 110 to detect, predict, or classify such conditions.

Reliable automatic detection/anticipation of epileptic seizures is a necessary first step for preventive therapeutic treatment (pacing or drugs). Over the past decade, numerous studies have addressed the problem of seizure detection/anticipation and a large number of methods have been proposed. The first algorithms based on linear analysis of EEGs (Fourier transform, coherence function, multidimensional autoregressive modeling) allowed only a detection of a few seconds (1-6) before visible symptoms. This anticipation time is however not sufficient to design a closed-loop therapeutic system. Anticipation times of several minutes have been reported for linear techniques based on wavelet transforms, neural nets or nonlinear techniques such as correlation integrals of EEGs. These more complex methods are however facing problems such as optimal feature selection, optimal signal selection in multi-focal epilepsy. They show a high variability in results and an important number of false alarms.

The problems related to existing seizure anticipation algorithms may be linked to a lack of information about the physiological state of the patient. Additional information contained in cardiovascular signals, such as the parameter values derived from a cardiac electrical signal as described above, may increase robustness. Such parameters may include information about the modulation of the autonomic nervous system. Blood pressure signals or signals indicative of a surrogate of blood pressure signals, e.g., PTT, may additionally or alternatively provide information about modulation of the autonomic nervous system. Modulation of the autonomic nervous system may precede syncope and epileptic seizure. Pacing of the vagus nerve has been applied to prevent epileptic seizures, and it is very likely that changes in nervous system of the patient may be necessary to permit initiation of spontaneous focal seizures.

Algorithms that utilize both brain and cardiac signals to detect, predict, and/or classify epileptic seizure or other mimics thereof, such as syncope and psychogenic attack may be more reliable than existing algorithms using only one of these types of signals. Processing circuitry 110 may assess EEG features as described above to identify early appearance of synchrony/coherence, while cardiac features may reveal cardiogenic origins.

The use of a combination of brain, cardiac, and other signals as described herein may allow classification of conditions thought to be seizures, e.g., to distinguish seizures from other conditions that may mimic seizures. For example, analysis of cardiac derived parameters immediately before and during a blackout may be able to define distinct patterns, or "signatures," which can be used to distinguish syncope, epilepsy and psychogenic attacks, the three most common causes of blackouts.

There are recognized difficulties in making a diagnosis of a cause of blackout. Routine EEG recordings are often unhelpful. Only small numbers of patients can be admitted for prolonged monitoring and it is unrealistic to recording prolonged EEG for more than 48 hours without admission to hospital. Consideration of cardiac and other parameters to perform such a classification of the suspected seizure or blackout according to the techniques described herein may avoid unnecessary admission to a hospital for prolonged Epilepsy Monitoring Unit (EMU) monitoring.

Figure 11:
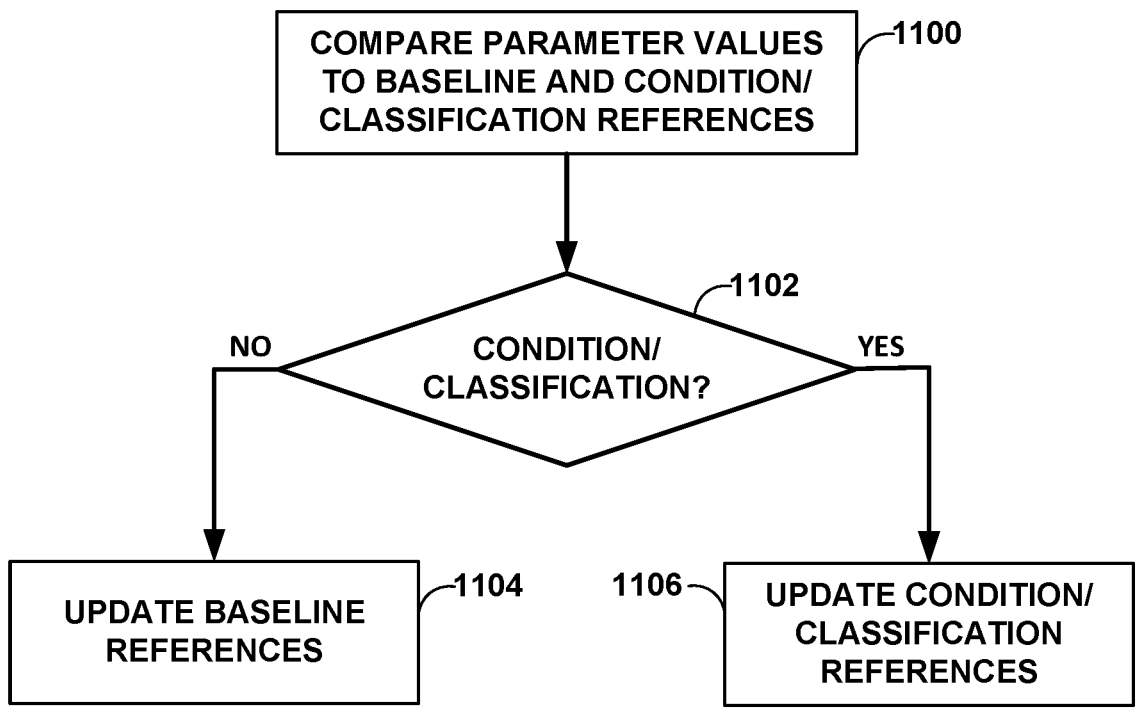
FIG. 11 is a flow diagram illustrating an example technique for updating baseline and condition reference values for one or more parameters.

FIG. 11 is a flow diagram illustrating an example technique for updating baseline and condition reference values for one or more parameters. The example technique of FIG. 11 is described as being performed by processing circuitry 110. As described herein, processing circuitry 110 may include processing circuitry of any one or more devices described herein, such as processing circuitry 402 of sensor device 400, processing circuitry 502 of external device 500, or processing circuitry 606 or server 604.

According to the example of FIG. 11, as part of an algorithm for detecting, predicting, and/or classifying a patient condition, processing circuitry 110 compares the determined parameter values, e.g., determined from brain and cardiac electrical signals, to at least two different sets of reference values (1100). One of the sets of reference values is a baseline set of reference values, and the other is a set of reference values for the condition to be detected or predicted, or for the classification. The reference values in both sets may initially be determined based on databases of parameter values that are from individuals other than the patient and are known to be representative of the condition/classification or the absence thereof (baseline), e.g., using machine learning and/or neural network techniques. In some examples, the reference and current sets of parameter values may be Eigenvectors.

Processing circuitry 110 determines whether the condition is occurring or has occurred, or that the classification is true, based on the comparison of the current parameter values for the patient to both sets of reference values (1102). If processing circuitry 110 determines that the condition is not occurring or has not occurred, or that the classification false, processing circuitry 110 updates that baseline references based on the current parameter values used in the comparison (1104). If processing circuitry 110 determines that the condition is occurring or has occurred, or that the classification true, processing circuitry 110 updates that condition/classification references based on the current parameter values used in the comparison (1106).

In some examples, processing circuitry 110 may determine similarity and dissimilarity measures with respect to both the condition/classification and baseline references, and determine whether the condition is occurring or has occurred, or that the classification is true, based these measures. In some examples, the measures may be discriminant distance (heteroscedastic linear discriminant analysis (LDA)) measures. Such an algorithm may be referred to as a discriminant measure algorithm. Processing circuitry 110 may weight different parameters differently, and may update weights based on reliability, which may be obtained by a statistical analysis of the references. This may allow the algorithm employed by processing circuitry 110 to account for changing physiological states of patient, such as sleep, stress, and physical activity. Regular updating of the reference sets may also allow the algorithm to account for such changing conditions.

Figure 12:
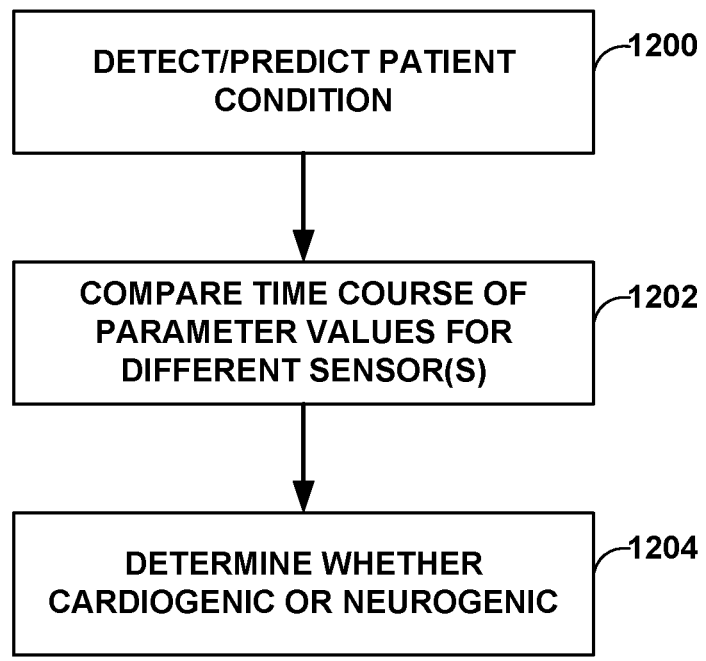
FIG. 12 is a flow diagram illustrating an example technique for determining whether a detected or predicted patient condition is cardiogenic or neurogenic.

FIG. 12 is a flow diagram illustrating an example technique for determining whether a detected or predicted patient condition is cardiogenic or neurogenic. The example technique of FIG. 12 is described as being performed by processing circuitry 110. As described herein, processing circuitry 110 may include processing circuitry of any one or more devices described herein, such as processing circuitry 402 of sensor device 400, processing circuitry 502 of external device 500, or processing circuitry 606 or server 604.

According to the example of FIG. 12, processing circuitry 110 detects or predicts a patient condition, such as a seizure, using any of the example techniques described herein (1200). Processing circuitry 110 further compares a time course of the parameter values derived from different signals sensed by sensor device 400 and used by processing circuitry to detect or predict the condition (1202). For example, processing circuitry 110 may compare parameter values from a brain signal to parameter values from a cardiac signal. Based on the relative timing of parameter value indicative of the condition, processing circuitry 110 may determine whether the condition was cardiogenic or neurogenic.

In some examples, processing circuitry 110 may similarly use a comparison of timing between different signals to identify from which hemisphere of the brain a stroke or seizure emanates. For example, a single sensor device with one or more extensions, or bilateral sensor devices, may position electrodes or other sensors to sense signals from each hemisphere of the brain, e.g., from respective temporal locations. Processing circuitry 110 may compare parameter values from the hemispheres to determine from which hemisphere the condition emanates and/or an extend of electrographic spread.

In some examples, processing circuitry 110 may utilize a timing-based evaluation of brain and cardiac signals to discriminate between ischemic and hemorrhagic stroke. For example, processing circuitry 110 may determine whether increases in heart beat variability determined from a cardiac signal precede or follow changes in the brain signal associated with a stroke. Changes in the brain signal may include suppression of frequency and/or amplitude of the signal, or power in one or more frequency bands. Measures of heart beat variability include heart rate variability, intra-beat interval variability (such as QT interval variability), beat feature morphological variability, ST elevation, or T-wave alternans. Changes in heart beat variability following changes in the brain signal may suggest a hemorrhagic stroke, while changes in the brain signal following changes in heart beat variability may suggest an ischemic stroke.

Figure 13:
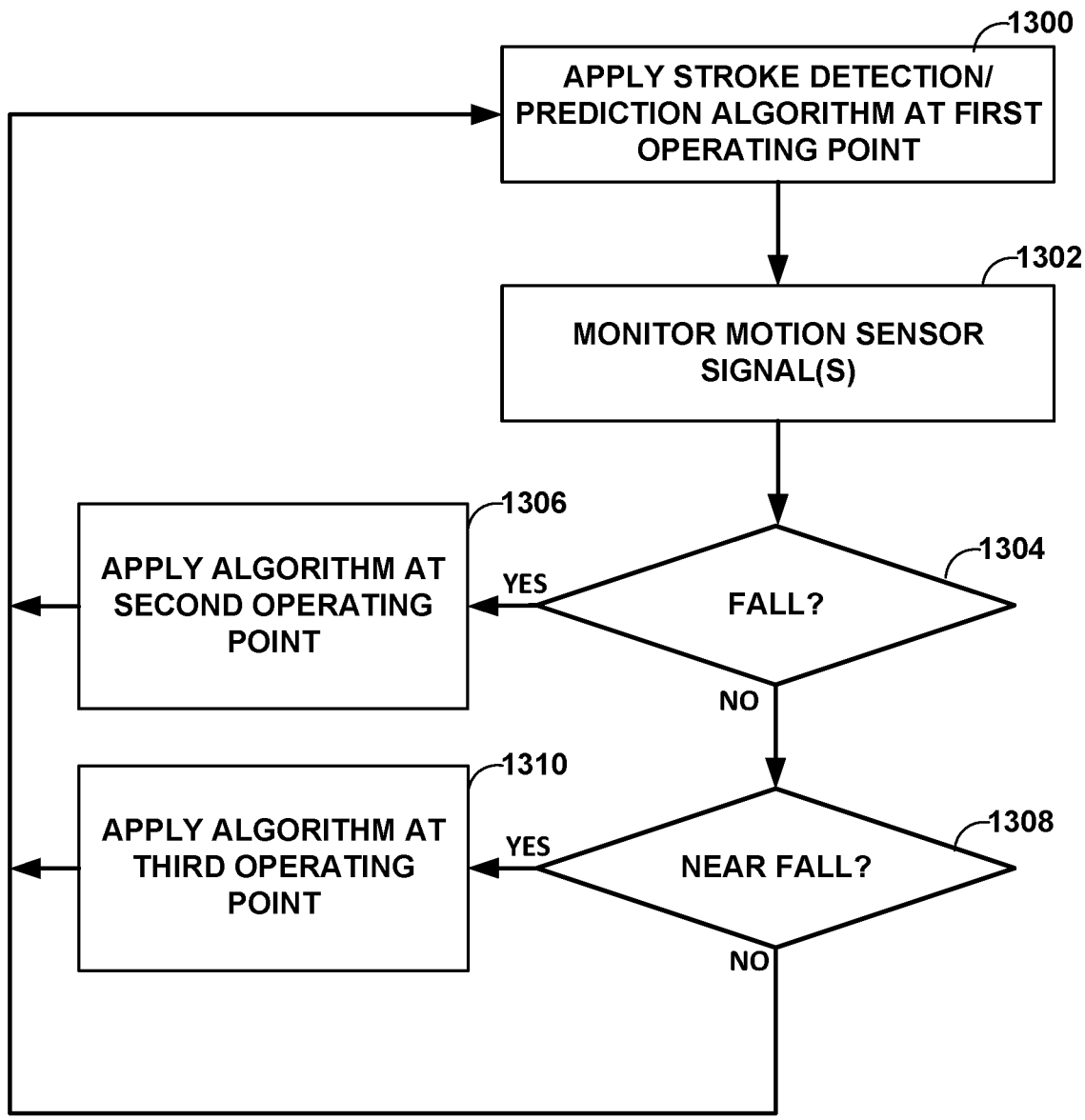
FIG. 13 is a flow diagram illustrating an example technique for adjusting an operating point for a stroke detection/prediction algorithm based on detection of a fall or near fall.

FIG. 13 is a flow diagram illustrating an example technique for adjusting an operating point for a stroke detection/prediction algorithm based on detection of a fall or near fall. The example technique of FIG. 13 is described as being performed by processing circuitry 110. As described herein, processing circuitry 110 may include processing circuitry of any one or more devices described herein, such as processing circuitry 402 of sensor device 400, processing circuitry 502 of external device 500, or processing circuitry 606 or server 604.

According to the example of FIG. 13, processing circuitry 110 applies a stroke detection/prediction algorithm at a first operating point (1300). The operating point for the algorithm may have an associated sensitivity and specificity, which may be affected by values of one or more thresholds, such as a probability threshold for determining that stroke is occurring or sufficiently likely to occur. Processing circuitry 110 also monitors one or more motion signals from motion sensor(s) 416 of sensor device 400 (1302).

Based on the one or more motion signals, processing circuitry 110 determines whether the patient has fallen (1304). If processing circuitry 110 determines that the patient has fallen (YES of 1304), processing circuitry 110 applies the algorithm at a second operating point (1306). The second operating point may have a higher sensitivity and lower specificity than the first operating point. Processing circuitry 110 may adjust the operating point by adjusting parameters of the algorithm, such as lowering a probability threshold for stroke.

If processing circuitry 110 does not determine that the patient has fallen (NO of 1304), processing circuitry 110 may determine whether the patient has experienced a near fall based on the one or more motion signals (1308). If processing circuitry 110 determines that the patient has experienced a near fall (YES of 1308), processing circuitry 110 applies the algorithm at a third operating point (1310). The third operating point may be between the first and second operating points with respect to sensitivity and specificity. If processing circuitry 110 does not determine that the patient has experienced a near fall (NO of 1308), processing circuitry 110 applies the algorithm at the first operating point.

When processing circuitry 110 adjusts the operating point to the second or third operating point, processing circuitry 110 may maintain the adjustment for a period of time, such as a predetermined number of days. Strokes leading to hospitalization are often preceded by falls or near falls, which may have been caused by less severe strokes. The increased sensitivity of the second and third operating points may increase the ability of processing circuitry 110 to identify stroke within the period following a fall or near fall.

Processing circuitry 110 may also use one or more motion signals from motion sensor(s) 416 of sensor device 400 to detect or predict conditions other than stroke. For example, while vasovagal syncope (VVS) and a variety of other conditions may result in cardiac parameter values indicative of a change in sympatho-vagal balance, VVS occurs under orthostatic constraints. Therefore, syncope occurs typically after posture changes, such as supine-to upright. Processing circuitry 110 may use cardiac signals, such as ECG, blood pressure signals, and/or other cardiac mechanical signals, and motion sensor signals to detect, predict, and/or classify syncope.

In some examples, one sensor device 400 may be placed above the shoulders as described herein, and another on the chest for cardiac monitoring. Such a system, or a system having only a sensor device on or near the head, may be configured for evaluating causes of sudden unexplained death (SUDEP) in epilepsy, which are often attributed to neurological and/or cardiac conditions. Separate on-board detection algorithms for each sensor uniquely captures abnormalities (i.e., EEG/ECG), and when merged, may make a determination regarding which occurred first for a given symptom (i.e., brain or heart).

FIG. 14 is a flow diagram illustrating an example technique for determining and implementing a preferential treatment pathway for a patient based on a generated detection, prediction, or classification of a condition of the patient.

According to the example of FIG. 14, external device 500, which may be an example of external device 108, such as a smartphone of the patient, may receive an indication from sensor device 400 that a condition that is an emergency, such as a Large Vessel Occlusion (LVO) stroke, was detected or predicted (1400). External device 500 may determine a location of the patient, e.g., using GPS or cell tower triangulation, in response to receiving the indication of an emergency condition (1402). External device 500 may transmit the indication of the emergency condition and the location to server 604 via network 602 (1404).

Server 604 may determine a preferential treatment pathway for the patient based on the emergency condition and location of the patient (1406). Certain patient conditions, such as LVO stroke, are best treated at particular hospitals or medical centers and by certain physicians. Based on the patient condition and location, server 604 may select a preferred a treatment path including such a center and physicians, and notify first responders to route the patient to the center (1408). Server 604 may alert the medical center of the patient condition (1410), which may begin preparing appropriate treatments and equipment for the arrival of the patient in response to the notification.

Techniques of this disclosure may allow respective machine learning classifier routines for three or more sensor types, e.g., brain, cardiac, and motion, to assess and determine the probability of the condition, e.g., LVO. In this example classifier, if the 3-blended sensors all trigger "YES", the probability of LVO is greater than 95% probability, e.g., 96.5%. Conversely, if the 3-blended sensors all trigger "NO", the probability of LVO is less than 5% probability. Any combination of the 3-blended sensor classifier will result in a probability of LVO or other stroke between 5% and 95% (for example; brain triggered YES, cardiac triggered NO, accelerometry triggered YES yields probability of 80%). It should be noted that as more and more events are detected, individual data can be merged with population data to further enhance the classifier routine sensitivity and specificity. Because the techniques of this disclosure may result in sensitive and specific detection/prediction of conditions, it may be appropriate for emergency response systems and specialty medical centers to activate resources to treat the patient in response to the determination by the algorithms. In some examples, a sensor device may communicate, e.g., using tissue conductance communication (TCC), with other concomitant devices and sensor, e.g., an implantable cardioverter-defibrillator (ICD), in order to improve accuracy before deciding to activate the emergency response pathway. In some examples, server 604 may decide to activate the emergency response pathway after both a risk score indicated condition and detection of the condition using traditional algorithms, e.g., real time detection. For example, if a patient's VT/VF risk score is higher than a threshold and sensor device detects VT/VF episode, then the chance of it being a true event is higher than real time detection alone. In some examples, systems according to this disclosure may detect a cardiac mechanical signal using an accelerometer along with an ECG to detect and distinguish asystole, VT/VF, or pulseless electrical activity (PEA). Systems described herein may be configured for use in the technique illustrated in FIG. 14 for a variety of emergency conditions, such as myocardial infarction based on, e.g., ST segment elevation, syncope, brady pause, (e.g., patient falls and show no motion after event, can conclude its an EXTREME emergency, if patient falls and posture/activity shows upright and walking around after event, can conclude it's a LESSER emergency), fall detection alert (e.g., grade fall based upon acceleration vector during fall and post fall recovery indicators, traumatic brain injury (e.g., concussion detection with accelerometry, respiration distress based on impedance signals, motion signals, and ECG signals, and QT interval elongation (e.g., triggered on a time-based average. Multiple vector approach allows ECG fidelity beyond just R-wave).

As discussed above, processing circuitry may determine a surrogate measure of blood pressure as a parameter for the analyses described herein. Hypertension is considered a significant risk factor for stroke and epilepsy. Elevated blood pressure is common in stroke and seizure patients and may be an onset predictor of stroke and/or seizures. Reducing blood pressure is considered a first order risk mitigator to manage patients at risk for such conditions.

PTT is inversely related to blood pressure, and may be utilized as a surrogate for blood pressure for the analyses described herein. Signals indicative of cardiac pulse pressure waves may be acquired by a sensor device implanted above the shoulders, e.g., cranially. Given that cerebral blood flow is prioritized, pulse pressure signals acquired above the shoulder may have greater fidelity, e.g., be less variable, than those acquired from other body locations.

In some examples, processing circuitry may determine a PTT value of a patient based on a sensed ECG signal from electrodes and a signal concurrently sensed by optical sensors 291, 363. The processing circuitry may identify an R wave within a cardiac cycle and associate a first time (T1) with the occurrence of the R wave. Next, the processing circuitry may identify a fluctuation in the light detected by light detectors 40A, 40B occurring after T1, and associate a second time (T2) with the fluctuation, which may represent the passing of blood ejected during the observed cardiac cycle through the portion of the vasculature near light detectors 294, 367. By subtracting T2 from T1, the processing circuitry of IMD 10 then may determine a PTT value. The processing circuitry may determine T2 by identifying a fluctuation in the intensity and/or wavelength of light detected by light detectors 294, 367 occurring after T1, and associate the second time (T2) with the fluctuation, which may represent the passing of blood ejected during the cardiac cycle through the portion of the vasculature near the light detectors. In order to generate such signals, light emitter 292, 365 may emit light at one or more wavelengths in the NIR, visible, green, or amber spectra into tissue. A portion of the emitted light is absorbed by the tissue, and a portion of the emitted light is reflected by the tissue and received by the light detectors.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A system comprising:
a sensor device comprising:
a housing configured to be disposed above shoulders of a patient;
a plurality of electrodes configured to be disposed above the shoulders of the patient;
a motion sensor within the housing; and
sensing circuitry within the housing, the sensing circuitry configured to:
sense, via the plurality of electrodes configured to be disposed above the shoulders of the patient, a brain signal and a cardiac signal of the patient; and
sense, via the motion sensor configured to be disposed above the shoulders of the patient, a motion signal of the patient; and
processing circuitry configured to:
determine values over time of one or more parameters from the brain signal;
determine values over time of one or more parameters from the cardiac signal;
generate at least one of a detection, prediction, or classification of a condition of the patient based on the values over time of the one or more parameters from the brain signal, the values over time of the one or more one or more parameters from the cardiac signal, and the motion signal, wherein the condition comprises a stroke or a seizure; and
output an indication of the at least one of a detection, prediction, or classification to a computing device.

2. The system of claim 1, wherein the housing is configured to be disposed at one of a rear portion of a neck or skull of the patient, or a temporal location of the patient.

3. The system of claim 1, wherein the values over time of the one or more parameters from the cardiac signal indicate autonomic activity of the patient.

4. The system of claim 1, wherein the processing circuitry is configured to:
compare a time course of the values over time of the one or more parameters from the brain signal to a time course of the values over time of the one or more one or more parameters from the cardiac signal; and
generate the classification of the condition as one of neurogenic or cardiogenic based on the comparison.

5. The system of claim 1, wherein the condition comprises stroke, and the processing circuitry is configured to apply a stroke detection or prediction algorithm to the values over time of the one or more parameters from the brain signal and the values over time of the one or more one or more parameters from the cardiac signal to generate the at least one of the detection or prediction of stroke of the patient, wherein the processing circuitry is further configured to:
detect a fall of the patient based on the motion signal; and
change an operating point for the algorithm from a first value to a second value, the second value having higher sensitivity than the first value, in response to detecting the fall.

6. The system of claim 5, wherein the processing circuitry is configured to:
detect a near fall of the patient based on the motion signal; and
change the operating point for the algorithm from the first value to a third value, the third value having higher sensitivity than the first value and lower sensitivity than the second value, in response to detecting the near fall.

7. The system of claim 1,
wherein the sensing circuitry is configured to sense at least one of:
a respiration signal of the patient;
impedance via the electrodes;
a ballistocardiogram signal via the motion sensor
wherein the processing circuitry is configured to generate the at least one of the detection, prediction, or classification of the condition of the patient based on the at least one of the respiration signal, the impedance, or the ballistocardiogram signal.

8. The system of claim 1, further comprising an optical sensor configured for implantation above the shoulders, wherein the processing circuitry is configured to:
determine a pulse transit time (PTT) based on a signal from the optical sensor; and
generate the at least one of the detection, prediction, or classification of the condition of the patient based on the PTT.

9. The system of claim 1, wherein the processing circuitry is configured to generate a classification of the stroke as ischemic or hemorrhagic.

10. The system of claim 9, wherein the one or more parameters from the brain signal comprise one or more of a frequency or amplitude of the brain signal, and the one or more parameters from the cardiac signal comprise a heart beat variability, and wherein, to generate the classification of the stroke as ischemic or hemorrhagic, the processing circuitry is configured to:
generate the classification of the stroke as hemorrhagic based on identifying an increase in heart beat variability following a suppression of the one or more of frequency or amplitude of the brain signal; and
generate the classification of the stroke as ischemic based on identifying the increase in heart beat variability before the suppression of the one or more of frequency or amplitude of the brain signal.

11. The system of claim 1, wherein the processing circuitry is configured to at least one of:
generate the classification of the condition as one of epilepsy or non-epilepsy; or
generate the classification of the condition as one of epilepsy, psychogenic attack, or syncope.

12. The system of claim 1, wherein the processing circuitry is configured to generate a probabilistic classification of the patient condition as one of a plurality of conditions.

13. The system of claim 1, wherein the brain signal comprises an electroencephalogram signal and the cardiac signal comprises at least one of an electrocardiogram signal or a signal indicative of cardiac contractions.

14. The system of claim 13, wherein the processing circuitry is configured to determine values over time of one or more parameters from the cardiac signal using both the electrocardiogram signal and the signal indicative of cardiac contraction.

15. The system of claim 1, wherein the plurality of electrodes comprise at least one electrode disposed on the housing.

16. The system of claim 1, wherein the plurality of electrodes comprise at least one electrode carried by an electrode extension coupled to the housing.

17. The system of claim 16, wherein the electrode extension comprises a first electrode extension extending in a first direction from the housing, the sensor device comprises a second electrode extension including at least one of the plurality of electrodes extending in a second direction from the housing, and the second direction is opposite the first direction.

18. The system of claim 1, wherein the processing circuitry is configured to generate the at least one of the detection, prediction, or classification of the condition of the patient based on at least one of:

a posture of the patient determined based on the motion signal;

a posture change of the patient detected based on the motion signal;

a fall detected based on the motion signal;

a trauma detected based on the motion signal; or head movement frequency detected based on the motion signal.

19. A method comprising:

sensing, via a plurality of electrodes of a sensor device, a brain signal and a cardiac signal of a patient, the sensor device comprising a housing carrying the plurality of electrodes, wherein the housing is configured to be disposed above the shoulders of the patient;

sensing, via a motion sensor of the sensor device disposed above the shoulders of the patient, a motion signal of the patient;

determining values over time of one or more parameters from the brain signal;

determining values over time of one or more parameters from the cardiac signal;

generating at least one of a detection, prediction, or classification of a condition of the patient based on the values over time of the one or more parameters from the brain signal, the values over time of the one or more one or more parameters from the cardiac signal, and the motion signal, wherein the condition comprises a stroke or a seizure; and outputting an indication of the at least one of a detection, prediction, or classification to a computing device.

20. The method of claim 19, wherein the sensor device is disposed at one of a rear portion of a neck or skull of the patient, or a temporal location of the patient.

21. The system of claim 1, wherein the condition comprises the stroke.

* * * * *